(12) United States Patent
Vogels et al.

(10) Patent No.: US 6,878,549 B1
(45) Date of Patent: Apr. 12, 2005

(54) PACKAGING SYSTEMS FOR HUMAN RECOMBINANT ADENOVIRUS TO BE USED IN GENE THERAPY

(75) Inventors: Ronald Vogels, Linschoten (NL); Abraham Bout, Moerkapelle (NL)

(73) Assignee: Introgene B.V., Leiden (NL)

( * ) Notice: Subject to any disclaimer, the term of this patent is extended or adjusted under 35 U.S.C. 154(b) by 0 days.

(21) Appl. No.: 09/332,803

(22) Filed: Jun. 14, 1999

Related U.S. Application Data

(63) Continuation-in-part of application No. 09/065,752, filed on Apr. 24, 1998, now Pat. No. 6,670,188.

(51) Int. Cl.[7] ..................... C12N 15/861; C12N 15/63; C12N 15/64

(52) U.S. Cl. .................... 435/463; 435/320.1; 435/455; 435/456; 435/69.1; 435/91.4

(58) Field of Search ............................. 435/320.1, 455, 435/456, 5, 6, 463, 69.1, 91.4

(56) References Cited

U.S. PATENT DOCUMENTS

| | | | |
|---|---|---|---|
| 4,405,712 A | 9/1983 | Vande Woude et al. | |
| 4,497,796 A | 2/1985 | Salser et al. | |
| 4,727,028 A | 2/1988 | Santerre et al. | |
| 4,740,463 A | 4/1988 | Weinberg et al. | |
| 5,190,931 A | 3/1993 | Inouye | |
| 5,208,149 A | 5/1993 | Inouye | |
| 5,378,618 A | 1/1995 | Sternberg et al. | |
| 5,518,913 A | 5/1996 | Massie et al. | |
| 5,545,522 A | 8/1996 | Van Gelder et al. | |
| 5,652,224 A | 7/1997 | Wilson et al. | |
| 5,670,488 A | 9/1997 | Gregory et al. | |
| 5,707,618 A | 1/1998 | Armentano et al. | |
| 5,753,500 A | 5/1998 | Shenk et al. | |
| 5,837,511 A | 11/1998 | Falck-Pedersen et al. | |
| 5,922,315 A | * 7/1999 | Roy ........................ | 424/93.2 |
| 5,922,576 A | 7/1999 | He et al. | |
| 5,935,935 A | 8/1999 | Connelly et al. | |
| 5,994,106 A | 11/1999 | Kovesdi et al. | |
| 5,994,128 A | * 11/1999 | Fallaux et al. .............. | 435/325 |
| 6,033,908 A | 3/2000 | Bout et al. | |
| 6,040,174 A | 3/2000 | Imler et al. | |

FOREIGN PATENT DOCUMENTS

| | | |
|---|---|---|
| AU | A-28533/95 | 3/1996 |
| CA | 2053187 | 4/1993 |
| CA | 2117668 | 9/1995 |
| EP | 95201611.1 | 6/1995 |
| EP | 95201728.3 | 6/1995 |
| FR | 2707664 | 1/1995 |
| WO | WO 94/12649 | 6/1994 |
| WO | WO 94/23582 | 10/1994 |
| WO | WO 94/26914 | 11/1994 |
| WO | WO 94/28152 | 12/1994 |
| WO | WO 95/00655 | 1/1995 |
| WO | WO 95/02697 | 1/1995 |
| WO | WO 95/27071 | 10/1995 |
| WO | WO 96/16676 | 6/1996 |
| WO | WO 96/18418 | 6/1996 |
| WO | WO 96/26281 | * 8/1996 |
| WO | WO 96/33280 | 10/1996 |
| WO | WO 96/40955 | 12/1996 |
| WO | WO 97/00326 | 1/1997 |
| WO | WO 97/00947 | 1/1997 |
| WO | WO 97/04119 | 2/1997 |
| WO | WO 97/05255 | 2/1997 |
| WO | WO 98/22609 | * 5/1998 |

OTHER PUBLICATIONS

K. L. Berkner, Expression of Heterologous Sequences in Adenoviral Vectors, Current Topics in Microbiology and Immunology, vol. 158, Springer–Verlag Berlin Heidelberg 1992.*

Leslie Stratford–Perricaudet et al, Gene transfer into animals: the promise of adenovirus, Human Gene Transfer, 1991, vol. 219, pp. 51–61.*

Amalfitano et al., "Improved adenovirus packaging cell lines to support the growth of replication–defective gene–delivery vectors", Proc. Natl. Acad. Sci. USA, 93:3352–3356, Apr. 1996.

Amalfitano et al., "Isolation and characterization of packaging cell lines that coexpress the adenovirus E1, DNA polymerase, and preterminal proteins: implications for gene therapy", Gene Therapy, 4:258–263, 1997.

Armentano et al., "Characterization of an Adenovirus Gene Transfer Vector Containing an E4 Deletion", Human Gene Therapy, 6:1343–1353, Oct. 1995.

Blase et al., Vectors in Cancer therapy: how will they delier?, Cancer Gene Therapy, vol. 2, No. 4, 1995, pp. 291–297.

Bout et al., "In vivo adenovirus–mediated transfer of human CFTR cDNA to Rhesus monkey airway epithelium: efficacy, toxicity and safety", Gene Therapy 1, pp. 385–394, 1994.

Bout et al., "Lung Gene Therapy: In Vivo Adenovirus–Mediated Gene Transfer to Rhesus Monkey Airway Epithelium", Human Gene Therapy, 5:3–10, 1994.

Brough et al., "A Gene Transfer Vector–Cell Line System for Complete Functional Complementation of Adenovirus Early Regions E1 and E4", Journal of Virology, 70(9):6497–6501, Sep. 1996.

(Continued)

Primary Examiner—David Guzo
(74) Attorney, Agent, or Firm—TraskBritt

(57) ABSTRACT

Methods and corresponding compounds for generating adenoviral vectors. One such method entails a method for generating an adenoviral vector comprising welding together two nucleic acid molecules wherein the molecules comprise partially overlapping sequences capable of combining with each other allowing the generation of a physically linked nucleic acid comprising at least two functional adenovirus inverted terminal repeats, a functional encapsulation signal and a nucleic acid of interest or functional parts, derivatives and/or analogues thereof. Further disclosed are nucleic acid molecules for generating adenoviral vectors.

11 Claims, 27 Drawing Sheets

OTHER PUBLICATIONS

Brough et al., Stable Cell Lines for Complementation of Adenovirus Early Regions E1, E2A and E4; *Abstract Book CSH Conference On Gene Therapy*, 42, 1996.

Brough et al., "Construction, Characterization, and Utilization of Cell Lines Which Inducibly Express the Adenovirus DNA–Binding Protein", *Virology*, 190:624–634, 1992.

Caravokyri et al., "Constitutive Episomal Expression of Polypeptide IX (pIX) in a 293–Based Cell Line Complements the Deficiency of pIX Mutant Adenovirus Type 5", *Journal of Virology*, 69 (11):6627–6633, Nov. 1995.

Fallaux et al., "Characterization of 911: A New Helper Cell Line for the Titration and Propagation of Early Region 1–Deleted Adenoviral Vectors", *Human Gene Therapy*, 7:215–222, 1996.

Fallaux et al., "New Helper Cells and Matched Early Region 1–Deleted Adenovirus Vectors Prevent Generation of Replication–Competent Adeoviruses", *Human Gene Therapy*, 9:1909–1917, Sep. 1, 1998.

Fisher et al., "Recombinant Adenovirus Deleted of All Viral Genes for Gene Therapy of Cystic Fibrosis", *Virology*, 217:11–22, 1996.

Gao et al., "Biology of Adenovirus Vectors with E1 and E4 Deletions for Liver–Directed Gene Therapy", *Journal of Virology*, 70(12):8934–8943, Dec. 1996.

Gorziglia et al., "Elimination of both E1 and E2a from Adenovirus Vectors Further Improves Prospects for In Vivo Human Gene Therapy", *Journal of Virology*, 70 (6):4173–4178, Jun. 1996.

Haddada et al., "Adenoviral Interleukin–2 Gene Transfer into P815 Tumor Cells Abrogates Tumorigenicity and Induces Antitumoral Immunity in Mice", *Human Gene Therapy*, 4:703–711, 1993.

Hardy et al., "Construction of Adenovirus Vectors through Cre–lox Recombination", *Journal of Virology*, 71 (3):1842–1849, Mar. 1997.

Hahir et al., "Molecular Characterization of Replication–Competent Variants of Adenovirus Vectors and Genome Modifications To Prevent Their Occurrence", *Journal of Virology*, 70 (12):8459–8467, Dec. 1996.

Imler et al., "Novel complementation cell lines derived from human lung carcinoma A549 cells support the growth of E1–deleted adenovirus vectors", *Gene Therapy*, 3:75–84, 1996.

Kornberg, Arthur, "DNA Replication", W.H. Freeman and Company, San Francisco, 8 pages.

Krougliak et al., "Development of Cell Lines Capable of Complementing E1, E4, and Protein IX Defective Adenovirus Type 5 Mutants", *Human Gene Therapy*, 6:1575–1586, Dec. 1995.

Lieber et al., "Recombinant Adenoviruses with Large Deletions Generated by Cre–Mediated Excision Exhibit Different Biological Properties Compared with First–Generation Vectors In Vitro and In Vivo", *Journal of Virology*, 70:8944–8960, Dec. 1996.

Ngo et al., "Computational Complexity, Protein Structure Prediction, and the Levinthal Paradox", *The Protein Folding Problem and Tertiary Structure Prediction*, 5 pages.

Sabatie et al., "Process Development for the Production of Second Generation Adenovirus Vectors for Gene Transfer in Clinical Protocols", *Abstract Book 14th Meeting on Animal Cell Technology*, BI–3, 1996.

Schaack et al., "Adenovirus Type 5 Precursor Terminal Protein–Expressing 293 and HeLa Cell Lines", *Journal of Virology*, 69 (7):4079–4085, Jul.1995.

Vanhaesebroeck et al., *Virology*, 176(2), pp. 362–368, Jun. 1990.

Vincent et al., "Herpes Simplex Virus Thymidine Kinase Gene Therapy for Rat Malignant Brain Tumors", *Human Gene Therapy* 7:197–205, Jan. 20, 1996.

Vincent et al., "Treatment of leptomeningeal metastases in a rat model using a recombinant adenovirus containing the HSV–tk gene", *J. Neurosurg.*, vol. 85, pp. 648–654, 1996.

Wang et al., "A packaging cell line for propagation of recombinant adenovirus vectors containing two lethal gene–region deletions", *Gene Therapy*, 2:775–783, 1995.

Yeh et al., "Efficient Dual Transcomplementation of Adenovirus E1 and E4 Regions from a 293–Derived Cell Line Expressing a Minimal E4 Functional Unit", *Journal of Virology*, 70(1):559–565, Jan. 1996.

Zhou et al., "Development of a Complementing Cell Line and a System for Construction of Adenovirus Vectors with E1 and E2a Deleted",*Journal of Virology*, 70(1):7030–7038, Oct. 1996.

* cited by examiner

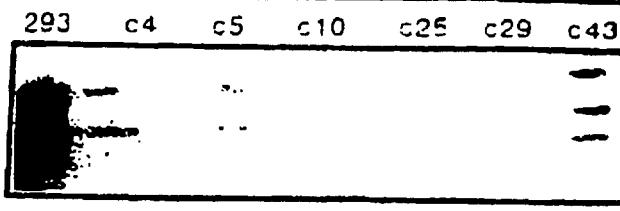
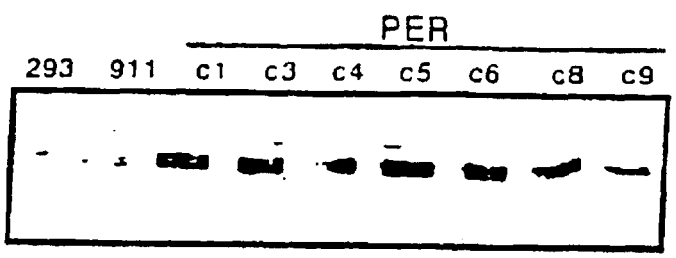
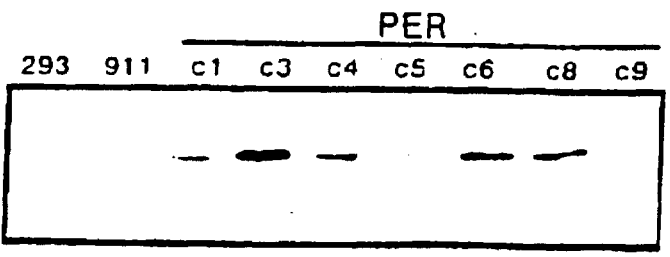
FIG. 7

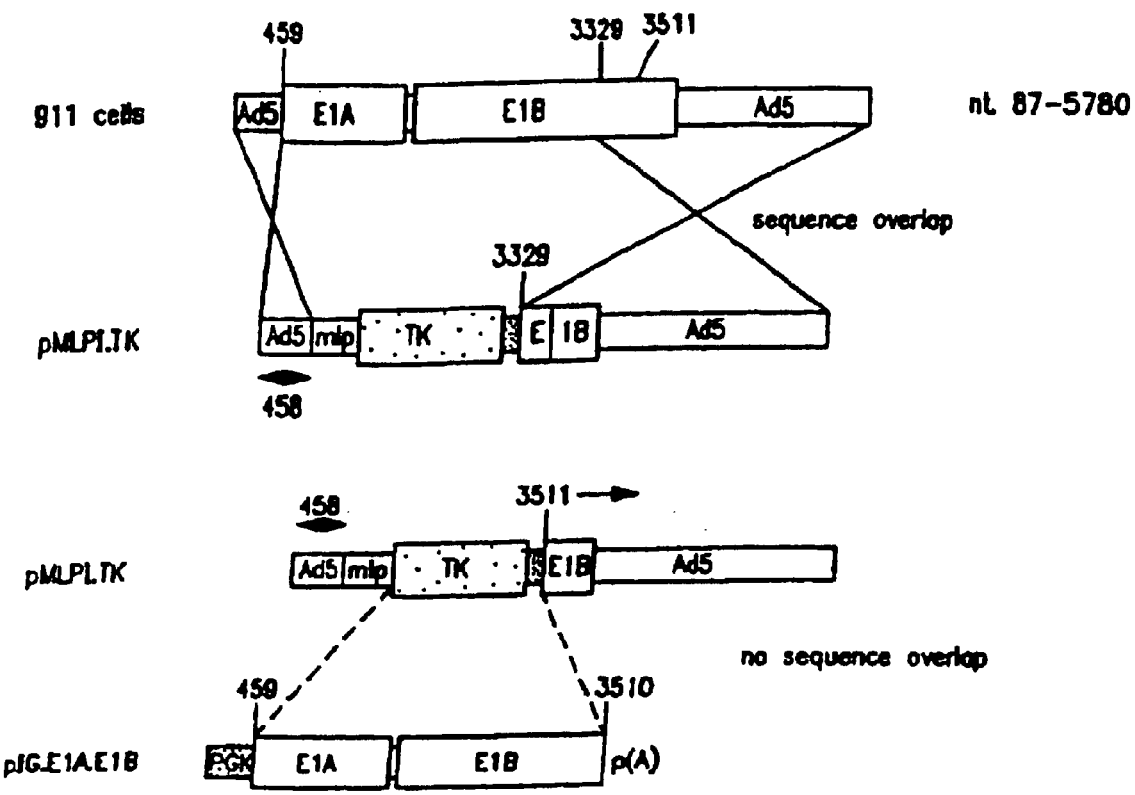
FIG. IIA
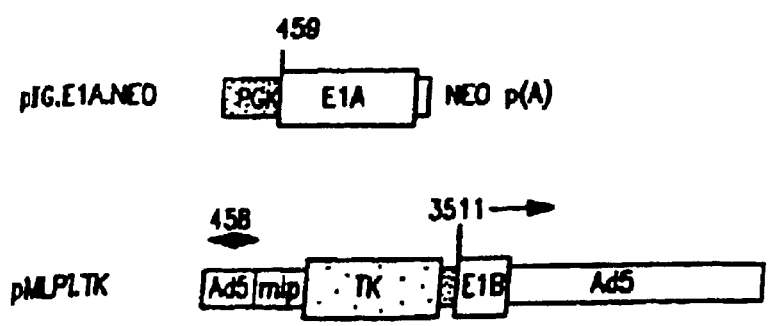
FIG. IIB

```
5'-GTACACTGACCTAGTGCCGCCCGGGCA
             |||||||||||||||| A
         GATCACGGCGGGCCCGA
```

(SEQ ID NO:47)

FIG.15

Figure 20: Cloned adenovirus fragments

Figure 21: Adapter plasmid pAd5/L420-HSA

Figure 22: Adapter plasmid pAd5/CLIP

Figure 23: Generation of recombinant adenoviruses

Figure 24: Minimal adenovirus vector pMV/L420H

Figure 25: Construction of pWE/AdΔ5'

US 6,878,549 B1

PACKAGING SYSTEMS FOR HUMAN RECOMBINANT ADENOVIRUS TO BE USED IN GENE THERAPY

CROSS-REFERENCE TO RELATED APPLICATIONS

This application is a continuation-in-part of U.S. patent application Ser. No. 09/065,752 filed on Apr. 24, 1998, now U.S. Pat. No. 6,670,188, the contents of which are incorporated by this reference.

TECHNICAL FIELD

The invention relates to the field of recombinant DNA technology, especially the field of gene therapy. More specifically, the invention relates to gene therapy using materials derived from adenovirus, in particular human recombinant adenovirus. It particularly relates to novel virus derived vectors and novel packaging cell lines for vectors based on adenoviruses.

BACKGROUND

Gene therapy is a relatively recently developed concept for which a wide range of applications can be and have been envisaged. In gene therapy, a molecule carrying genetic information is introduced into some or all the cells of a host, as a result of which, the genetic information is added to the host in a functional format. Gene therapy also includes the treatment of genetic disorders by providing the genetic information for supplementing a protein or other substance which is, due to the genetic disorder, not present or present in insufficient amounts in the host, and the treatment of tumors and (other) acquired disease such as (auto) immune diseases or infections, or other processes. The genetic information added may be a gene or a derivative of a gene, such as a cDNA, which encodes a protein. In this case, the functional format means that the protein can be expressed by the machinery of the host cell. The genetic information can also be a sequence of nucleotides complementary to a sequence of nucleotides (be it DNA or RNA) present in the host cell. The functional format in this case is that the added DNA (nucleic acid) molecule or copies made thereof in situ are capable of base pairing with the complementary sequence present in the host cell.

Thus, basically three different approaches exist in gene therapy, one directed towards compensating a deficiency present in a (mammalian) host, the second directed towards the removal or elimination of unwanted substances (organisms or cells), and the third directed towards application of a recombinant vaccine (tumors or foreign microorganisms).

For the purpose of gene therapy, adenoviruses carrying deletions have been proposed as suitable vehicles. Adenovirus is a non-enveloped DNA viruses. Gene transfer vectors derived from adenoviruses (so called "adenoviral vectors") have a number of features that make them particularly useful for gene transfer for such purposes. For example, the biology of the adenoviruses is characterized in detail, the adenovirus is not associated with severe human pathology, the virus is extremely efficient in introducing its DNA into the host cell, the virus can infect a wide variety of cells and has a broad host range, the virus can be produced in large quantities with relative ease, and the virus can be rendered replication detective by deletions in the early region 1 ("E1") of the viral genome.

The genome of adenovirus ("Ad") is a linear double-stranded DNA molecule of approximately 36,000 base pairs ("bp") with a 55-kDa terminal protein covalently bound to the 5'terminus of each strand. The Ad DNA contains identical Inverted Terminal Repeats ("ITRs") of about 100 bp, with the exact length depending on the serotype. The viral origins of replication are located within the ITRs exactly at the genome ends. DNA synthesis occurs in two stages. First, the replication proceeds by strand displacement, generating a daughter duplex molecule and a parental displaced strand. The displaced strand is single stranded and can form a so called "panhandle" intermediate, which allows replication initiation and generation of a daughter duplex molecule. Alternatively, replication may proceed from both ends of the genome simultaneously, obviating the requirement to form the panhandle structure. The replication is summarized in FIG. 14 adapted from Lechner et al., (1977) *J. Mol. Biol.* 174:493–510.

During the productive infection cycle, the viral genes are expressed in two phases: the early phase, which is the period up to viral DNA replication, and the late phase, which coincides with the initiation of viral DNA replication. During the early phase only the early gene products, encoded by regions E1, E2, E3 and E4, are expressed, which carry out a number of functions that prepare the cell for synthesis of viral structural proteins (Berk, A. J. (1986) *Ann. Rev. Genet.* 20:45–79). During the late phase, the late viral gene products are expressed in addition to the early gene products and host cell DNA and protein synthesis are shut off. Consequently, the cell becomes dedicated to the production of viral DNA and of viral structural proteins (Tooze, J. *DNA Tumor Viruses* (revised), Cold Spring Harbor Laboratory, Cold Spring Harbor, N.Y., 1981).

The E1 region of adenovirus is the first region of adenovirus expressed after infection of the target cell. This region consists of two transcriptional units, the E1A and E1B genes, both of which are required for oncogenic transformation of primary (embryonal) rodent cultures. The main functions of the E1A gene products are to induce quiescent cells to enter the cell cycle and resume cellular DNA synthesis, and to transcriptionally activate the E1B gene and the other early regions (E2, E3 and E4) of the viral genome. Transfection of primary cells with the E1A gene alone can induce unlimited proliferation (immortalization), but does not result in complete transformation. However, expression of E1A in most cases results in induction of programmed cell death (apoptosis), and only occasionally is immortalization obtained (Jochemsen et al. *EMBO J.* 6:3399–3405 (1987)). Co-expression of the E1B gene is required to prevent induction of apoptosis and for complete morphological transformation to occur. In established immortal cell lines, high level expression of E1A can cause complete transformation in the absence of E1B (Roberts et al., *J. Virol.* 56:404–413 (1981)).

The E1B encoded proteins assist E1A in redirecting the cellular functions to allow viral replication. The E1B 55 kD and E4 33 kD proteins, which form a complex that is essentially localized in the nucleus, function in inhibiting the synthesis of host proteins and in facilitating the expression of viral genes. Their main influence is to establish selective transport of viral mRNAs from the nucleus to the cytoplasm, concomitantly with the onset of the late phase of infection. The E1B 21 kD protein is important for correct temporal control of the productive infection cycle, thereby preventing premature death of the host cell before the virus life cycle has been completed. Mutant viruses incapable of expressing the E1B 21 kD gene product exhibit a shortened infection cycle that is accompanied by excessive degradation of host cell chromosomal DNA (deg-phenotype) and in an enhanced cytopathic effect (cyt-phenotype). Telling et al., *J. Virol.* 68:541–7 (1994). The deg and cyt phenotypes are suppressed when in addition the E1A gene is mutated, indicating that these phenotypes are a function of E1A (White et al., (1988) *J. Virol.* 62:3445–3454). Furthermore, the E1B 21 kDa protein slows down the rate by which E1A switches on the other viral genes. It is not yet known by which mechanisms E1B 21 kD quenches these E1A dependent functions.

Vectors derived from human adenoviruses, in which at least the E1 region has been deleted and replaced by a gene of interest, have been used extensively for gene therapy experiments in the pre-clinical and clinical phase, and all adenoviral vectors currently used in gene therapy have a deletion in the E1 region, where novel genetic information can be introduced. The E1-deletion renders the recombinant virus replication defective (Stratford-Perricaudet et al., (1991) pp. 51–61. In O. Cohen-Adenaur, and M. Boiron (Eds): *Human Gene Transfer*, John Libbey Eurotext).

In contrast to, for example, retroviruses, adenoviruses do not integrate into the host cell's genome, are able to infect non-dividing cells, and are able to efficiently transfer recombinant genes in vivo (Brody et al., (1994) *Ann NY Acad. Sci.* 716:90–101). These features make adenoviruses attractive candidates for in vivo gene transfer of, for example, suicide or cytokine genes into tumor cells. However, a problem associated with current recombinant adenovirus technology is the possibility of unwanted generation of replication competent adenovirus ("RCA") during the production of recombinant adenovirus (Lochmüller et al., (1994) *Hum. Gene Ther.* 5:1485–1492; Imler et al., (1996) *Gene Ther.* 3:75–84). This is caused by homologous recombination between overlapping sequences of the recombinant vector and the adenovirus constructs present in the complementing cell line, such as 293 cells (Graham et al., (1977) *J. Gen. Virol.* 36:59–72). RCA in batches to be used in clinical trials is unwanted because RCA i) replicates in an uncontrolled fashion; ii) can complement replication defective recombinant adenovirus, causing uncontrolled multiplication of the recombinant adenovirus; and iii) batches induce significant tissue damage and hence strong pathological side effects (Lochmüller et al., (1994) *Hum. Gene Ther.* 5:1485–1492). Therefore, batches to be used in clinical trials should be proven free of RCA (Ostrove, J. M. (1994) *Cancer Gene Ther.* 1:125–131).

One of the additional problems associated with the use of recombinant adenoviral vectors is the host defense reaction against treatment with adenovirus. Briefly, recombinant adenoviruses are deleted for the E1 region (see, above). The adenoviral E1 products trigger the transcription of the other early genes (E2, E3, E4), which consequently activate expression of the late virus genes. Therefore, it was generally thought that E1-deleted vectors would not express any other adenoviral genes. However, recently it has been demonstrated that some cell types are able to express adenoviral genes in the absence of E1 sequences. This indicates that some cell types possess the machinery to drive transcription of adenoviral genes. In particular, it was demonstrated that such cells synthesize E2A and late adenoviral proteins. In a gene therapy setting, this means that transfer of the therapeutic recombinant gene to somatic cells not only results in expression of the therapeutic protein but may also result in the synthesis of viral proteins. Cells that express adenoviral proteins are recognized and killed by cytotoxic T Lymphocytes, which both eradicates the transduced cells and causes inflammation (Bout et al., (1994a) *Gene Therapy* 1:385–394; Engelhardt et al., (1993) *Human Gene Therapy* 4:759–769; Simon et al., (1993) *Human Gene Therapy* 4:771–780).

As this adverse reaction hampers gene therapy, several solutions to this problem have been suggested, such as using immunosuppressive agents after treatment, retaining the adenoviral E3 region in the recombinant vector (see, EPO patent application EP 952022 1B) or using ts mutants of human adenovirus, which have a point mutation in the E2A region (PCT International Patent application WO/28938). However, these strategies to circumvent the immune response have their limitations. The use of temperature sensitive ("ts") mutant recombinant adenovirus diminishes the immune response to some extent, but is less effective in preventing pathological responses in the lungs (Engelhardt et al., (1994a) *Human Gene Ther.* 5:1217–1229). The E2A protein may induce an immune response by itself and it plays a pivotal role in the switch to the synthesis of late adenoviral proteins. Therefore, it is attractive to make recombinant adenoviruses which are mutated in the E2 region, rendering it ts, as has been identified in PCT International Patent application WO/28938. A major drawback of this system is the fact that, although the E2 protein is unstable at the non-permissive temperature, the immunogenic protein is still synthesized. In addition, it is to be expected that the unstable protein does activate late gene expression, albeit to a lesser extent. ts125 mutant recombinant adenoviruses have been tested, and prolonged recombinant gene expression was reported (Yang et al., (1994b) *Nat Genet.* 7:362–369; Engelhardt et al., (1994a) *Hum. Gene Ther.* 5:1217–1229; Engelhardt et al., (1994b) *Proc. Natl. Acad. Sci USA* 91:6196–200; Yang et al., (1995) *J. Virol.* 69:2004–2015). However, pathology in the lungs of cotton rats was still high (Engelhardt et al., (1994a) *Human Gene Ther.* 5:1217–1229), indicating that the use of ts mutants results in only a partial improvement in recombinant adenovirus technology. Others (Fang et al., (1996) *Gene Ther.* 3:217–222) did not observe prolonged gene expression in mice and dogs using ts125 recombinant adenovirus. An additional difficulty associated with the use of ts125 mutant adenoviruses is that a high frequency of reversion is observed. These revertants are either real revertants or the result of second site mutations (Kruijer et al., (1983) *Virology* 124:425–433; Nicolas et al., (1981) *Virology* 108:521–524). Both types of revertants have an E2A protein that functions at normal temperature and therefore have similar toxicity as the wild-type virus.

E1-deleted recombinant adenoviruses are usually made by one of the following methods. In the first method, adenovirus DNA, be it wild type (wt) or E1- and/or E3-deleted, is digested with a restriction enzyme, for example, ClaI, to remove the left ITR, packaging signal and at least part of the E1 sequences and the remaining adenovirus genome fragment (1) is purified. Cotransfection of (1) with a linearized adapter construct (2) containing the left ITR, packaging signal, an expression cassette with the gene of interest and adenovirus sequences overlapping with (1) in a cell line complementing for E1 functions (packaging cell line) will give rise to recombinant adenovirus particles by intra-cellular homologous recombination. Alternatively, an adapter construct (3) containing the left ITR, packaging signal, and an expression cassette with the gene of interest is such that it can be ligated to the adenovirus DNA fragment (1) followed by transfection into packaging cells. The disadvantage of these methods is that the purification of (1) is laborious and that incomplete digestion of wt DNA results in introduction of wt adenovirus into the culture leading to contamination. An approach to circumvent this problem has been by the construction of clone pHBG10 described by Bett et al., (1994) *Natl. Acad. Sci. USA* 91:8802–8806. This plasmid clone contains adenovirus 5 ("Ad5") sequences with a deletion of the packaging signal and part of the E1 region and with the viral ITRs attached to each other. However, this clone includes adenovirus sequences that are also present in E1-complementing cell lines, including those of the present invention (see, EPO patent application EP 95201611.1). Furthermore, since the ITRs are attached to each other the clone cannot be linearized, resulting in less efficient recombination with the E1 substitution plasmid.

In the second method, recombinant adenoviruses is constructed either by homologous recombination in bacteria (Chartier et al., (1996) *J. Virol.* 70, No. 7:4805–4810; Crouzet et al., (1997) *Proc. Natl. Acad Sci USA* 94:1414–1419) or by cloning into cosmid vectors (Fu et al., (1997) *Hum. Gene Ther.* 8:1321–1330) and subsequent transfection into an E1 complementing cell line. The disadvantage of this method is that it demands extensive analysis of each generated clone (~35 kb) by restriction enzyme digestion before transfection to exclude deletions that occurred due to recombination in the bacteria. In addition, the use of cloned adenovirus sequences does not solve the problem of sequence overlap between commonly used packaging cells and recombinant viruses leading to production of RCA during propagation.

A third method that is used is a two-step gene replacement technique in yeast, starting with a complete adenovirus genome (Ad2) (Ketner et al., *Proc. Natl. Acad. Sci. USA* 91:6186–6190 (1994)) cloned in a Yeast Artificial Chromosome ("YAC") and a plasmid containing adeno sequences to target a specific region in the YAC clone, an expression cassette for the gene of interest and a positive and negative selectable marker. This method requires yeast technology and extensive analysis of each new recombinant clone (even more cumbersome than the above described method, due to the large size of YACS).

A fourth method uses a cosmid clone (pAdex1w; Miyake et al., (1996) *Medical Sciences* 93:1320–1324) that carries the Ad5 sequence with deletions in the E1 and E3 sequences. This clone has a unique restriction site replacing part of the E1 region that allows insertion of a foreign expression cassette. For generating recombinant adenoviruses, a DNA-terminal protein complex (DNA-TPC) is isolated from cells infected with a RCA Ad-dlX (wt Ad5 with an XbaI deletion in the E3 region). This DNA is digested with EcoT221 to remove the 5' part of the DNA and co-transfected with the cosmid cloned into E1 complementing cells. Intracellular recombination generates the recombinant virus (Miyake et al., (1996) *Medical Sciences* 93:1320–1324). This method has the disadvantage that replication competent viral DNA is used and the E1 deletion in the cosmid clone is not enough to remove all overlap with E1 sequences in currently used packaging cell lines including those used in the present invention. Thus, current methods to generate RCA-free recombinant adenoviruses have several disadvantages, including the risk of introducing wild-type viruses in the culture, instability of cloned adenovirus sequences, the necessity to check the complete ~35 kb recombinant clone by restriction analysis for each new virus to be generated, and the system being suitable only for E1-deleted recombinant adenoviruses and much more laborious for use with recombinant adenoviruses including E3 substitutions. Furthermore, despite the use of cloned adenovirus DNA in some of the methods, extensive overlap with adenovirus sequences present in commonly used packaging cells like 293 and 911 cells does not solve the problem of appearance of RCA due to homologous recombination during propagation of the virus. Therefore, a need persists for methods and means to produce RCA-free recombinant adenovirus preparations that solve the disadvantages of prior art methods and means discussed above. Gene addition is currently by far the most widely applied gene therapy technique. This is mainly due to the fact that a) homologous recombination is very inefficient and b) for homologous recombination relatively large DNA fragments are required for which no suitable vector systems were available. Thus, currently an unmet need exists for vector systems that efficiently introduce large nucleic acid molecules into mammalian cells.

Recombinant adenoviruses are able to efficiently transfer recombinant genes to the rat liver and airway epithelium of rhesus monkeys (Bout et al., (1994b) *Human Gene Therapy* 5:3–10; Bout et al., (1994a) *Gene Therapy* 1:385–394). In addition, (Vincent et al., (1996) *J. Neurosurg* 85:648–654; Vincent et al., (1996b) *Hum. Gene Ther.* 7:197–205) and others (see, e.g., Haddada et al., (1993) *Hum. Gene Ther.* 4:703–11) have observed an efficient in vivo adenovirus mediated gene transfer to a variety of tumor cells in vitro and to solid tumors in animal models (lung tumors, glioma) and human xenografts in immunodeficient mice (lung) in vivo (reviewed by Blaese et al., *Cancer Gene Ther.* 2:291–297).

Generation of minimal adenoviral vectors has been disclosed in PCT International Patent Application WO 94/12649. The method described exploits the function of the protein IX for the packaging of minimal adenoviral vectors (Pseudo Adenoviral Vectors ("PAV") in the terminology of WO 94/12649). PAVs are produced by cloning an expression plasmid with the gene of interest between the left-hand (including the sequences required for encapsulation) and the right-hand adenoviral ITRS. The PAV is propagated in the presence of a helper virus. Encapsidation of the PAV is preferred compared to the helper virus because the helper virus is partially defective for packaging (either by virtue of mutations in the packaging signal or by virtue of its size (virus genomes greater than 37.5 kb package inefficiently)). In addition, it is proposed that, in the absence of the protein IX gene, the PAV will be preferentially packaged. However, neither of these mechanisms appears to be sufficiently restrictive to allow packaging of only PAVs/minimal vectors. The mutations proposed in the packaging signal diminish packaging, but do not provide an absolute block as the same packaging activity is required to propagate the helper virus. Also neither an increase in the size of the helper virus nor the mutation of the protein IX gene will ensure that PAV is packaged exclusively. Thus, the method described in WO 94/12649 is unlikely to be useful for producing helper-free stocks of minimal adenoviral vectors/PAVs.

DESCRIPTION OF THE INVENTION

The invention includes means and methods for generating adenoviral vectors. In one aspect, the invention entails a method for generating an adenoviral vector including welding together two nucleic acid molecules wherein the molecules include partially overlapping sequences capable of combining with each other allowing the generation of a physically linked nucleic acid including at least two functional adenoviral ITRs, a functional encapsulation signal and a nucleic acid of interest or functional parts, derivatives and/or analogues thereof. The invention further includes nucleic acid molecules for generating adenoviral vectors.

BRIEF DESCRIPTION OF THE DRAWINGS

The hereinafter described drawings may help one in understanding the invention:

FIG. 7 is a Western blot analysis of A549 clones transfected with pIG.E1A.NEO and human embryonic retinoblasts ("HER") transfected with pIG.E1A.E1B (PER clones). Expression of Ad5 E1A and E1B 55 kD and 21 kD proteins in transfected A549 cells and PER cells was determined by Western blot with mouse monoclonal antibodies (Mab) M73 which recognizes E1A gene products and Mabs AIC6 and C1G11, which recognize the E1B 55 kDa and 21 kDa proteins, respectively. Mab binding was visualized using horseradish peroxidase-labeled goat anti-mouse antibody and enhanced chemiluminescence. 293 and 911 cells served as controls.

FIGS. 11a & 11b show that the new adenovirus packaging constructs do not have sequence overlap with the new adenoviral vectors. FIG. 11a is a packaging system based on primary cells. FIG. 11b is a packaging system based on established cell lines: transfection with E1a and selection with G418. Regions of sequence overlap between the packaging construct, pAd5XhoIC expressed in 911 cells and adenoviral vector, pMLP.TK, that can result in homologous recombination and the formation of RCA are shown (Panel A). In contrast, no regions of sequence overlap exist between the new packaging construct, pIG.E1A.E1B, expressed in PER.C6 cells, and the new adenoviral vector, pMLPI.TK, (Panel A) or between the new packaging construct, pIG.E1A.NEO and the new adenoviral vector pMLPI.TK (Panel B) that can result in homologous recombination and the formation of RCA.

FIG. 15 depicts a potential hairpin conformation of a single-stranded DNA molecule that contains the HP/asp sequence. Asp718 I digestion of pICLha, containing the cloned oligonucleotides, HP/asp1 and HP/asp2 yields a linear double-stranded DNA with an Ad5 ITR at one terminus and the HP/asp sequence at the other terminus. In cells expressing the adenoviral E2 region, a single-stranded DNA is produced with an Ad5 ITR at the 5'-terminus and the hairpin conformation at the 3'-terminus. Once formed, the hairpin can serve as a primer for cellular and/or adenoviral DNA polymerase to convert the single stranded DNA to double stranded DNA.

DETAILED DESCRIPTION OF THE INVENTION

Figure 1:
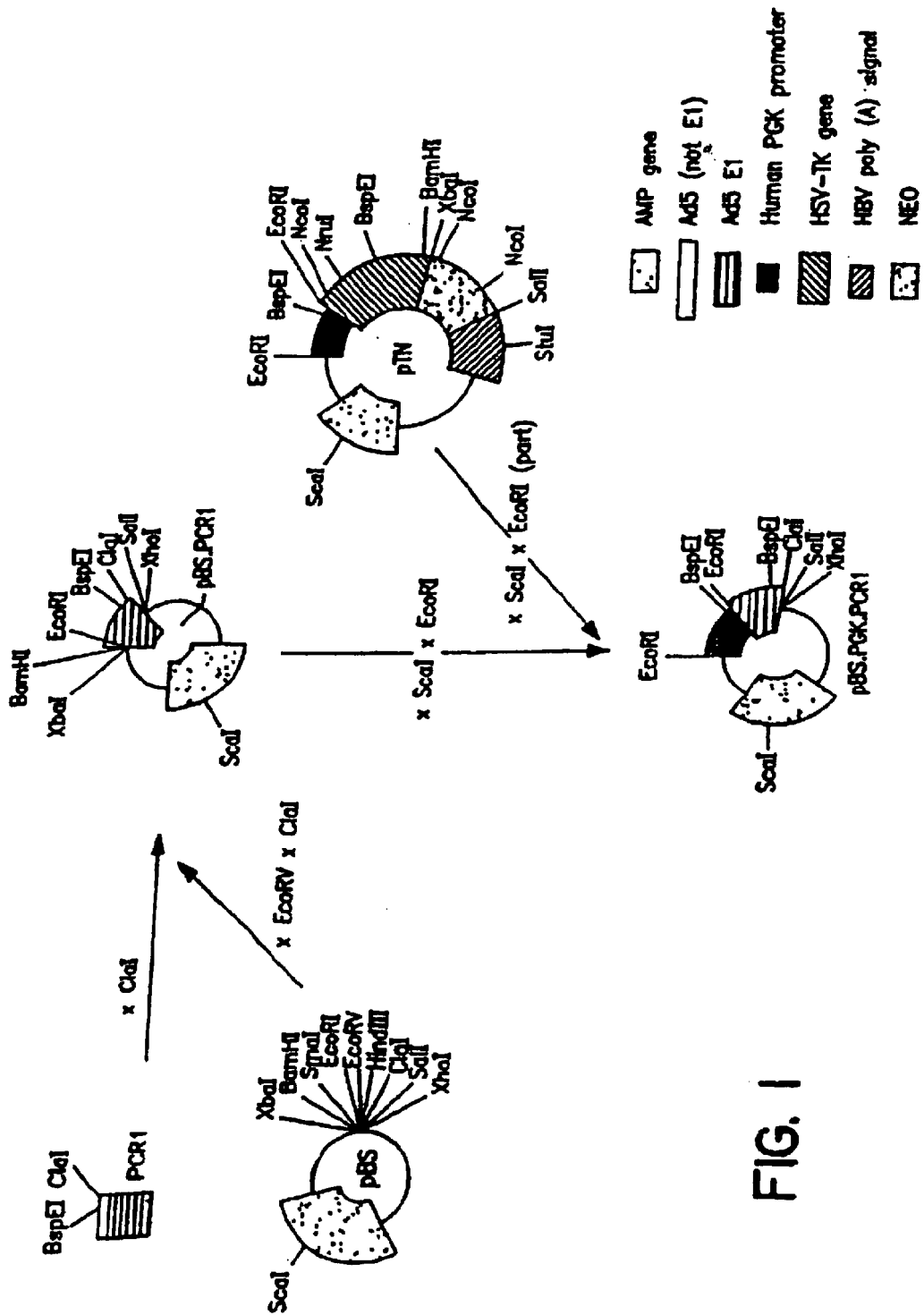
FIG. 1 depicts the construction of pBS.PGK.PCRI. pBS.PGK.PCRI encodes the human phosphoglycerate kinase promoter (PGK) operatively linked to Ad5 E1 nucleotides 459–916. To construct this plasmid, Ad5 nucleotides 459–916 were PCR amplified with primers Ea-1 and Ea-2 (Table I), digested with Cla I and cloned into the Cla I-EcoR V sites of pBluescript (Stratagene), resulting in pBS.PCRI. The PGK promoter was excised from pTN by complete digestion with Sca I and partial digestion with EcoR I and cloned into the corresponding sites of pBS.PCRI, resulting in pBS.PGK.PCRI.

Novel compositions and methods are provided for producing recombinant adenoviruses, not only E1-deleted but also minimal adenoviruses which are free of replication competent adenoviruses. The compositions include constructs suitable for generating double insert viruses. The system provided by the invention to generate, for example, E1-deleted adenoviruses consists of two nucleic acid molecules. A first of which is a relatively small and easy to manipulate adapter plasmid containing at least, in an operable configuration, the left ITR, an optional packaging signal, an expression cassette with the nucleic acid molecule of interest, and sequences homologous to a part of a second molecule that includes at least one partially overlapping nucleic acid molecule that include at least the right ITR and preferably further includes adenovirus sequences encoding adenoviral capsid proteins; and the packaging cells of the invention described infra. Co-transfection of the nucleic acid molecules into the packaging cells allows the welding together of the nucleic acid molecules preferably through essentially one homologous recombination between the overlapping sequences in the nucleic acid molecules.

Homologous recombination generates a recombinant viral DNA that is capable of replicating and propagating on the packaging cells. The nucleic acid molecules preferably have no sequence overlap with complementing sequences in packaging cells that can lead to the formation of RCA. Preferably, at least one of the ITRs on the nucleic acid molecules is flanked by a restriction enzyme recognition site not present in the adenoviral sequences so that the ITR can be made essentially free from vector sequences by digestion of the DNA with that restriction enzyme. In this way, initiation of replication occurs more efficiently.

The system provided by the present invention also greatly facilitates the production of RCA-free recombinant adenoviruses with further modifications in the adenovirus genome, including, for example, modifications in the coding regions for the E4 region proteins, hexon, penton base protein or fiber protein or E2A protein.

The following embodiments should be understood to be read in the light of the combination of adapter plasmid and the large nucleic acid to be welded together therewith.

In one aspect of the invention, we have solved the problem with RCA production in that packaging cells have been developed having no overlapping sequences with a new basic vector, and are thus suited for relatively safe, large-scale production of recombinant adenoviruses.

In another aspect of the present invention, we therefore delete E2A-coding sequences from the recombinant adenovirus genome and transfect these E2A sequences into the (packaging) cell lines containing E1 sequences to complement recombinant adenoviral vectors. Major hurdles to this approach are a) that E2A should be expressed at very high levels and b) that E2A protein is very toxic to cells.

The current invention in yet another aspect therefore discloses use of the ts125 mutant E2A gene, which produces a protein that is unable to bind DNA sequences at the non-permissive temperature. High levels of this protein may be maintained in the cells (because it is not toxic at the particular temperature) until the switch to the permissive temperature is made. This can be combined with placing the mutant E2A gene under the direction of an inducible promoter, such as, for instance, tet, methallothionein, a steroid inducible promoter, retinoic acid β-receptor or other inducible systems. However, in yet another aspect of the invention, the use of an inducible promoter to control the moment of production of toxic wild-type E2A is included.

Two salient additional advantages of E2A-deleted recombinant adenovirus are the increased capacity to harbor heterologous sequences and the permanent selection for cells that express the mutant E2A. This second advantage relates to the high frequency of reversion of ts125 mutation: when reversion occurs in a cell line harboring ts125 E2A, this will be lethal to the cell. Therefore, a permanent selection exists for those cells that express the ts125 mutant E2A protein. In addition, as we in one aspect of the invention generate E2A-deleted recombinant adenovirus, we should not have the problem of reversion in the generated adenoviruses.

In yet another aspect of the invention, the use of non-human cell lines as packaging cell lines is disclosed. For GMP production of clinical batches of recombinant viruses it is desirable to use a cell line that has been used widely for producing other biotechnology products. Most of the latter cell lines are from monkey origin, which have been used to produce, for example, vaccines. These cells cannot be used directly for producing recombinant human adenovirus, as human adenovirus cannot replicate in cells of monkey origin or replicate only at low levels. A block in the switch of early to late phase of adenovirus lytic cycle underlies the defective replication. However, host range ("hr") mutations in the human adenovirus genome are described (hr400–404) which allow replication of human viruses in monkey cells. These mutations reside in the gene encoding E2A protein (Klessig et al., (1979) Cell 17:957–966; Klessig et al., (1984) Virus Res. 1:169–188; Rice et al., (1985) J. Virol. 56:767–778) (Klessig et al., (1984) Virus Res. 1:169–188). Moreover, mutant viruses have been described that harbor both the hr and temperature-sensitive ts125 phenotype (Brough et al., (1985) J. Virol. 55, 206–212; Rice et al., (1985) J. Virol. 56:767–778).

We therefore generate packaging cell lines of monkey origin (e.g., VERO, CV1) that harbor:

a) E1 sequences, to allow replication of E1/E2 defective adenoviruses, b) E2A sequences, containing the hr mutation and the ts125 mutation named ts400 (Brough et al., (1985) J. Virol. 55':206–212; Rice et al., (1985) J. Virol. 56:767–778 to prevent cell death by E2A over expression, c) E2A sequences, just containing the hr mutation, under the control of an inducible promoter, and/or d) E2A sequences, containing the hr mutation and the ts125 mutation (ts400), under the control of an inducible promoter.

Furthermore, we disclose the construction of novel and improved combinations of packaging cell lines and recombinant adenoviral vectors.

The invention provides:

1) A novel packaging cell line derived from diploid HER cells that harbors nt. 80–5788 of the Ad5 genome. This cell line, named 911 (deposited under ECACC deposit accession number 95062101 under the provisions of the Budapest Treaty with the Centre for Applied Microbiology and Research Authority (European Collection of Animal Cell Cultures or "ECACC"), Porton Down, Salisbury, Wiltshire SP4, OJG, United Kingdom, an International Depository Authority), has many characteristics that make it superior to the commonly used 293 cells (Fallaux et al., (1996) Hum. Gene Ther. 7:215–222).

2) Novel packaging cell lines that express just E1A genes and not E1B genes. Established cell lines (and not human diploid cells of which 293 and 911 cells are derived) are able to express E1A to high levels without undergoing apoptotic cell death, as occurs in human diploid cells that express E1A in the absence of E1B. Such cell lines are able to transcomplement E1B-defective recombinant adenoviruses, because viruses mutated for E1B 21 kD protein are able to complete viral replication even faster than wild-type adenoviruses (Telling et al., (1994) J. Virol. 68:541–7). The constructs are described in more detail below, and are graphically represented in FIGS. 1–5. The constructs are transfected into the different established cell lines and are selected for high expression of E1A. This is done by operatively linking a selectable marker gene (e.g., NEO gene) directly to the E1B promoter. The E1B promoter is transcriptionally activated by the E1A gene product and therefore resistance to the selective agent (e.g., G418 in the case NEO is used as the selection marker) results in direct selection for desired expression of the E1A gene.

3) Packaging constructs that are mutated or deleted for E1B 21 kD, but just express the 55 kD protein.

4) Packaging constructs to be used for generating complementing packaging cell lines from diploid cells (not exclusively of human origin) without the need of selection with marker genes. These cells are immortalized by expression of E1A. However, in this particular case, expression of E1B is essential to prevent apoptosis induced by E1A proteins. Selection of E1 expressing cells is achieved by selection for focus formation (immortalization), as described for 293 cells (Graham et al., (1977) *J. Gen. Virol.* 36:59–72) and 911 cells (Fallaux et al., (1996) *Hum. Gene Ther.* 7:215–222), that are E1 transformed human embryonic kidney ("HEK") cells and HER cells, respectively.

5) After transfection of HER cells with construct pIG.E1A.E1B (FIG. 4), seven independent cells lines were established. These cell lines were designated PER.C1, PER.C3, PER.C4, PER.C5, PER.C6, PER.C8 and PER.C9. PER denotes PGK-E1-Retinoblasts. These cell lines express E1A and E1B proteins, are stable (e.g., PER.C6 for more than 57 passages), and complement E1defective adenoviral vectors. Yields of recombinant adenovirus obtained on PER cells are a little higher than obtained on 293 cells. One of these cell lines (PER.C6) was deposited at the ECACC under number 96022940 on Feb. 29, 1996.

6) New adenoviral vectors with extended E1 deletions (deletion nt. 459–3510). Those viral vectors lack sequences homologous to E1 sequences in the packaging cell lines. These adenoviral vectors contain pIX promoter sequences and the pIX gene, as pIX (from its natural promoter sequences) can only be expressed from the vector and not by packaging cells (Matsui et al., (1986) *Mol. Cell Biol.* 6:4149–4154, Hoeben and Fallaux, pers. comm.; Imler et al., (1996) *Gene Ther.* 3:75–84).

7) E2A-expressing packaging cell lines preferably based on either E1A expressing established cell lines or E1A+E1B expressing diploid cells (see, under 2–4). E2A expression is either under the control of an inducible promoter or the E2A ts125 mutant is driven by either an inducible or a constitutive promoter.

8) Recombinant adenoviral vectors as herein described (see, 6) but carrying an additional deletion of E2A sequences.

9) Adenovirus packaging cells from monkey origin that are able to transcomplement E1-defective recombinant adenoviruses. They are preferably co-transfected with pIG.E1A.E1B and pIG.NEO, and selected for NEO resistance. Such cells expressing E1A and E1B are able to transcomplement E1 defective recombinant human adenoviruses, but will do so inefficiently because of a block of the synthesis of late adenoviral proteins in cells of monkey origin (Klessig et al., (1979) *Cell* 17:957–966). To overcome this problem, we generate recombinant adenoviruses that harbor a host-range mutation in the E2A gene, allowing human adenoviruses to replicate in monkey cells. Such viruses are generated as described in FIG. 12., except DNA from a hr-mutant is used for homologous recombination.

10) Adenovirus packaging cells from monkey origin as described under 9, except that they will also be co-transfected with E2A sequences harboring the hr mutation. This situation allows replication of human adenoviruses lacking E1 and E2A (see, under 8). E2A in these cell lines is either under the control of an inducible promoter or the tsE2A mutant is used. In the latter case, the E2A gene will thus carry both the ts mutation and the hr mutation (derived from ts400). Replication competent human adenoviruses have been described that harbor both mutations (Brough et al., *J. Virol.* 55:206–212; Rice et al., (1985) *J. Virol.* 56:767–778).

Furthermore, the present invention, in one aspect, provides new cosmid and plasmid vectors containing large fragments of the adenoviral genome and an improved method for generating recombinant adenoviral vectors by making use of these cloned adenovirus sequences.

Accordingly, the present invention provides a new system to generate recombinant adenoviruses that is fast, highly flexible, reliable and only requires standard cloning technology. The new system is surprisingly efficient in generating recombinant adenoviruses. In combination with the packaging cells of the invention, it ensures RCA-free generation and propagation of recombinant adenoviruses. The previously identified problems associated with current methods to generate recombinant adenoviruses are, in one aspect, solved by using a functional combination of cloned adenovirus sequences and an intra-cellular homologous recombination in suitable packaging cells.

Accordingly, the present invention provides methods and means to efficiently generate and produce vectors that are able to harbor very large fragments of (genomic) DNA. Vectors of the invention can be safely produced to very high titers and are able to transduce mammalian cells, including human cells, with high efficiency, thereby favoring homologous recombination with (genomic) DNA molecules present in the mammalian cells, due to the high numbers of introduced DNA molecules and their large homologous overlap with the target DNA molecules for recombination. In one aspect, vectors according to the invention are based on adenoviral vectors derived from an adenoviral genome, from which as much as possible of the adenoviral genome is deleted except for the ITR sequences and the sequences needed in cis for packaging (minimal adenoviral vectors). Such vectors can accommodate up to 38 kb of foreign (genomic) DNA.

Minimal adenoviral vectors with large genomic sequences functioning as gene replacement vectors can be generated efficiently using the plasmid-based intracellular PCR system disclosed infra, thereby avoiding the need of contaminating helper viruses. In addition, we disclose an alternative way of producing minimal adenoviral vectors without the need for helper viruses. Replication and packaging of the minimal adenoviral vectors with large inserts can also be achieved by using them in combination with a complementing molecule containing all parts of the adenoviral genome that are required for replication and packaging except for the packaging signal and E1 sequences. Such a complementing molecule need not necessarily replicate by the virtue of adenoviral replication machinery. It may, for example, be cloned on a plasmid that also contains the SV40 origin of replication. Transfection of this DNA together with the minimal adenoviral vector in a E1-containing packaging cell that also (inducibly) expresses the SV40 Large T protein will lead to replication of the adenovirus molecule and expression of adenoviral proteins. The latter will then initiate replication and packaging of the minimal adenoviral vectors.

A further aspect of the invention provides otherwise improved adenoviral vectors, as well as novel strategies for generating and applying such vectors and a method for the intracellular amplification of linear DNA fragments in mammalian cells.

The so-called "minimal" adenoviral vectors according to the present invention retain at least a portion of the viral genome that is required for encapsulation of the genome into virus particles (the encapsulation signal), as well as at least one copy of at least a functional part or a derivative of the ITR, that is DNA sequences derived from the termini of the linear adenovirus genome. The vectors according to the present invention typically also contain a transgene linked to a promoter sequence to govern expression of the transgene. Packaging of the so-called minimal adenoviral vector can be achieved by co-infection with a helper virus or, alternatively, with a packaging deficient replicating helper system as described hereinafter.

Figure 13:
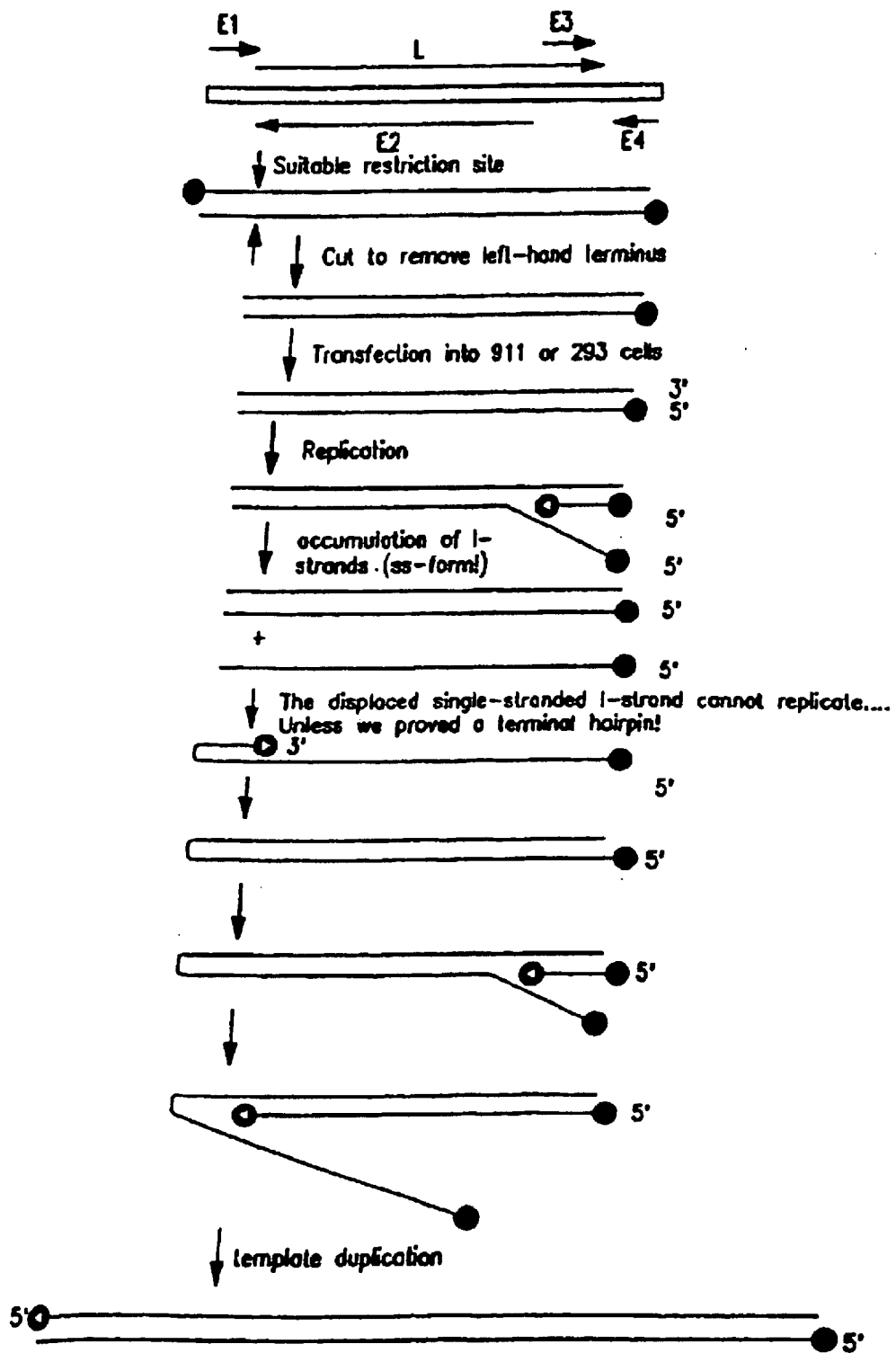
FIG. 13 depicts the rationale for the design of adenovirus-derived recombinant DNA molecules that duplicate and replicate in cells expressing adenovirus replication proteins. A diagram of the adenovirus double-stranded DNA genome indicating the approximate locations of E1, E2, E3, E4, and L regions is shown. The terminal polypeptide ("TP") attached to the 5'-termini is indicated by closed circles. The right arm of the adenovirus genome can be purified by removal of the left arm by restriction enzyme digestion. Following transfection of the right arm into 293 or 911 cells, adenoviral DNA polymerase (white arrow) encoded on the right arm, will produce only single-stranded forms. Neither the double-stranded or single-stranded DNA can replicate because they lack an ITR at one terminus. Providing the single-stranded DNA with a sequence that can form a hairpin structure at the 3'-terminus that can-serve as a substrate for DNA polymerase will extend the hairpin structure along the entire length of the molecule. This molecule can also serve as a substrate for a DNA polymerase but the product is a duplicated molecule with ITRs at both termini that can replicate in the presence of adenoviral proteins.
Figure 14:
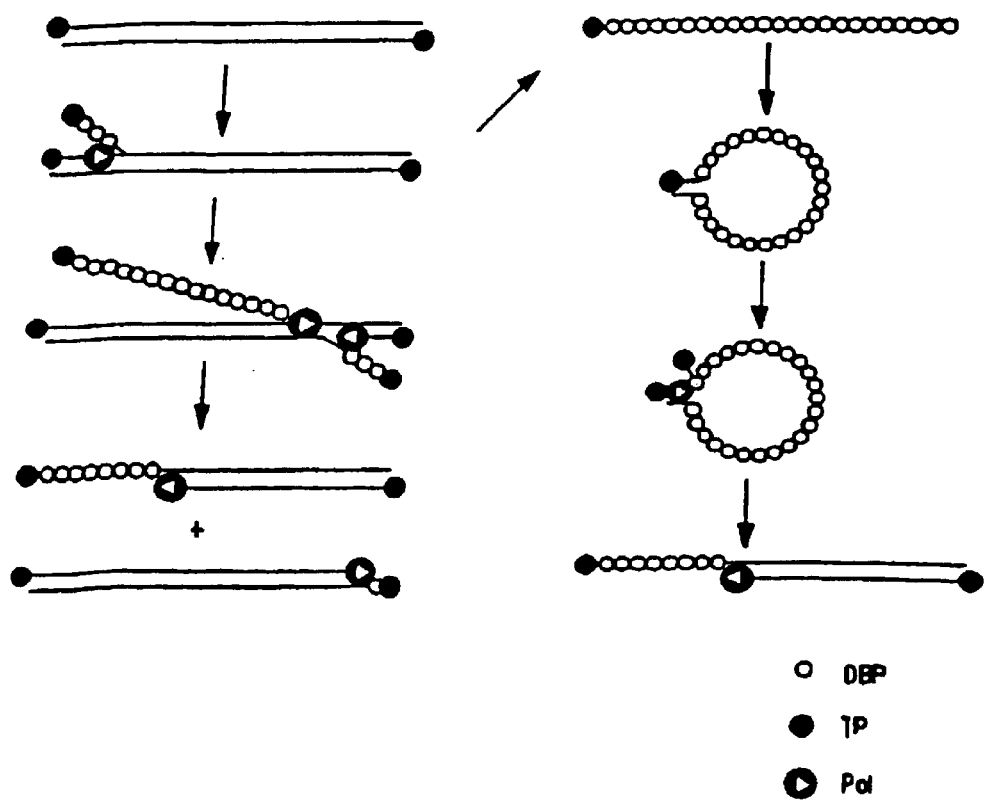
FIG. 14 depicts adenovirus genome replication. The adenovirus genome is shown in the top left. The origins of replication are located within the left and right ITRs at the genome ends. DNA replication occurs in two stages. Replication proceeds from one ITR generating a daughter duplex and a displaced parental single-strand which is coated with adenovirus DNA binding protein (DBP, open circles) and can form a panhandle structure by annealing of the ITR sequences at both termini. The panhandle is a substrate for DNA polymerase (Pol: white arrows) to produce double-stranded genomic DNA. Alternatively, replication proceeds from both ITRs, generating two daughter molecules, thereby, obviating the requirement for a panhandle structure.

Adenovirus-derived DNA fragments that can replicate in suitable cell lines and that may serve as a packaging deficient replicating helper system are generated as herein described. These DNA fragments retain at least a portion of the transcribed region of the "late" transcription unit of the adenovirus genome and carry deletions in at least a portion of the E1 region and deletions in at least a portion of the encapsulation signal. In addition, these DNA fragments contain at least one copy of an ITR. An ITR is located at one terminus of the transfected DNA molecule. The other end may contain an ITR, or alternatively, a DNA sequence that is complementary to a portion of the same strand of the DNA molecule other than the ITR. If, in the latter case, the two complementary sequences anneal, the free 3'-hydroxyl group of the 3'terminal nucleotide of the hairpin structure can serve as a primer for DNA synthesis by cellular and/or adenovirus-encoded DNA polymerases, resulting in conversion into a double-stranded form of at least a portion of the DNA molecule. Further replication initiating at the ITR will result in a linear double-stranded DNA molecule, that is flanked by two ITR's, and is larger than the original transfected DNA molecule (see, FIG. 13). This molecule can replicate itself in the transfected cell by virtue of the adenoviral proteins encoded by the DNA molecule and the adenoviral and cellular proteins encoded by genes in the host cell genome. This DNA molecule cannot be encapsulated due to its large size (greater than 39,000 bp) and/or due to the absence of a functional encapsulation signal. This DNA molecule is intended to serve as a helper for producing defective adenoviral vectors in suitable cell lines.

The invention also includes a method for amplifying linear DNA fragments of variable size in suitable mammalian cells. These DNA fragments contain at least one copy of the ITR at one terminus of the fragment. As described above, the other end may contain an ITR, or alternatively, a DNA sequence that is complementary to a portion of the same strand of the DNA molecule other than the ITR. If, in the latter case, the two complementary sequences anneal, the free 3'-hydroxyl group of the 3'terminal nucleotide of the hairpin-structure can serve as a primer for DNA synthesis by cellular and/or adenovirus-encoded DNA polymerases, resulting in conversion of the displaced strand into a double stranded form of at least a portion of the DNA molecule. Further replication initiation at the ITR will result in a linear double-stranded DNA molecule, that is flanked by two ITR's, which is larger than the original transfected DNA molecule. A DNA molecule that contains ITR sequences at both ends can replicate itself in transfected cells by virtue of the presence of at least the adenoviral E2 proteins (namely the DBP, the adenovirus DNA polymerase (Ad-pol), and the pre-terminal protein (pTP)). The required proteins may be expressed from adenoviral genes on the DNA molecule itself, from adenoviral E2 genes integrated in the host-cell genome, or from a replicating helper fragment as described above.

Several groups have shown that the presence of ITR sequences at the end of DNA molecules are sufficient to generate adenovirus minichromosomes that can replicate, if the adenovirus-proteins required for replication are provided in trans, for example, by infection with a helper virus (Hu et al., (1992) Gene 110:145–150); (Wang et al., (1985) in vivo. Nucl. Acids Res. 13:5173–5187); Hay et al., (1984) J. Mol. Biol. 174:493–510). Hu et al., (1992) Gene 110:145–150, observed the presence and replication of symmetrical adenovirus minichromosome-dimers after transfection of plasmids containing a single ITR. The authors were able to demonstrate that these dimeric minichromosomes arise after tail-to-tail ligation of the single ITR DNA molecules. In DNA extracted from defective adenovirus type 2 particles, dimeric molecules of various sizes have also been observed using electron-microscopy. Daniell J. Virol. 19:685–708 (1976). It was suggested that the incomplete genomes were formed by illegitimate recombination between different molecules and that variations in the position of the sequence at which the illegitimate base pairing occurred were responsible for the heterogeneous nature of the incomplete genomes. Based on this mechanism, it was speculated that, in theory, defective molecules with a total length of up to two times the normal genome could be generated. Such molecules could contain duplicated sequences from either end of the genome. However, no DNA molecules larger than the full-length virus were found packaged in the defective particles. Daniell J. Virol. 19:685–708 (1976). This can be explained by the size-limitations that apply to the packaging. In addition, it was observed that, in the virus particles, DNA-molecules with a duplicated left-end predominated over those containing the right-end terminus. Id. This is fully explained by the presence of the encapsulation signal near that left-end of the genome (Gräble et al., (1990) J. Virol. 64:2047–2056; Gräble et al., (1992) J. Virol. 66:723–731; Hearing et al., (1987) J. Virol. 61:2555–2558).

The major problems associated with the current adenovirus-derived vectors are:
a) The strong immunogenicity of the virus particle.
b) The expression of adenoviral genes that reside in the adenoviral vectors, resulting in a Cytotoxic T-cell response against the transduced cells.
c) The low amount of heterologous sequences that can be accommodated in the current vectors (up to maximally approx. 8000 bp. of heterologous DNA).
d) The poor frequency and poor reliability of the methods and means for generating new adenoviral vectors.

Ad A) The strong immunogenicity of the adenovirus particle results in a host immunological response, even after a single administration of the adenoviral vector. As a result of the development of neutralizing antibodies, a subsequent administration of the virus will be less effective or even completely ineffective. However, a prolonged or persistent expression of the transferred genes will reduce the number of administrations required and may bypass the problem.

Ad B) Experiments performed by Wilson and collaborators have demonstrated that after adenovirus-mediated gene transfer into immunocompetent animals, the expression of the transgene gradually decreases and disappears approximately 2–4 weeks post-infection (Yang et al., (1994a) Proc. Natl. Acad. Sci USA 91:4407–11; Yang et al., (1994b) Nat. Genet. 7:362–369). This is caused by the development of a cytotoxic T-cell ("CTL") response against the transduced cells. The CTLs were directed against adenoviral proteins expressed by the viral vectors. In the transduced cells, synthesis of the adenovirus DNA-binding protein (the E2A-gene product), penton and fiber proteins (late-gene products) could be established. These adenoviral proteins, encoded by the viral vector, were expressed despite deletion of the E1 region. This demonstrates that deletion of the E1 region is not sufficient to completely prevent expression of the viral genes (Engelhardt et al., (1994a) Human Gene Ther. 5:1217–1229).

Ad C) Studies by Graham and collaborators have demonstrated that adenoviruses are capable of encapsulating DNA of up to 105% of the normal genome size (Ben et al., (1993) J. Virol. 67:5911–5921). Larger genomes tend to be unstable resulting in loss of DNA sequences during propagation of the virus. Combining deletions in the E1 and E3 regions of the viral genomes increases the maximum size of the foreign that can be encapsulated to approx. 8.3 kb. In addition, some sequences of the E4 region appear to be dispensable for virus growth (adding another 1.8 kb to the maximum encapsulation capacity). Also, the E2A region can be deleted from the vector, when the E2A gene product is provided in trans in the encapsulation cell line, adding another 1.6 kb. It is, however, unlikely that the maximum capacity of foreign DNA can be significantly increased further than 12 kb.

We developed a new strategy for generating and producing helper-free stocks of recombinant adenoviral vectors that can accommodate up to 38 kb of foreign DNA. Only two functional ITR sequences, and sequences that can function as an encapsulation signal need to be part of the vector genome. Such vectors are called minimal adenovectors. The helper functions for the minimal adenovectors are provided in trans by encapsulation defective-replication competent DNA molecules that contain all the viral genes encoding the required gene products, with the exception of those genes that are present in the host-cell genome, or genes that reside in the vector genome.

Ad D) The generation of a new adenoviral vector with prior art means and methods may be possible. However, such means and methods are relatively inefficient in generating adenoviral vector and, moreover, in the process of generating the adenoviral vector, many other vectors or even RCA is produced necessitating a thorough and elaborate evaluation of the generated viruses. This is undesirable, especially for clinical settings, where he presence of RCA is extremely undesirable. In addition, specifically in settings where many different adenoviral vectors need to be generated (e.g., to produce expression libraries in adenoviral vectors, for instance, for use in high throughput screenings), the efficiency and the reliability of prior art adenoviral vector production systems remains insufficient. Reliability of adenoviral vector production is usually measured by determining, from a number of independent adenoviral vectors produced, the number of independent adenoviral vectors capable of functionally expressing a nucleic acid of interest or an analogous method capable of determining an analogous value. For instance, when the vector is not intended to express a nucleic acid of interest. Preferably, at least 80%, more preferably at least 90% and most preferably at least 95% of the adenoviral vectors produced by the method are functional vectors, and, when present in the vector, are capable of expressing the transgene and/or nucleic acid of interest.

Reliability of adenoviral vector production is desired especially in applications where many different adenoviral vectors need to be produced in a relatively short time span. A reliable system for producing adenoviral vectors then can significantly reduce the time and the costs involved. Preferably, the efficiency of adenoviral vector production for an average vector is greater than 1 independent vector produced per $10^6$ cells, more preferably the efficiency is more than 1 different vector produced $2 \times 10^5$ cells, most preferably the efficiency is more than 1 different vector produced $5 \times 10^4$ cells.

The applications of the disclosed inventions are outlined below and are illustrated in the Examples.

Use of the IG Packaging Constructs Diploid Cells

The constructs, in particular pIG.E1A.E1B, will be used to transfect diploid human cells, such as HER cells, HEK cells, and Human Embryonic Lung cells ("HEL"). Transfected cells will be selected for transformed phenotype (focus formation) and tested for their ability to support propagation of E1-deleted recombinant adenovirus, such as IG.Ad.MLPI.IK. Such cell lines will be used for the generating and (large-scale) producing E1-deleted recombinant adenoviruses. Such cells, infected with recombinant adenovirus, are also intended to be used in vivo as a local producer of recombinant adenovirus, for example, for the treatment of solid tumors. 911 cells are used for the titration, generation and production of recombinant adenoviral vectors (Fallaux et al., (1996) *Hum. Gene Ther.* 7:215–222).

HER cells transfected with pIG.E1A.E1B has resulted in 7 independent clones (called PER cells). These clones are used for producing E1-deleted (including non-overlapping adenoviral vectors) or E1-defective recombinant adenoviral vectors and provide the basis for introduction of, for example, E2B or E2A constructs (e.g., ts125E2A, see below), E4, etc., that will allow propagation of adenoviral vectors that have mutations in, for example, E2A or E4. In addition, diploid cells of other species that are permissive for human adenovirus, such as the cotton rat (*Sigmodon hispidus*) (Pacini et al., (1984) *J. Infect. Dis.* 150:92–97), Syrian hamster (Morin et al., (1987) *Proc. Natl. Acad. Sci. USA* 84:4626–4630) or chimpanzee (Levrero et al., (1991) *Gene* 101:195–202), will be immortalized with these constructs. Such cells, infected with recombinant adenovirus, are also intended to be used in vivo for the local production of recombinant adenovirus, for example, for the treatment of solid tumors.

Established Cells

The constructs, in particular pIG.E1A.NEO, can be used to transfect established cells, for example, A549 (human bronchial carcinoma), KB (oral carcinoma), MRC-5 (human diploid lung cell line) or GLC cell lines (small cell lung cancer) de Leij et al., (1985) *Cancer Res.* 45:6024–6033; Postmus et al., (1988) *Eur. J. Clin. Oncol.* 24:753–763) and selected for NEO resistance. Individual colonies of resistant cells are isolated and tested for their capacity to support propagation of E1-deleted recombinant adenovirus, such as IG.Ad.MLPI.TK. When propagation of E1-deleted viruses on E1A containing cells is possible, such cells can be used for generating and producing E1-deleted recombinant adenovirus. They are also used for the propagation of E1A deleted/E1B retained recombinant adenovirus.

Established cells can also be co-transfected with pIG.E1A.E1B and pIG.NEO (or another NEO containing expression vector). Clones resistant to G418 are tested for their ability to support propagation of E1-deleted recombinant adenovirus, such as IG.Ad.MLPI.TK and used for generating and producing E1-deleted recombinant adenovirus and will be applied in vivo for local production of recombinant virus, as described for the diploid cells (see, above).

All cell lines, including transformed diploid cell lines or NEO-resistant established lines, can be used as the basis for generating "next generation" packaging cell lines, that support propagation of E1-defective recombinant adenoviruses, that also carry deletions in other genes, such as E2A and E4. Moreover, they will provide the basis for generating minimal adenoviral vectors as disclosed herein.

E2 Expressing Cell Lines

Packaging cells expressing E2A sequences are used for the generation and (large scale) production of E2A-deleted recombinant adenovirus.

The newly generated human adenovirus packaging cell lines or cell lines derived from species permissive for human adenovirus (E2A or ts125E2A; E1A+E2A; E1A+E1B+E2A; E1A+E2A/ts 125; E1A+E1B+E2A/ts125) or non-permissive cell lines such as monkey cells (hrE2A or hr+ts125E2A; E1A+hrE2A; E1A+E1B+hrE2A; E1A+ hrE2A/ts125; E1A+E1B+hrE2A/ts 125) are used for the generation and (large scale) production of E2A deleted recombinant adenoviral vectors. In addition, they will be applied, in vivo, for local production of recombinant virus, as herein described for the diploid cells.

Novel Adenoviral Vectors

The newly developed adenoviral vectors harboring an E1 deletion of nt. 459–3510 will be used for gene transfer purposes. These vectors may also be the basis for the development of further deleted adenoviral vectors that are mutated for, for example, E2A, E2B or E4. Such vectors will be generated, for example, on the newly developed packaging cell lines herein described (see, 1–3).

Minimal Adenovirus Packaging System

We disclose adenovirus packaging constructs (to be used for the packaging of minimal adenoviral vectors) having the following characteristics:

a) The packaging construct replicates.
b) The packaging construct cannot be packaged because the packaging signal is deleted.
c) The packaging construct contains an internal hairpin-forming sequence (see, section "Experimental; suggested hairpin" see, FIG. 15).
d) Because of the internal hairpin structure, the packaging construct is duplicated, that is the DNA of the packaging construct becomes twice as long as it was before transfection into the packaging cell (in our sample it duplicates from 35 kb to 70 kb). This duplication also prevents packaging. Note that this duplicated DNA molecule has ITR's at both termini (see, e.g., FIG. 13).
e) This duplicated packaging molecule is able to replicate like a "normal adenovirus" DNA molecule.
f) The duplication of the genome is a prerequisite for producing sufficient levels of adenoviral proteins, required to package the minimal adenoviral vector.
g) The packaging construct has no overlapping sequences with the minimal vector or cellular sequences that may lead to generation of RCA by homologous recombination.

This packaging system will be used to produce minimal adenoviral vectors. The advantages of minimal adenoviral vectors, for example, for gene therapy of vaccination purposes, are well known (accommodation of up to 38 kb; "gutting" of all potentially toxic and immunogenic adenoviral genes).

Adenoviral vectors containing mutations in essential genes (including minimal adenoviral vectors) can also be propagated using this system.

Use of Intracellular E2-Expressing Vectors

Minimal adenoviral vectors are generated using the helper functions provided in trans by packaging-deficient replicating helper molecules. The adenovirus-derived ITR sequences serve as origins of DNA replication in the presence of at least the E2-gene products. When the E2 gene products are expressed from genes in the vector genome (N.B., the gene(s) must be driven by an E1-independent promoter), the vector genome can replicate in the target cells. This will allow a significantly increased number of template molecules in the target cells, and, as a result, an increased expression of the genes of interest encoded by the vector. This is of particular interest for approaches of gene therapy in cancer.

Applications of Intracellular Amplification of Linear DNA Fragments

A similar approach could also be taken if amplification of linear DNA fragments is desired. DNA fragments of known or unknown sequence could be amplified in cells containing the E2-gene products if at least one ITR sequence is located near or at its terminus. No apparent constraints exist on the size of the fragment. Even fragments much larger than the adenovirus genome (36 kb) could be amplified using this approach. It is thus possible to clone large fragments in mammalian cells without either shuttling the fragment into bacteria (such as $E.$ $coli$) or using die polymerase chain reaction ("PCR"). At the end stage of a productive adenoviral infection, a single cell can contain over 100,000 copies of the viral genome. In the optimal situation, the linear DNA fragments can be amplified to similar levels. Thus, one should be able to extract more than 5 jig of DNA fragment per 10 million cells (for a 35-kbp fragment). This system can be used to express heterologous proteins (equivalent to the Simian Virus 40-based COS-cell system) for research or for therapeutic purposes. In addition, the system can be used to identify genes in large fragments of DNA. Random DNA fragments may be amplified (after addition of ITRs) and expressed during intracellular amplification. Election or selection of those cells with the desired phenotype can be used to enrich the fragment of interest and to isolate the gene.

Gene Correction Vectors.

Gene therapy procedures may be divided into two different concepts, i.e., gene addition and gene replacement. Gene addition aims at introducing a therapeutic nucleic acid molecule into somatic cells of a patient, wherein expression of the therapeutic nucleic acid molecule is often under the control of a heterologous promoter and transcription termination signal. For example, when a patient suffers from an inherited disease, a functional copy of the defective nucleic acid molecule responsible for the disease phenotype is introduced into cells of the patient and, upon expression of the therapeutic nucleic acid molecule, the disease phenotype is corrected. Gene addition may also be used to accomplish expression of an otherwise not expressed gene, such as, for example, cytokine or suicide genes like Herpes Simplex Virus thymidine kinase (HSV-TK) to treat tumors. The gene replacement procedure aims at repairing at least one copy of a defective gene responsible for a disease phenotype. This can be achieved by introducing a functional version of a gene, or part thereof including the mutant site of that gene, in such a way that homologous recombination between the functional version and the defective gene occurs. Consequently, the defective gene or its mutant site is replaced by the functional version of that gene or part thereof. In this way, no nucleic acid-material that is foreign to the species of which the patient is a member is expressed in the treated cells, but at least one allele of the mutant gene is repaired. For the majority of the inherited diseases, it is known that heterozygous carriers are not affected, or at least are affected to a lesser extent than a homozygous patient. Thus, gene replacement may be used for correction of inherited disorders. It is to be understood that this also includes the repair of defective tumor suppressor genes.

For gene therapy purposes, it is preferable to retain the E3 region. E3-containing vectors will be superior to their E3-deleted counterparts because they are able to prevent or reduce host cells responses such as CTL lysis of adenovirus infected cells and cell lysis by TNF.

It will be understood that it may not be necessary to retain the whole E3 region in the vectors according to the invention, as long as the part retained still has the function of reducing the host response against infected cells. For example, expression of E3–14.7 kD alone may be sufficient to reduce early responses mediated by TNF (see, Ginsberg, H. S. (1989) $Proc.$ $Natl.$ $Acad.$ $Sci.$ $USA$ 86:3B23–3827;

Ginsberg, H. S. (1991) *Proc. Natl. Acad. Sci. USA* 88:1651–1655). These vectors are useful for gene therapy of inherited diseases such as cystic fibrosis, hypercholesterolemia, Duchenne molecular dystrophy, blood clotting disorders (hemophilia) and the like. They also are useful in the therapy of acquired diseases, such as tumors, hepatitis, (auto) immune diseases, restenosis, rheumatoid and the like.

Advantages of gene replacement over gene addition include (1) expression regulation of the replacing gene is identical to the endogenous expression pattern, and (2) the procedure is relatively safe, because no risk exists of insertion mutagenesis due to random integration.

A Recombinant Nucleic Acid Based System for Generating Adenoviral Vectors.

In one aspect, the invention provides a method for generating an adenoviral vector including welding together two nucleic acid molecules wherein the molecules include partially overlapping sequences capable of combining with each other allowing the generation of a physically linked nucleic acid including at least two functional adenoviral ITRs, a functional encapsulation signal and a nucleic acid of interest or functional parts, derivatives and/or analogues thereof. The nucleic acid molecules together include at least a left ITR, a right ITR and an adenoviral Encapsulation signal or functional parts, derivatives and/or analogues thereof. With overlapping sequences are meant sequences that include sufficient nucleic acid sequence similarity to allow homologous recombination. Sequence similarity is preferably more than 80% and more preferably more than 95%. With overlapping sequences are also meant complementary ends, of, for instance, a restriction enzyme site, wherein the nucleic acids are linked through hybridization of the complementary ends. The welding together may be performed through any means capable of physically linking two nucleic acid molecules. Preferably, the welding together is performed through linking complementary ends resulting from restriction enzyme digestion of the nucleic acid molecules. More preferably, the welding together is performed through homologous recombination of overlapping sequences in the nucleic acid.

In one embodiment, the invention provides a method for generating an adenoviral vector including welding together, through homologous recombination, two nucleic acid molecules including partially overlapping sequences wherein the overlapping sequences allow essentially only one homologous recombination which leads to the generation of a physically linked nucleic acid including at least two functional adenoviral ITRS, a functional encapsulation signal and a nucleic acid of interest or functional parts, derivatives and/or analogues thereof. Very important to this embodiment is that the partially overlapping sequences allow essentially only homologous recombination leading to the generation of a functional adenoviral vector capable of being replicated and packaged into adenovirus particles in the presence of the required transacting functions. With "essentially only one" is meant that the overlapping sequences in each nucleic acid include essentially only one continuous sequence whereby homologous recombination leading to the generation of a functional adenovirus may occur. Within the continuous sequence, the actual number of homologous recombination events may be greater than one. Non-continuous overlapping sequences are not desired because they reduce the reliability of the method. Non-continuous overlapping sequences are also not desired because they reduce the method's overall efficiency, presumably due to the generation of undesired homologous recombination products.

A preferred embodiment of the invention provides a method wherein both of the nucleic acid molecules include only one adenoviral ITR or a functional part, derivative, and/or analogue thereof.

In one aspect of the invention, one or both of the two nucleic acid molecules have undergone modifications prior to being welded together. The modification may include the welding together of different nucleic acid molecules leading to the generation of one or both of the two nucleic acid molecules. In a preferred embodiment, the different nucleic acids are welded together through homologous recombination of partially overlapping sequences.

In one aspect of the invention, the welding together is performed in a cell or a functional part, derivative, and/or analogue thereof. Preferably, the cell is a mammalian cell. In a preferred embodiment, the nucleic acid molecules are incapable of replicating in the mammalian cell prior to being welding together. Replication is undesired since it reduces the methods' reliability, presumably through providing additional targets for undesired homologous recombination. Replication is also not desired because it reduces the methods' efficiency presumably because replication competes for substrate or adenovirus transacting functions with the replication of the adenoviral vector.

In a preferred embodiment, one of the nucleic acid molecules is relatively small and the other is relatively large. This configuration is advantageous because it allows easy manipulation of the relatively small nucleic acid molecule allowing, for example, the generation of a large number of small nucleic acid molecules including different nucleic acids of interest, for instance, for generating an adenoviral vector library. This configuration is also desired because it allows for producing a large batch of quality tested, large nucleic acid molecules. The amplification of large nucleic acid molecules, for instance, in bacteria is difficult in terms of obtaining sufficient amounts of the large nucleic acid. The amplification of large nucleic acid molecules, for instance, in bacteria is also difficult to control because a small modification of the large nucleic acid is not easily detected. Moreover, for reasons not quite yet understood, some large vectors are more stable in bacteria or yeasts than others. This configuration, however, allows for generating a standard batch of a large nucleic acid molecule which can be thoroughly tested, for instance, through generating a control adenovirus of which the efficiency and the reliability of production is known, and determining the parameters of a new batch of large nucleic acid molecule. Once validated, the batch may be used for generating a large number of different adenoviral vectors through combining the large molecule with a large number of different small nucleic acid molecules. The system therefore also allows for the selection and/or manipulation of vectors including a large nucleic acid molecule of the invention to allow a suitable yield of intact large nucleic acid.

In one embodiment of the invention, at least one of the nucleic acid molecules includes an adenoviral ITR which, on one side, is essentially free of other nucleic acid. An on one side, essentially free adenoviral ITR is not essential for generating an adenoviral vector with a method or a means of the invention. However, an on one side, essentially free adenoviral ITR enhances the efficiency of adenoviral vector production as compared to not essentially free ITR. With "essentially free" is meant that the outwardly directed end of the ITR is essentially free of additional nucleic acid bases. Some additional bases do not significantly affect the generation of adenoviral vectors, particularly if the additional bases are not more than 50 bases, and preferably not more than 30 bases, and even more preferably not more than 10 bases. Preferably, both the left and right ITRs are made essentially free of other nucleic acids on the outwardly directed side. Preferably, the adenoviral ITR is made essentially free of other nucleic acid on one side through restriction enzyme digestion of a restriction enzyme site present near the adenoviral ITR. Preferably, the restriction enzyme site is not present anywhere else in the nucleic acid destined to be part of the adenoviral vector, in the nucleic acid molecule.

In one aspect, the invention provides a method for generating an adenoviral vector wherein the nucleic acids present in the cell do not include sequence overlap leading to the formation of RCA. Other systems for generating adenoviral vectors do not sufficiently suppress the generation of RCA upon the generation and/or the propagation of adenoviral vectors. In one aspect of the present invention, the generation of RCA is prevented through a system that prevents potential homologous recombination between, for instance, an E1-region and an adenoviral vector. Preventing the generation of RCA increases the reliability of adenovirus production, the desirability of the therapy in a clinical setting, and also increases the efficiency of adenoviral vector production.

One embodiment of the invention provides a method wherein the chromosomal nucleic acid in the cell includes at least a functional part of an adenoviral E1-region, or a functional derivative, and/or analogue thereof. Preferably, the cell is the previously identified PER.C6 cell, a functional derivative thereof, and/or an analogue thereof.

In another embodiment, the cellular nucleic acid further includes a nucleic acid encoding an adenoviral E2-region and/or an adenoviral E4-region protein.

In another embodiment, the invention provides a method or means for generating an adenoviral vector, wherein at least one of the nucleic acid molecules is linear. A linear molecule is not essential for adenoviral vector production, but adenoviral vector production efficiency is increased compared to when circular or supercoiled molecules are used.

In one embodiment, the invention provides a method wherein at least one of the molecules includes adenoviral capsid proteins encoding nucleic acid derived from at least two different adenovirus serotypes. This embodiment of the invention is useful for generating, for instance, an adenovirus particle with a chimeric capsid including proteins from at least two different adenovirus serotypes. One advantageous feature of a chimeric capsid is the capacity to alter the tissue tropism of an adenoviral vector. The capsid of an adenovirus particle is, among others, a major determinant of whether or not a particle is capable of entering a certain cell type (tissue tropism) and, by altering the capsid, the tissue tropism of an adenoviral vector can be altered and designed to meet specific needs. Preferably, the capsid includes at least a tissue tropism determining part of a fiber protein of a subgroup B-type adenovirus such as adenovirus 16 and at least one other capsid protein derived from a subgroup C-type adenovirus such as ad5. Preferably, the nucleic acid molecule including the adenoviral capsid protein encoding nucleic acid is a large nucleic acid molecule, thus enabling the easy generation of a library of adenoviral vectors packaged into the chimeric capsid.

In another embodiment, the invention provides a method wherein the welding together of the nucleic acid molecules leads to the generation of a physically linked nucleic acid including at least two functional adenoviral ITRs, a functional encapsulation signal, a nucleic acid encoding at least one adenoviral E1-region protein, at least one adenoviral E2-region encoded protein, and/or at least one adenoviral E4-region encoded protein and a nucleic acid of interest or functional parts, derivatives, and/or analogues thereof and wherein at least one of the E1-region encoded proteins is under transcriptional control of a conditionally active promoter. With a "conditionally active promoter" is meant a promoter active in certain cell types and inactive in other cell types. The method of this embodiment is particularly useful for generating a molecule capable of replicating in a cell provided that the conditionally active promoter is active in the cell. Such a molecule is useful, for instance, in vaccinations where very high expression of a transgene is required specifically in antigen presenting cells. When a vector of this embodiment is further provided with the capacity to express adenoviral capsid proteins, the vector capable of replicating is also capable of being packaged in a cell, so long as the conditionally active promoter is active in the cell, thus forming a conditional replication incompetent adenoviral vector.

In another embodiment, the invention provides a method wherein the physically linked nucleic acid includes no functional adenovirus nucleic acid other than two ITRs and a functional packaging signal or functional parts, derivatives, and/or analogues thereof, and wherein the physically linked nucleic acid is generated through the welding together of two nucleic acid molecules, the molecules including partially overlapping sequences capable of combining with each other allowing for the generation of the physically linked nucleic acid. The physically linked nucleic acid preferably further includes a nucleic acid of interest. This setting is favorable in that it allows the rapid generation of minimal adenoviral vectors through combining different, relatively small nucleic acid molecules including different nucleic acids of interest with one tested and validated large nucleic acid molecule.

The invention further provides a method for generating an adenoviral vector with a deletion of the E2A gene. This method includes providing a cell with the nucleic acid molecules, and growing the cell so that a first nucleic acid includes an adenoviral ITR and an encapsulation signal or functional parts, derivatives, and/or analogues thereof, and a partially overlapping sequence allowing it to be welded together with a second nucleic acid molecule including an adenoviral ITR or a functional part, derivative, and/or analogue thereof, a deletion of at least part of the E2A gene and a partially overlapping sequence, wherein the cell is capable of expressing functional E2A, preferably a temperature sensitive E2A. Both or either one of the nucleic acids may further include a nucleic acid of interest operatively linked to a transcription unit like a promoter and poly-adenylation signal or functional parts, derivatives and or analogues thereof. Welding together of the partially overlapping sequences may be achieved through any means so long as the means is capable of faithfully joining two strands of nucleic acid. Preferably, the partially overlapping sequences are welded together through one homologous recombination. In a preferred embodiment, at least all E2A sequences are deleted from the second nucleic acid thus preventing homologous recombination that abolishes the deletion of E2A in the second nucleic acid or derivatives thereof resulting from the welding together.

The invention further provides a method for generating RCAs with a deletion in the E3 region including providing a cell with nucleic acid molecules and growing the cell wherein a first nucleic acid includes an adenoviral ITR and encapsulation signal or functional parts, derivatives and/or analogues thereof, a conditionally functional E1 region, and a partially overlapping sequence allowing it to recombine with a second nucleic acid molecule including an adenoviral ITR or a functional part, derivative, and/or analogue thereof, a deletion in the E3 region and a partially overlapping sequence. Preferably, the second nucleic acid contains a nucleic acid of interest in the E3 region. More preferably, the nucleic acid of interest is operatively linked to the E3 promoter. The nucleic acid of interest may be a suicide gene, a cytokine, or a marker gene. The second nucleic acid molecule may be generated in the cell by homologous recombination of two partially overlapping smaller nucleic acid molecules, one of which includes the deletion in the E3 region with or without a nucleic acid of interest and only one of the smaller nucleic acid molecules contains an adenoviral ITR, preferably positioned on the end of one of the smaller nucleic acid molecules opposite of the partially overlapping sequence.

The invention further provides a method to generate adenoviral vectors with a modification in at least one of the late genes. This method includes providing a cell with nucleic acid molecules, and growing the cell so that a first nucleic acid molecule includes an adenoviral ITR and an encapsulation signal or functional parts, derivatives, and/or analogues thereof, and a partially overlapping sequence which allows it to recombine with a second nucleic acid molecule including an adenoviral ITR or a functional part, derivative, and/or analogue thereof, a modification in at least one of the late genes and a partially overlapping sequence. The modification in at least one of the late genes may include a modification in one of the capsid proteins, preferably penton, hexon, or fiber, or, more preferably, in more than one of the capsid proteins, more preferably in penton, hexon and fiber. The modification may be a change in the nucleotide sequence resulting from mutagenesis, deletion, insertion or combinations thereof, leading to a functional change of the adenoviral vector in, for example, immunogenicity, infectivity or stability. Preferably, the modification is a modification of the capsid genes generated by exchange of complete or part(s) of equivalent capsid genes from one or more different human or animal adenovirus serotypes, leading to a functional change of the adenoviral vector in, for example, immunogenicity, infectivity or stability. The second nucleic acid molecule may be generated in the cell by homologous recombination of two partially overlapping smaller nucleic acid molecules, at least one of which includes the modification in one or more capsid genes wherein only one of the smaller nucleic acid molecules contains an adenoviral ITR or a functional part, derivative, and/or analogue thereof, preferably positioned at the end of one of the smaller nucleic acid molecules opposite the partially overlapping sequence.

The invention further provides a recombinant nucleic acid deposited under accession No. P97082122 at the ECACC, a recombinant nucleic acid deposited under accession No. P97082119 at the ECACC, a recombinant nucleic acid deposited under accession No. P97082117 at the ECACC, a recombinant nucleic acid deposited under accession No. P97082114 at the ECACC, a recombinant nucleic acid deposited under accession No. P97082120 at the ECACC, a recombinant nucleic acid deposited under accession No. P97082121 at the ECACC, a recombinant nucleic acid deposited under accession No. P97082116 at the ECACC, a recombinant nucleic acid deposited under accession No. P97082115 at the ECACC, a recombinant nucleic acid deposited under accession No. P97082118 at the ECACC, and a recombinant nucleic acid pWE/Ad.AflII-EcoRI.

Figure 21:
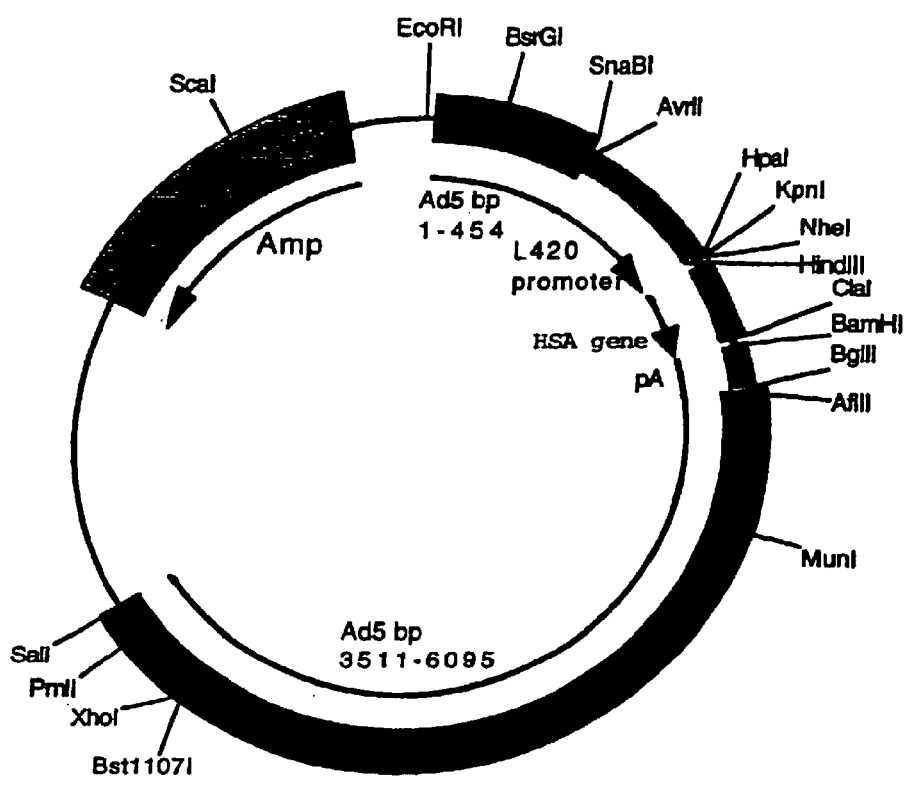
FIG. 21 is a drawing of adapter plasmid pAd/L420-HSA.
Figure 22:
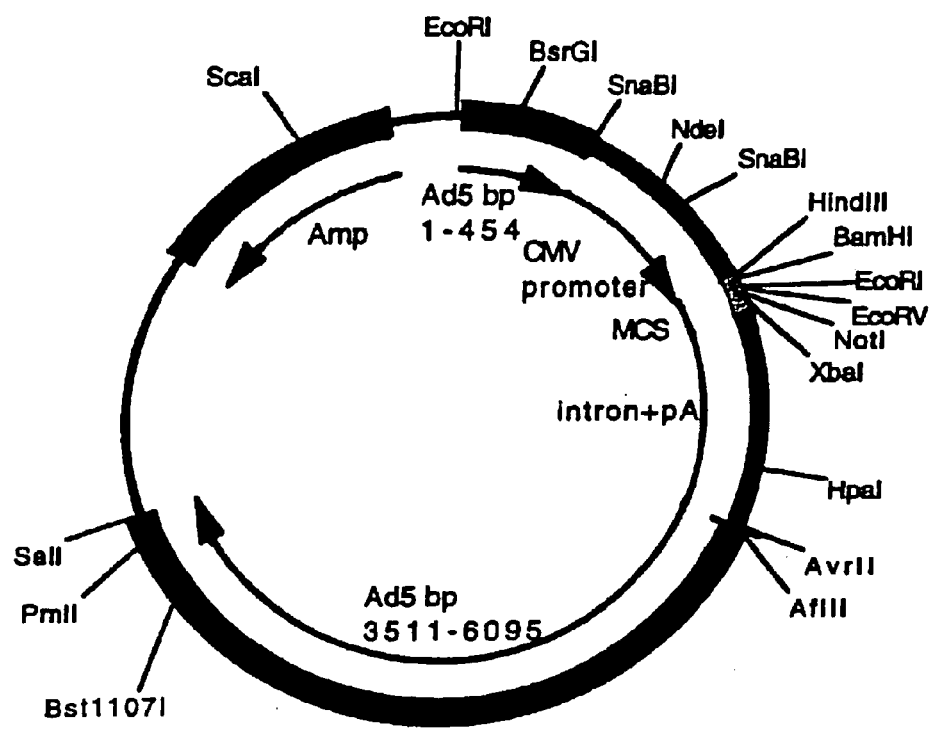
FIG. 22 is a drawing of adapter plasmid pAd/Clip.

The invention further provides a recombinant nucleic acid which includes adenovirus derived nucleotides 1–454 and adenovirus nucleotides 3511–6095 shown in FIGS. 21 and 22.

The invention further provides a recombinant nucleic acid pAd5/CLIP, a recombinant nucleic acid pAd5/L420-HSA, and a recombinant nucleic acid pBS.Eco-Eco/ad5ΔHIIIΔgp19KΔXbaI.

The invention further provides a recombinant nucleic acid wherein the nucleic acid further includes a transgene. This transgene may be operatively linked to an E3 promoter.

The invention further provides a recombinant nucleic acid wherein the transgene includes a suicide gene (e.g., HSV-TK gene), a cytokine gene, or a reporter gene.

The invention further provides a recombinant nucleic acid wherein the transgene includes a coding sequence selected from the group consisting of hIL-1α, rat IL-3, and human IL-3.

The invention further provides a recombinant nucleic acid wherein the transgene includes a coding sequence from a luciferase gene or a LacZ gene.

The invention further provides a recombinant nucleic acid wherein the transgene includes a coding sequence from a human ceNOS gene.

The invention further provides a recombinant nucleic acid including a deletion in an E3 region or the gp19K region of a recombinant nucleic acid.

The invention further provides a recombinant nucleic acid including a nucleotide sequence based on or derived from an adenovirus, wherein the nucleotide sequence includes a functional encapsulating signal, and two functional ITRs or functional fragments or derivatives thereof, and wherein the recombinant nucleic acid has no functional adenoviral genes and no overlapping sequences which allow for homologous recombination leading to replication competent virus in a cell into which the recombinant nucleic acid is transferred. Preferably, the recombinant nucleic acid, further including a heterologous nucleotide sequence.

The invention further provides a recombinant nucleic acid pMV/L420-H and a recombinant nucleic acid pMV/CMV-LacZ.

The invention further provides a recombinant nucleic acid which includes a nucleotide sequence, based on or derived from an adenovirus, wherein the nucleotide sequence includes sufficient adenovirus sequences necessary for replication and capsid gene expression, wherein the nucleotide sequence includes a deletion of at least the E1 region and encapsulating signal of the adenovirus, and wherein the nucleotide sequence includes no sequences which allow for homologous recombination leading to replication competent virus in a cell into which the recombinant nucleic acid is transferred.

The invention further provides a recombinant nucleic acid pWE/Ad.Δ5'.

The invention further provides a recombinant nucleic acid which includes a nucleotide sequence based on or derived from an adenovirus, wherein the nucleotide sequence includes sufficient adenovirus sequences necessary for replication and capsid gene expression, and a complementary sequence to an upstream part of the same strand of the nucleic acid, wherein the complementary sequence can base-pair with the upstream part so that it functions as a start-site for a nucleic acid polymerase, wherein the nucleotide sequence includes a deletion of one ITR, the E1 region and the encapsulating signal of the adenovirus, and wherein the nucleic acid has no overlapping sequence which allow for homologous recombination leading to replication competent virus in a cell into which the nucleic acid is transferred. Preferably, the molecule is pWE/AAV.Δ5'.

The invention further provides a recombinant nucleic acid which includes a nucleotide sequence, based on or derived from an adenovirus, wherein the nucleotide sequence includes a sequence for adenovirus-independent replication, and sufficient adenoviral sequences necessary for replication, wherein the nucleotide sequence includes at least a deletion of the E1 region and encapsulating signal of the adenovirus, and wherein the nucleic acid has no overlapping sequences which allow for homologous recombination leading to replication competent virus in a cell into which the nucleic acid is transferred. Preferably, the nucleotide sequence further includes a deletion of at least one of the ITRs of the adenovirus. Preferably, the sequence for adenovirus-independent replication includes an SV40 origin of replication.

The invention further provides a recombinant nucleic acid pWE/Ad-H.

The invention further provides an adapter plasmid which includes a nucleotide sequence, based on or derived from an adenovirus, wherein the nucleotide sequence includes in operable configuration at least one functional ITR, one functional encapsulating signal and adenoviral sequences which allow for homologous recombination and the generation of a replication-defective, recombinant adenovirus genome, and wherein the adapter plasmid has no sequences which allow for homologous recombination leading to replication competent virus in a cell into which the adapter plasmid is transferred. Preferably, the adapter plasmid includes no E1 region sequences. Preferably, the adapter plasmid further includes a multiple cloning site. Also preferred is an adapter plasmid according to the invention, further including a nucleic acid inserted into the multiple cloning site.

In another embodiment, the invention provides a method for generating recombinant adenovirus having an E1 deletion and a gp19K deletion, which includes the step of growing a cell including adenovirus complementing sequences transfected with i) an adapter plasmid including a first nucleotide sequence based on or derived from an adenovirus, wherein the nucleotide sequence includes in operable configuration one functional ITR, one functional encapsulating signal and adenoviral sequences which allow for homologous recombination leading to the generation of a replication-defective, recombinant adenovirus genome in a cell into which the adapter plasmid is transferred and having no E1 region sequences, and ii) a recombinant nucleic acid including at least one second nucleotide sequence based on or derived from an adenovirus, wherein the at least one second nucleotide sequence includes one ITR and sufficient adenovirus sequences for replication and a partial overlap with the adapter plasmid, wherein the at least one second nucleotide sequence includes a deletion of at least the E1 region, encapsulating signal and gp19K sequences; wherein the complementing sequences, the first nucleotide sequence and the at least one second nucleotide sequence have no overlapping sequences which allow for homologous recombination leading to replication competent virus, under conditions wherein recombinant adenovirus having an E1 deletion and a gp19K deletion is generated. Preferably, the adapter plasmid further includes a first heterologous nucleotide sequence inserted into the E1 region deletion and the recombinant nucleic acid further includes a second heterologous nucleotide sequence inserted into the gp19K region.

In another embodiment, the invention provides a method for generating recombinant adenovirus, including the step of growing a cell including adenovirus complementing sequences transfected with i) a first recombinant nucleic acid including a first nucleotide sequence based on or derived from an adenovirus, wherein the first nucleotide sequence includes a functional encapsulating signal and two functional ITRs or functional fragments or derivatives thereof, and wherein the first recombinant nucleic acid has no functional adenoviral genes and ii) a second recombinant nucleic acid including a second nucleotide sequence based on or derived from an adenovirus, wherein the second nucleotide sequence includes sufficient adenovirus sequences for replication, wherein the second nucleotide sequence includes a deletion of at least the E1 region and encapsulating signal of the adenovirus; wherein, the complementing sequences, the first nucleotide sequence and the second nucleotide sequence have no overlapping sequences which allow for homologous recombination leading to replication competent virus, under conditions wherein recombinant adenovirus is generated.

In another embodiment, the invention provides a method for generating recombinant adenovirus, including the steps of: growing a cell including adenovirus complementing sequences transfected with i) a first recombinant nucleic acid including a first nucleotide sequence based on or derived from an adenovirus, wherein the first nucleotide sequence includes a functional encapsulating signal and two functional ITRs or functional fragments or derivatives thereof, and wherein the first recombinant nucleic acid has no functional adenoviral genes and ii) a second recombinant nucleic acid including a second nucleotide sequence based on or derived from an adenovirus, wherein the second nucleotide sequence includes a sequence for adenovirus-independent replication, and sufficient adenoviral sequences necessary for replication, wherein the second nucleotide sequence includes at least a deletion of the E1 region and encapsulating signal of the adenovirus; wherein, the complementing sequences, the first nucleotide sequence and the second nucleotide sequence have no overlapping sequences which allow for homologous recombination leading to replication competent virus, under conditions wherein recombinant adenovirus is generated. Preferably, the cell includes at least one nucleic acid molecule wherein the cell expresses SV40 Large T antigen proteins or functional fragments thereof. More preferably, the second recombinant nucleic acid molecule is replicated.

In one embodiment the invention provides a replication defective adenovirus including: a genome based on or derived from an adenovirus, wherein the genome includes at least a functional encapsulating signal and two functional ITRs or functional fragments or derivatives thereof and wherein the genome includes no functional adenoviral genes and has no overlapping sequences which allow for homologous recombination leading to replication competent virus in a cell into which the replication defective adenovirus is transferred. Preferably, the replication defective adenovirus further includes one or more expression cassettes. Preferably, the expression cassette includes a gene functionally linked to transcription regulatory sequences.

In one embodiment, the replication defective adenovirus further includes one or more non-adenoviral nucleic acid sequences. Preferably, the one or more non-adenoviral nucleic acid sequences are inserted in the E1 region or in the E3 region gp19K gene.

In another aspect, the invention provides a non-human cell including a genome of a replication defective adenovirus according to the invention. Preferably, the cell is a mammalian cell.

In another aspect, the invention provides a method for transducing a cell, including the step of: contacting the cell with a replication defective adenovirus according to the invention under conditions wherein the cell is transduced.

In another aspect, the invention provides a non-human cell produced according to a method of the invention, preferably the cell is a mammalian cell.

In one embodiment, the invention provides a method for generating recombinant adenovirus including the step of: growing a cell including adenovirus complementing sequences and i) a first recombinant nucleic acid including a first nucleotide sequence based on or derived from an adenovirus, wherein the first nucleotide sequence includes a functional encapsulating signal and two functional ITRs or functional fragments or derivatives thereof, and wherein the first recombinant nucleic acid has no functional adenoviral genes and, ii) a second recombinant nucleic acid including a second nucleotide sequence based on or derived from an adenovirus, wherein the nucleotide sequence includes at least all adenovirus sequences, or functional fragments or derivatives thereof necessary for replication and capsid gene expression, and a complementary sequence to an upstream part of the same strand of the nucleic acid, wherein the complementary sequence can base-pair with the upstream part so that it functions as a start-site for a nucleic acid polymerase, wherein the second nucleotide sequence includes a deletion of one ITR, the E1 region and the encapsulating signal of the adenovirus; wherein, the complementing sequences, the first nucleotide sequence and the second nucleotide sequence have no overlapping sequences which allow for homologous recombination leading to replication competent virus, under conditions wherein recombinant adenovirus is generated.

In another aspect, the invention provides a cell including a recombinant nucleic acid and/or an adapter plasmid according to the invention.

In yet a further aspect, the invention provides a method for the replacement of a defective gene in a host cell genome including the step of growing the host cell with a recombinant nucleic acid molecule derived from a replication defective adenovirus including a functional version or part thereof of the defective gene under conditions wherein at least one allele of the defective gene in the host cell genome is replaced.

In one embodiment, the invention provides a method for transducing a cell according to the invention, wherein the replication defective adenovirus expresses no adenoviral genes. Preferably, the defective gene is a defective tumor suppressor gene.

The invention further provides an isolated cell including a genome of a replication-defective adenovirus according to the invention. Preferably, the cell is a human cell.

The invention further provides a recombinant nucleic acid according to the invention, wherein the deletion in the E3 region is replaced with a transgene.

The invention further provides a recombinant nucleic acid according to the invention, wherein the deletion in the gp19K region is replaced with a transgene.

The invention further provides a method wherein the at least one second nucleotide sequence includes a first and second molecule wherein the first molecule has the partial overlap with the adapter plasmid at the 3' end, and the second molecule includes the ITR and region including deletion of the gp19K sequences.

The invention further provides a replication-defective adenovirus including: a genome based on or derived from an adenovirus, wherein the genome includes a first deletion in the E1 region, and a second deletion in a gp19K region. Preferably, transcription of the transgene is directed by an E3 promoter.

The invention further provides an isolated cell including a recombinant nucleic acid and/or an adapter plasmid according to the invention. Preferably, the cell is a human cell.

The following examples are presented as illustrations, not limitations.

EXAMPLES

Example 1

Generation of Cell Lines Able to Transcomplement H1 Defective Recombinant Adenoviral Vectors 1. 911 cell line A cell line that harbors E1 sequences of Ad5, able to trans-complement E1-deleted recombinant adenovirus has been generated (Fallaux et al., (1996) *Hum. Gene Ther.* 7:215–222). This cell line was obtained by transfecting human diploid HER cells with pAd5XhoIC, that contains nt. 80–5788 of Ad 5; one of the resulting transformants was designated 911. This cell line has been shown to be useful in the propagation of E1 defective recombinant adenovirus. It was found to be superior to the 293 cells. Unlike 293 cells, 911 cells lack a fully transformed phenotype, which most likely is the cause of performing better as an adenovirus packaging line:

plaque assays can be performed faster (4–5 days instead of 8–14 days on 293) monolayers of 911 cells survive better under agar overlay as required for plaque assays higher amplification of E1-deleted vectors.

In addition, unlike 293 cells that were transfected with sheared adenoviral DNA, 911 cells were transfected using a defined construct. Transfection efficiencies of 911 cells are comparable to those of 293.

New Packaging Constructs

Source of Adenovirus Sequences

Adenovirus sequences are derived either from pAd5.SalB containing nt. 80–9460 of human Ad5 (Bernards et al., (1983) *Virology* 127:45–53) or from wild-type Ad5 DNA. PAd5.SalB was digested with SalI and XhoI and the large fragment was re-ligated and this new clone was named pAd5.X/S. The pTN construct (constructed by Dr. R. Vogels, IntroGene, The Netherlands) was used as a source for the human PGK promoter and the NEO gene.

Human PGK Promoter and $NEO^R$ Gene

Transcription of E1A sequences in the new packaging constructs is driven by the human PGK promoter (Michelson et al., (1983) *Proc. Natl. Acad. Sci. USA* 80:472–476); Singer-Sam et al., (1984) *Gene* 32:409–417), derived from plasmid pTN (gift of R. Vogels), which uses pUC 119 (Vieira et al., (1987) pp. 3–11: *Methods in Enzymology*, Acad. Press Inc.) as a backbone. This plasmid was also used as a source for the NEO gene fused to the HBV poly-adenylation signal.

Fusion of PGK Promoter to E1 Genes (FIG. 1)

In order to replace the E1 sequences of Ad5 (ITR, origin of replication and packaging signal) by heterologous sequences we have amplified E1 sequences (nt. 459 to nt. 960) of Ad5 by PCR, using primers Ea1 and Ea2 (see, Table 1). The resulting PCR product was digested with ClaI and ligated into Bluescript (Stratagene), predigested with ClaI and EcoRV resulting in construct pBS.PCRI.

Vector pTN was digested with restriction enzymes EcoRI (partially) and ScaI, and the DNA fragment containing the PGK promoter sequences was ligated into PBS.PCRI digested with ScaI and EcoRI. The resulting construct PBS.PGK.PCRI contains the human PGK promoter operatively linked to Ad5 E1 sequences from nt. 459 to nt. 916.

Figure 2:
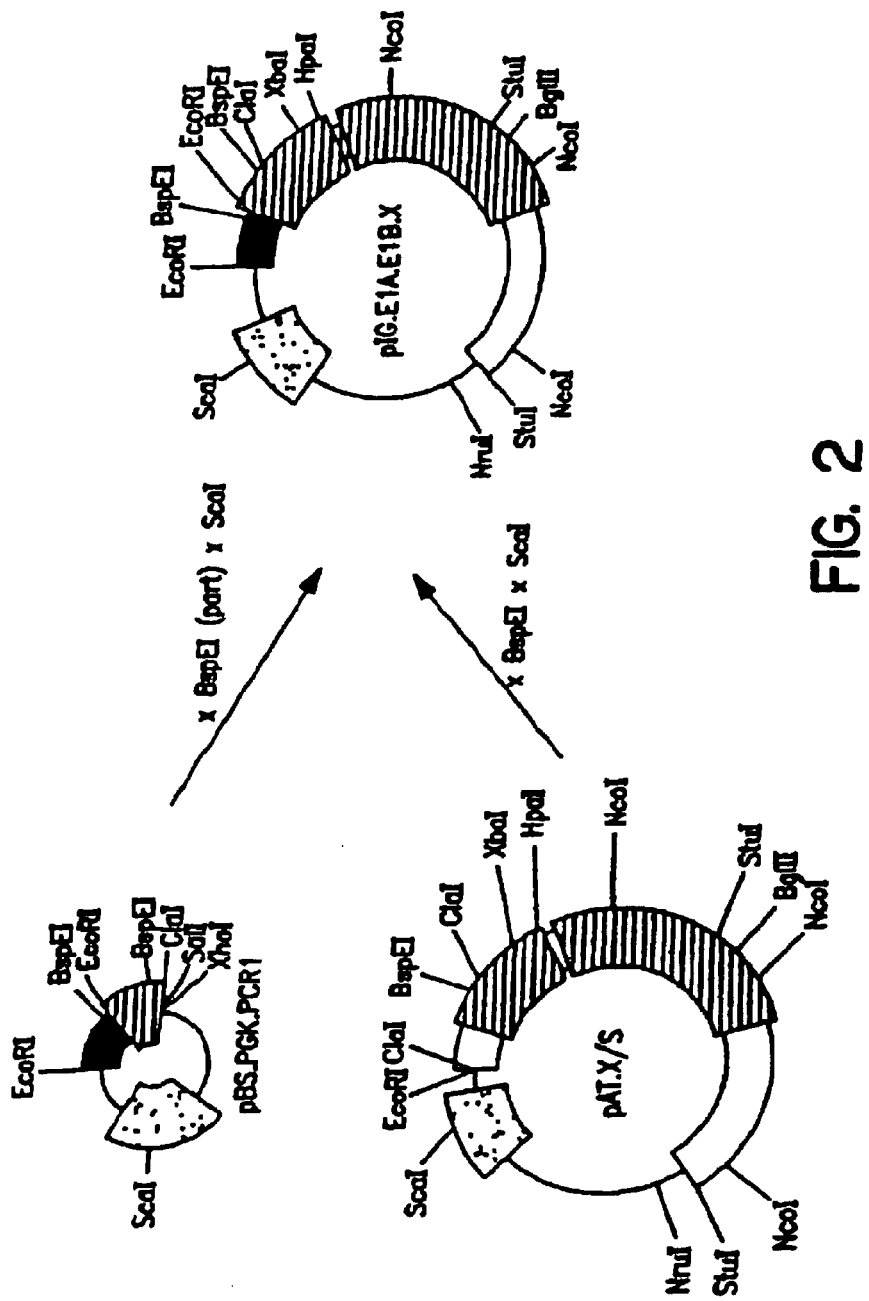
FIG. 2 depicts the construction of pIG.E1A.E1B.X. pIG.E1A.E1B.X encodes Ad5 nucleotides 459–5788 (E1A and E1B regions) operatively linked to the human PGK promoter. pIG.E1A.E1B.X also encodes Ad5 pIX protein. pIG.E1A.E1B.X was constructed by replacing the Sca I-BspE I fragment of pAT-X/S with the corresponding fragment of pBS.PGK.PCRI.

Construction of pIG.E1A.E1B (FIG. 2)

pIG.E1A.E1B.X contains the E1A and E1 B coding sequences under the direction of the PGK promoter. As Ad5 sequences from nt. 459 to nt. 5788 are present in this construct, also pIX protein of adenovirus is encoded by this plasmid. pIG.E1A.E1B.X was made by replacing the ScaI-BspEI fragment of pAT-X/S by the corresponding fragment from PBS.PGK.PCRI (containing the PGK promoter linked to E1A sequences).

Figure 3A:
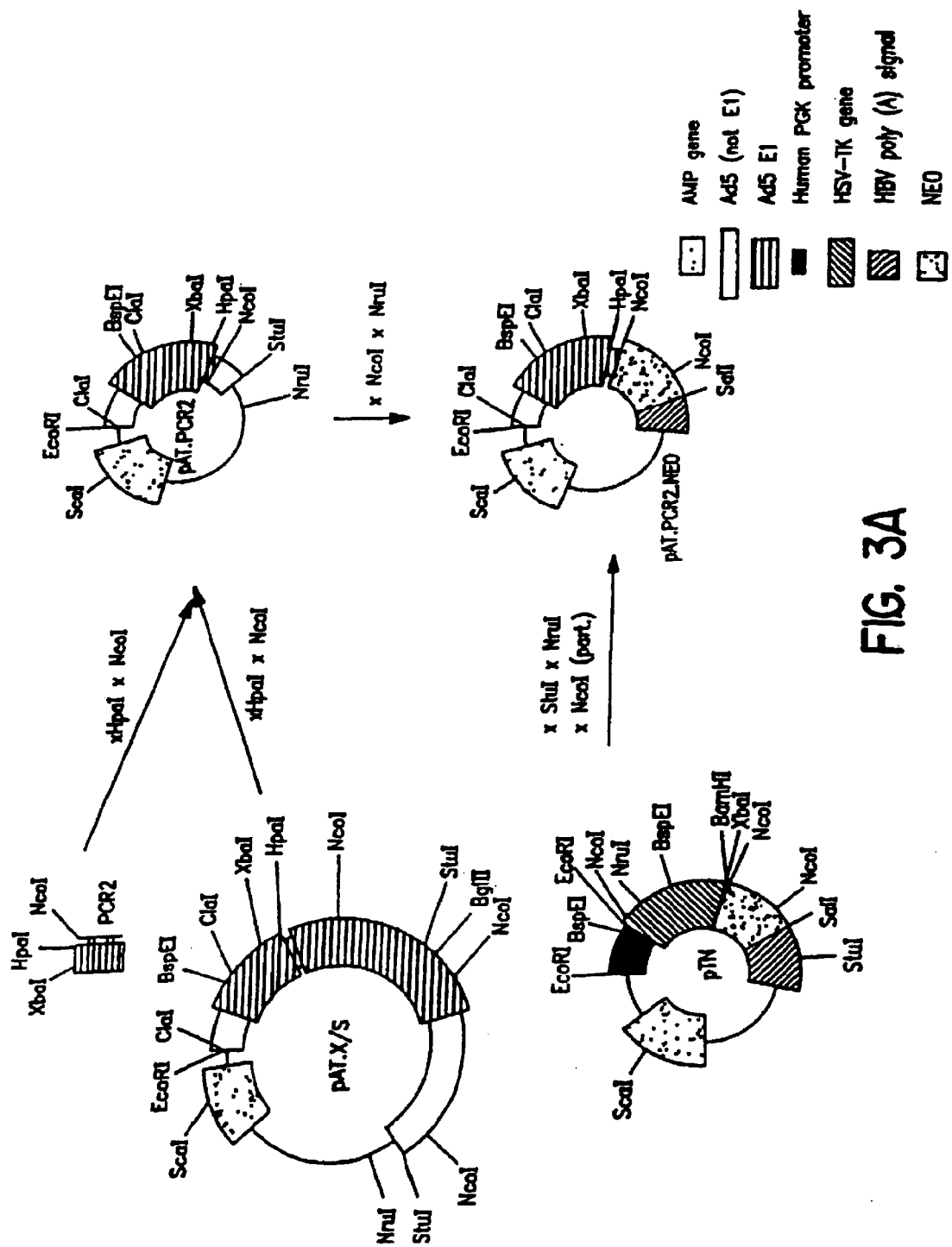
FIG. 3 depicts the construction of pIG.E1A.NEO. pIG.E1A.NEO encodes Ad5 nucleotides 459–1713 operatively linked to the human PGK promoter. Also encoded is the E1B promoter functionally linked to the neomycin resistance gene ($Neo^R$) and the hepatitis B virus ("HBV") poly(A) signal. In this construct, the AUG codon of the E1B 21 kDa protein functions as the initiation codon of $Neo^R$. To construct this plasmid, the E1B promoter and initiation codon (ATG) of the E1B 21 kDa protein were PCR amplified with primers Ea-3 and Ep-2, where Ep-2 introduces an Nco I site (5'-CCATGG) at the 21 kDa protein initiation codon. The PCR product (PCII) was digested with Hpa I and Nco I and ligated into the corresponding sites of pAT-X/S, producing pAT-X/S-PCR2. The Nco I-Stu I fragment of pTN, containing the $Neo^R$ and a portion of the HBV poly(A) site were ligated into the Nco 1-Nru I sites of pAT-X/S-PCR2, producing pAT-PCR2-NEO. The HBV poly(A) signal was completed by replacing the Sca 1-Sal I fragment of pAT-PCR2-NEO with the corresponding fragment of pTN, producing pAT.PCR2.NEO.p(A), and replacing the Sca I-Xba I fragment of pAT.PCR2.NEO.p(A) with the corresponding fragment of pIG.E1A.E1B.X, producing pIG.E1A.NEO.
Figure 3B:
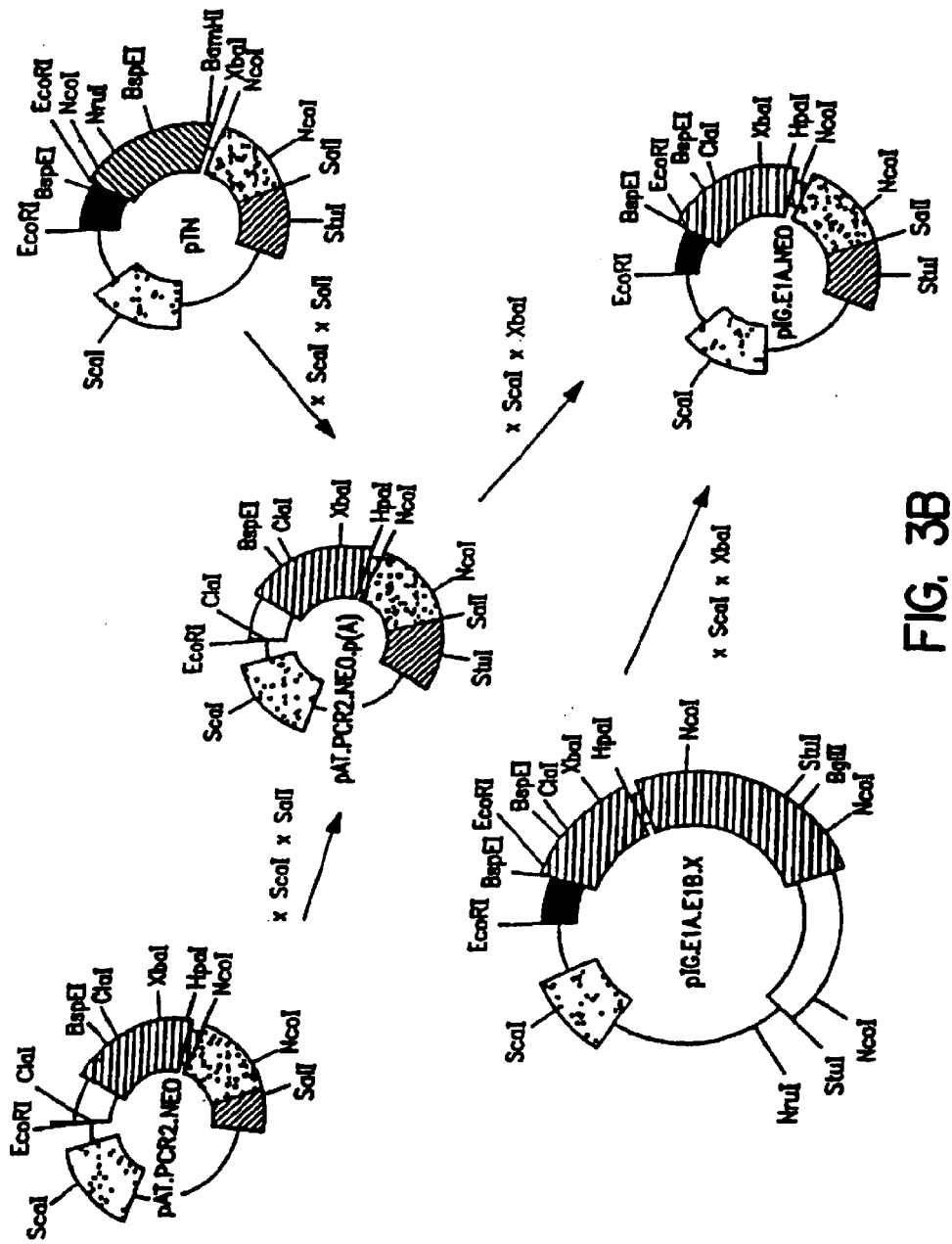

Construction of pIG.E1A.NEO (FIG. 3)

In order to introduce the complete E1B promoter and to fuse this promoter in such a way that the AUG codon of E1B 21 kD exactly functions as the AUG codon of NEO$^R$, the EIB promoter was amplified using primers Ea3 and Ep2, where primer Ep2 introduces a NcoI site in the PCR fragment. The resulting PCR fragment, named PCRII, was digested with HpaI and NcoI and ligated into pAT-X/S, which was predigested with HpaI and with NcoI. The resulting plasmid was designated pAT-X/S-PCR2. The NcoI-StuI fragment of pTN, containing the NEO gene and part of the HBV poly-adenylation signal, was cloned into pAT-X/SPCR2 which had been digested with NcoI and NruI). The resulting construct was pAT.PCR2.NEO. The poly-adenylation signal was completed by replacing the ScaI-SalI fragment of pAT. PCR2.NEO with the corresponding fragment of pTN, resulting in pAT.PCR2.NEO.p(A). The ScaI-XbaI of pAT.PCR2.NEO.p(A) was replaced with the corresponding fragment of pIG.E1A.E1B-X, containing the PGK promoter linked to E1A genes. The resulting construct was named pIG.E1A.NEO, and thus contains Ad5 E1 sequences (nt. 459 to nt. 1713) under the control of the human PGK promoter.

Figure 4:
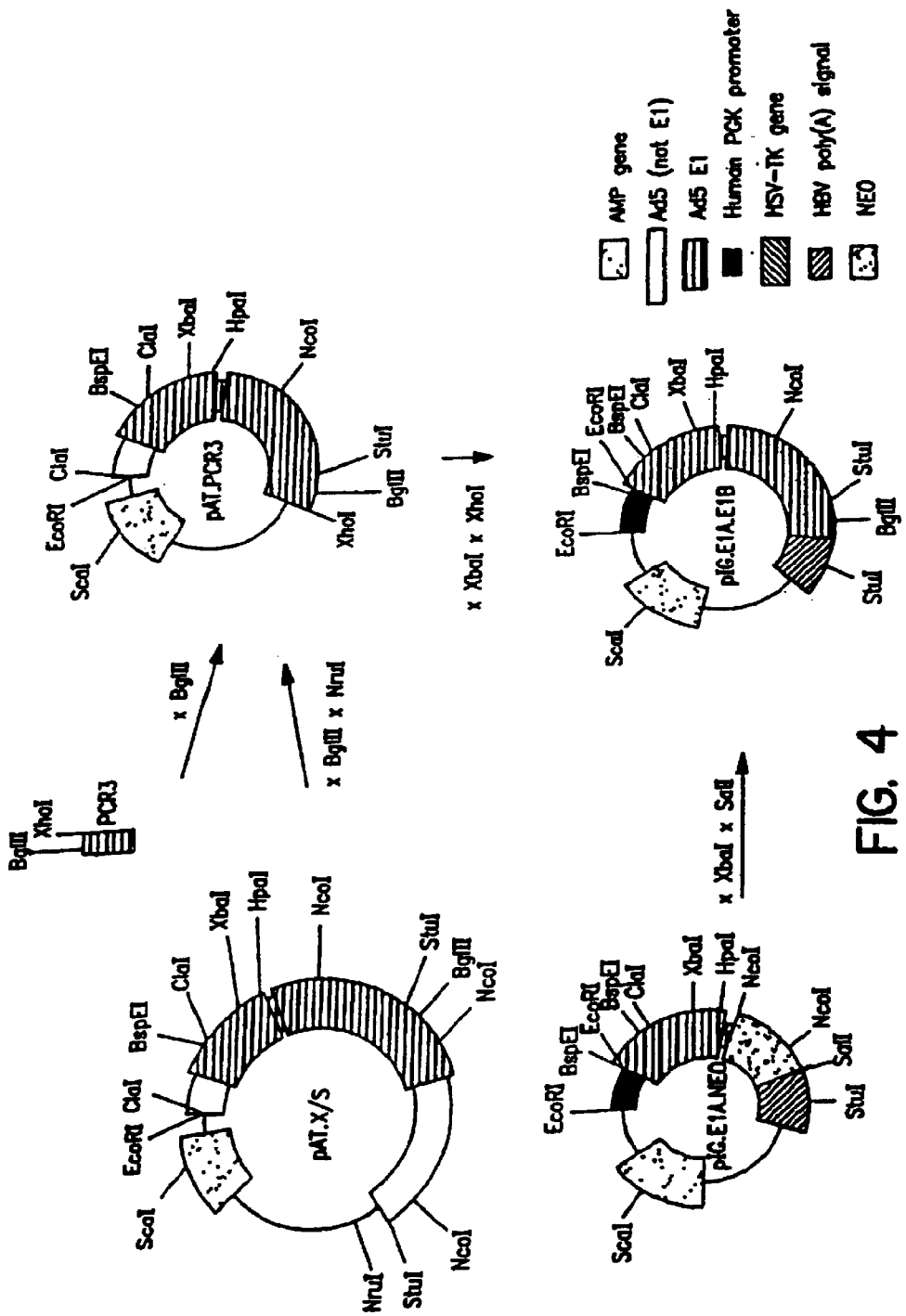
FIG. 4 depicts the construction of pIG.E1A.E1B. pIG.E1A.E1B contains the Ad5 nucleotides 459–3510 (E1A and E1B proteins) operatively linked to the PGK promoter and HBV poly(A) signal. This plasmid was constructed by PCR amplification of the N-terminal amino acids of the E1B 55 kD protein with primers Eb-1 and Eb-2, which introduces an Xho I site, digested with Bgl II and cloned into the Bgl II-Nru I sites of pAT-X/S, producing pAT-PCR3. The Xba I-Xho I fragment of pAT-PCR3 was replaced with the Xba I-Sal I fragment (containing the HBV poly(A) site) of pIG.E1A.NEO to produce pIG.E1A.E1B.

Construction of pIG.E1A.E1B (FIG. 4)

pIG.E1A.E1B contains nt. 459 to nt. 3510 of Ad5, that encode the E1A and E1B proteins. The E1B sequences are terminated at the splice acceptor at nt. 3511. No pIX sequences are present in this construct.

pIG.E1A.E1B was made as follows: The sequences encoding the N-terminal amino acids of E1B 55 kD were amplified using primers Eb1 and Eb2 which introduces a XhoI site. The resulting PCR fragment was digested with BglII and cloned into BglII/NruI of pAT-X/S, thereby obtaining pAT-PCR3. The HBV poly (A) sequences of pIG.E1A.NEO were introduced downstream of the E1B sequences of pAT-PCR3 by exchange of the Xba-SalI fragment of pIG.E1A.NEO and the XbaI XhoI fragment of pAT.PCR3.

Figure 5:
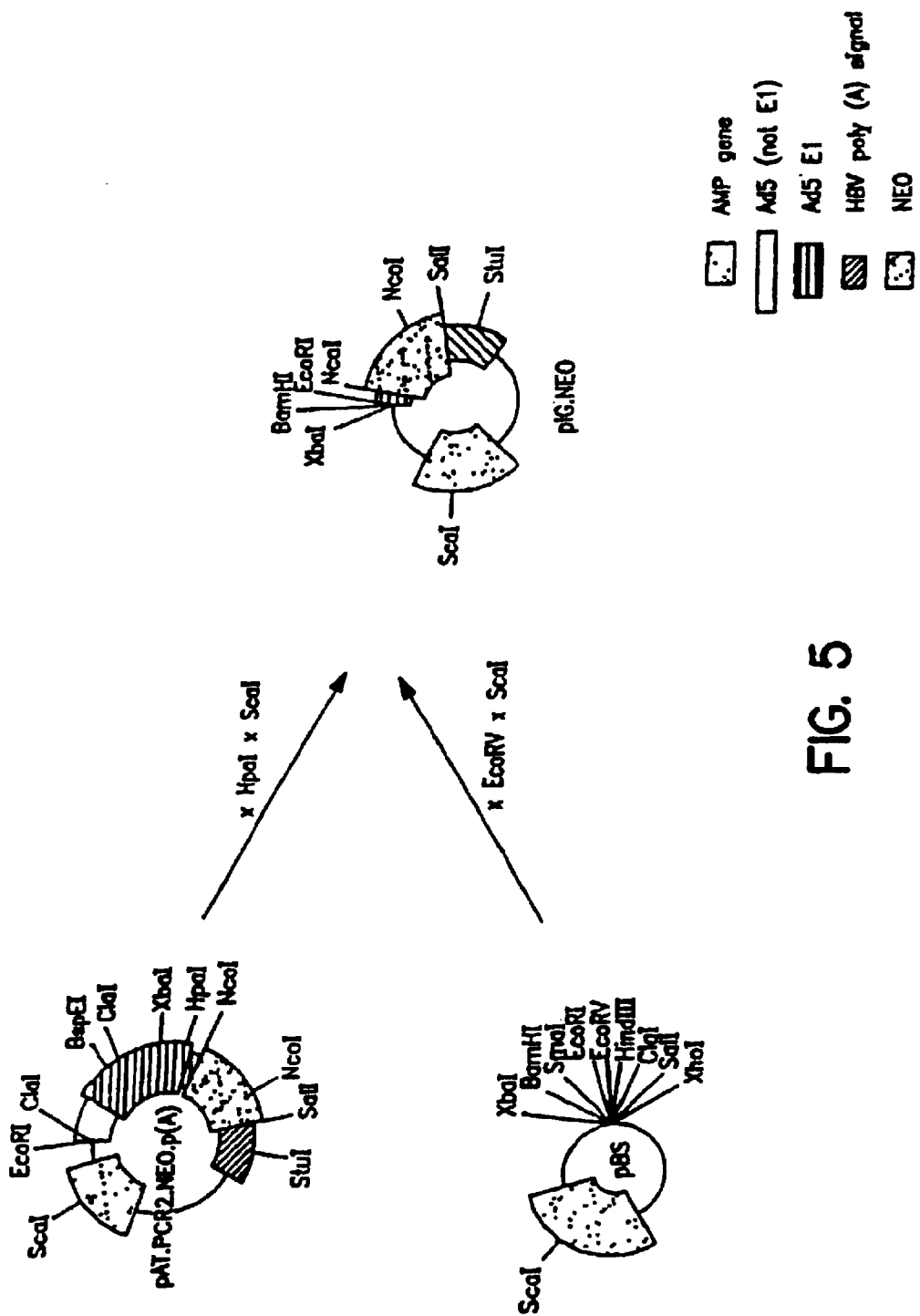
FIG. 5 depicts the construction of pIG.NEO. pIG.NEO contains the $NEO^R$ operatively linked to the E1B promoter. pIG.NEO was constructed by ligating the Hpa I-Sca I fragment of pIG.E1A.NEO which contains the E1B promoter and $Neo^R$ into the EcoR V-Sca I sites of pBS.

Construction of pIG.NEO (FIG. 5)

This construct is of use when established cells are transfected with EIA.E1B constructs, and NEO selection is required. Because NEO expression is directed by the E1B promoter, NEO resistant cells are expected to co-express E1A, which is also advantageous for maintaining high levels of expression of E1A during long-term culture of the cells. pIG.NEO was generated by cloning the HpaI-ScaI fragment of pIG.E1A.NEO, containing the NEO gene under the control of the Ad5 E1B promoter, into pBS digested with EcoRV and ScaI.

Testing of Constructs

The integrity of the constructs pIG.E1A.NEO, pIG.E1A.E1B.X and pIG.E1A.E1B was assessed by restriction enzyme mapping. Furthermore, parts of the constructs that were obtained by PCR analysis were confirmed by sequence analysis. No changes in the nucleotide sequence were found.

The constructs were transfected into primary BRK (Baby Rat Kidney) cells and tested for their ability to immortalize (pIG.E1A.NEO) or fully transform (pAd5.XhoIC, pIG.E1A.E1B.X and pIG.E1A.E1B) these cells. Kidneys of 6-day old WAG-Rij rats were isolated, homogenized and trypsinized. Subconfluent dishes (diameter 5 cm) of the BRK cell cultures were transfected with 1 or 5 µg of pIG.NEO, pIG.E1A.NEO, pIG.E1A.E1B, pIG/E1A.E1B.X, pAd5XhiIC, or with pIG.E1A.NEO together with PDC26 (Elsen et al., (1983) *Virology* 128:377–390), carrying the Ad5.E1B gene under control of the SV40 early promoter. Three weeks post-transfection, when foci were visible, the dishes were fixed, Giemsa stained and the foci counted.

Figure 6:
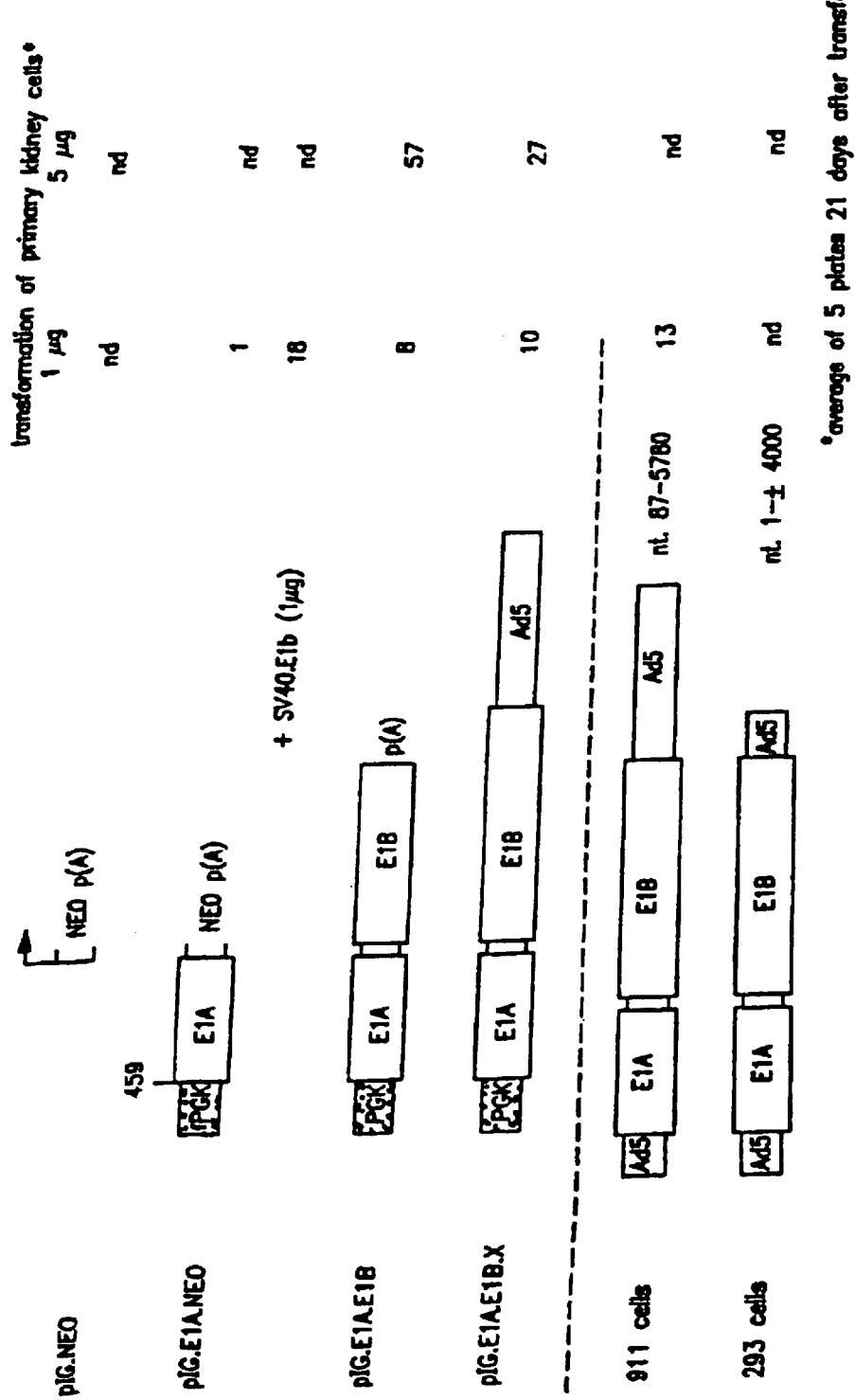
FIG. 6 is a graphical overview of available adenovirus packaging cells assessing their capacity to transform primary kidney cells. It generally depicts the transformation of primary baby rat kidney cells by adenovirus packaging constructs. Sub-confluent dishes of BRK cells were transfected with 1 or 5 µg of with either pIG.NEO, pIG.E1A.NEO, pIG.E1A.E1B, pIG.E1A.E1B.X, pAd5XhoIC, or pIG.E1A.NEO plus pDC26, which expresses the Ad5 E1B gene under control of the SV40 early promoter. Three weeks post-transfection, foci were visible, cells were fixed, Giemsa stained and the foci counted. The results shown are the average number of foci per 5 replicate dishes.

An overview of the generated adenovirus packaging constructs, and their ability to transform BRK, is presented in FIG. 6. The results indicate that the constructs pIG.E1A.E1B and pIG.E1A.E1B.X are able to transform BRK cells in a dose-dependent manner. The efficiency of transformation is similar for both constructs and is comparable to what was found with the construct that was used to make 911 cells, namely pAd5.XhoIC.

As expected, pIG.E1A.NEO was hardly able to immortalize BRK. However, co-transfection of an E1B expression construct (PDC26) did result in a significant increase of the number of transformants (18 versus 1), indicating that the E1A encoded by pIG.E1A.NEO is functional. We conclude therefore, that the newly generated packaging constructs are suitable for generating new adenovirus packaging lines.

Generation of Cell Lines with New Packaging Constructs Cell Lines and Cell Culture Human A549 bronchial carcinoma cells (Shapiro et al., (1978) *Biochem. Biophys. Acta* 530:197–207), HER cells, Ad5-E1-transformed HEK cells (293; Graham et al., (1977) *J. Gen. Virol.* 36:59–72) and Ad5-transformed HER cells (911; Fallaux et al., (1996), *Hum. Gene Ther.* 7:215–222) and PER cells were grown in Dulbecco's Modified Eagle Medium (DMEM) supplemented with 10% Fetal Calf Serum (FCS) and antibiotics in a 5% CO2 atmosphere at 37° C. Cell culture media, reagents and sera were purchased from Gibco Laboratories (Grand Island, N.Y.). Culture plastics were purchased from Greiner (Nürtingen, Germany) and Corning (Cooring, N.Y.).

Viruses and Virus Techniques

The construction of recombinant adenoviral vectors IG.Ad.MLP.nls.lacZ, IG.Ad.NILP.luc, IG.Ad.MLP.TK and IG.Ad.CW.TK is described in detail in EPO patent application EP 95202213. The recombinant adenoviral vector IG.Ad.MIP.nls.lacZ contains the *E. coli* lacZ gene, encoding β-galactosidase, under control of the Ad2 major late promoter (MLP), IG.Ad.MLP.luc contains the firefly luciferase gene driven by the Ad2 MLP, and adenoviral vectors IG.Ad.NLP.TK and IG.Ad.CMV.TK contain the HSV-TK gene under the control of the Ad2 MLP and the Cytomegalovirus (CMV) enhancer/promoter, respectively.

Transfections

All transfections were performed by calcium-phosphate precipitation DNA (Graham et al., (1973) *Virology* 52:456–467) with the GIBCO Calcium Phosphate Transfection System (GEBCO BRL Life Technologies, Inc., Gaithersburg, USA), according to the manufacturer's protocol.

Western Blotting

Subconfluent cultures of exponentially growing 293, 911 and Ad5-E1-transformed A549 and PER cells were washed with PBS and scraped in Fos-RIPA buffer (10 mM Tris (pH 7,5), 150 mM NaCl, 1% NP40,01% sodium dodecyl sulfate (SDS), 1% NA-DOC, 0.5 mm phenyl methyl sulfonyl fluoride (PMSF), 0.5 mM trypsin inhibitor, 50 mM NaF and 1 mM sodium vanadate). After 10 min. at room temperature, lysates were cleared by centrifugation. Protein concentrations were measured with the BioRad protein assay kit and 25 µg total cellular protein was loaded on a 12.5% SDS-PAA gel. After electrophoresis, proteins were transferred to nitrocellulose (1 h at 300 mA). Pre-stained standards (Sigma, USA) were run in parallel. Filters were blocked with 1% bovine serum albumin (BSA) in TBST (10 mM Tris, pH 8.15 mM NaCl, and 0.05t Tween-20) for 1 hour. First antibodies were the mouse monoclonal anti-Ad5-E1B-55-kDA antibody A1C6 (Zantema et al., unpublished), the rat monoclonal anti-Ad5-EIB-221-kDa antibody C1G11 (Zantema et al., (1985) Virology 142:44–58). The second antibody was a horseradish peroxidase-labeled goat anti-mouse antibody (Promega). Signals were visualized by enhanced chemolumines-cence (Amersham Corp. UK).

Southern Blot Analysis

High molecular weight DNA was isolated and 10 µg were digested to completion and fractionated on a 0.7% agarose gel. Southern blot transfer to Hybond N+ (Amersham, UK) was performed with a 0.4 M NaOH, 0.6 M NaCl transfer solution (Church and Gilbert, 1984). Hybridization was performed with a 2463-nt SspI-HindIII fragment from pAd5.SalB (Bernards et al., (1983) Virology 127:45–53). This fragment consists of Ad5 bp. 342–2805. The fragment was radio labeled with a, $\alpha^{-32}P$=dCTP with the use of random hexanucleotide primers and Klenow DNA polymerase. The southern blots were exposed to a Kodak XAR-5 film at −80° C. and to a Phosphor-Imager screen which was analyzed by B&L systems Molecular Dynamics Software.

A549

Ad5-E1-transformed A549 human bronchial carcinoma cell lines were generated by transfection with pIG.E1A.NEO and selection for G418 resistance. Thirty-one G418 resistant clones were established. Co-transfection of pIG.E1A.E1B with pIG.NEO yielded seven G418 resistant cell lines.

PER

Ad5-E1-transformed human embryonic retina (HER) cells were generated by transfection of primary HER cells with plasmid pIG.E1A.E1B. Transformed cell lines were established from well-separated foci. Seven clonal cell lines were established, which we called PER.C1, PER.C3, PER.C4, PER.C5, PER.C6, PER.C8 and PER.C9. One of the PER clones, namely PER.C6, has been deposited at the ECACC under number 96022940.

Expression of Ad5 E1A and E1B Genes in Transformed A549 and PER Cells

Expression of the Ad5 E1A and the 55-kDa and 21 kDa E1B proteins in the established A549 and PER cells was studied by means of Western blotting, with the use of monoclonal antibodies (mAb). mAb M73 recognizes the E1A products, whereas Mabs AIC6 and C1G11 are directed against the 55-kDa and 21 kDa E1B proteins, respectively. The antibodies did not recognize proteins in extracts from the parental A549 or the primary HER cells (data not shown). None of the A549 clones that were generated by co-transfection of pIG.NEO and pIG.E1A.E1B expressed detectable levels of E1A or E1B proteins(not shown). Some of the A549 clones that were generated by transfection with pIG.E1A.NEO expressed the Ad5 E1A proteins (FIG. 7), but the levels were much lower than those detected in protein lysates from 293 cells. The steady state E1A levels detected in protein extracts from PER cells were much higher than those detected in extracts from A549-derived cells. All PER cell lines expressed similar levels of E1A proteins (FIG. 7). The expression of the E1B proteins, particularly in the case of E1B 55 kDa, was more variable. Compared to 911 and 293, the majority of the PER clones express high levels of E1B 55 kDa and 2 kDa. The steady state level of E1B 21 kDa was the highest in PER.C3. None of the PER clones lost expression of the Ad5 E1 genes upon serial passage of the cells (not shown). We found that the level of E1 expression in PER cells remained stable for at least 100 population doublings. We decided to characterize the PER clones in more detail.

Southern Analysis of PER Clones

Figure 8:
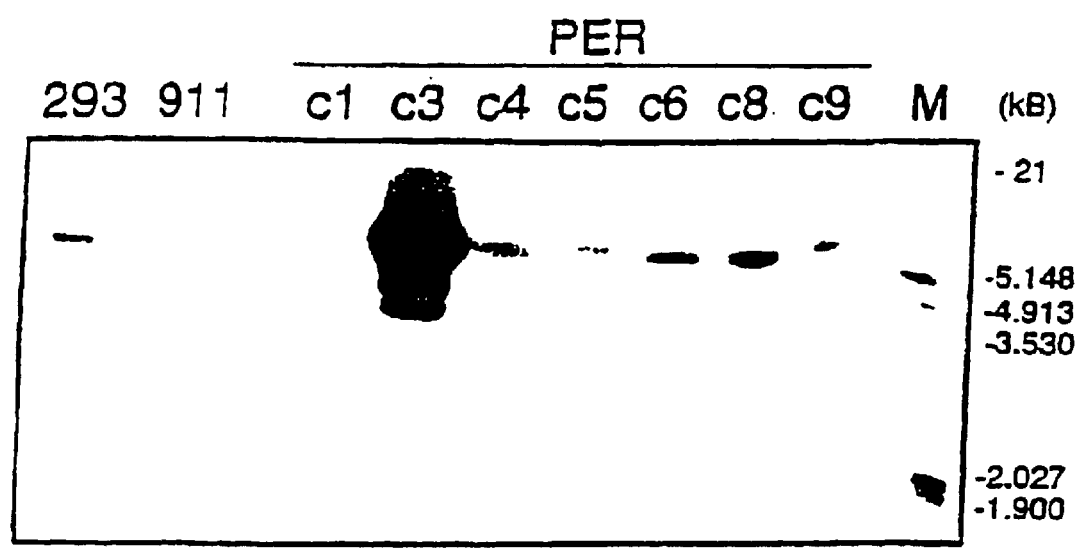
FIG. 8 is a Southern blot analysis of 293, 911 and PER cell lines. Cellular DNA was extracted, Hind III digested, electrophoresed and transferred to Hybond N'membranes (Amersham). Membranes were hybridized to radio-labeled probes generated by random priming of the Ssp I-Hind III fragment of pAd5.SalB (Ad5 nucleotides 342–2805).

To study the arrangement of the Ad5-E1 encoding sequences in the PER clones, we performed Southern analyses. Cellular DNA was extracted from all PER clones, and from 293 and 911 cells. The DNA was digested with HindIII, which cuts once in the Ad5 E1 region. Southern hybridization on HindIII-digested DNA, using a radio-labeled Ad5-E1-specific probe revealed the presence of several integrated copies of pIG.E1A.E1B in the genome of the PER clones. FIG. 8 shows the distribution pattern of E1 sequences in the high molecular weight DNA of the different PER cell lines. The copies are concentrated in a single band, which suggests that they are integrated as tandem repeats. In the case of PER.C3, C5, C6 and C9, we found additional hybridizing bands of low molecular weight that indicate the presence of truncated copies of pIG.E1A.E1B. The number of copies was determined with the use of a Phosphor-Imager. We estimated that PER.C1, C3, C4, C5, C6, C8 and C9 contain 2, 88, 5, 4, 5, 5, and 3 copies of the Ad5 E1 coding region, respectively, and that 911 and 293 cells contain 1 and 4 copies of the Ad5 E1 sequences, respectively.

Transfection Efficiency

Figure 9:
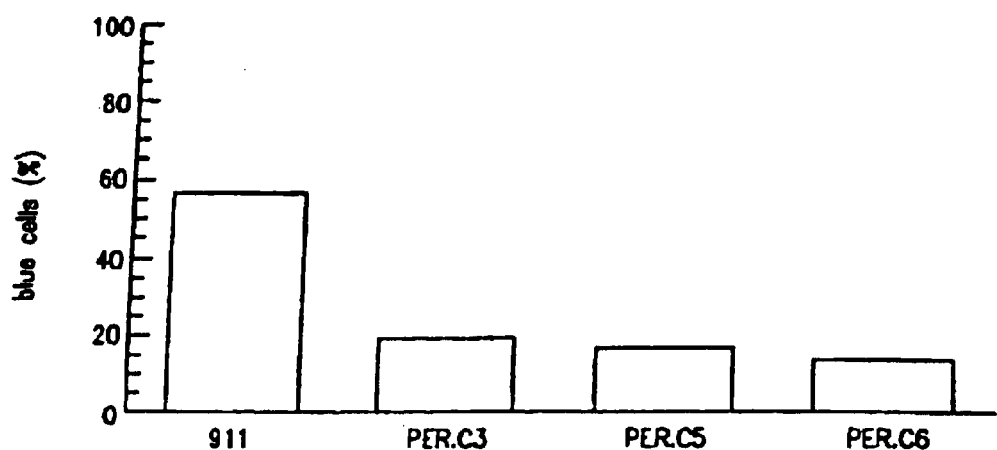
FIG. 9 illustrates the transfection efficiency of PER.C3, PER.C5, PER.C6, and 911 cells. Cells were cultured in 6-well plates and transfected in duplicate with 5 µg pRSV. lacZ by calcium-phosphate co-precipitation. 48 hours post-transfection, cells were stained with X-GAL and blue cells were counted. Results shown are the mean percentage of blue cells per well.

Recombinant adenovectors are generated by co-transfection of adapter plasmids and the large ClaI fragment of Ad5 into 293 cells (EPO patent application 95202213). The recombinant virus DNA is formed by homologous recombination between the homologous viral sequences that are present in the plasmid and the adenovirus DNA. The efficacy of this method, as well as that of alternative strategies, is highly dependent on the transfectability of the helper cells. Therefore, we compared the transfection efficiencies of some of the PER clones with 911 cells, using the E. coli β-galactosidase-encoding LacZ gene as a reporter (FIG. 9).

Production of Recombinant Adenovirus

Yields of recombinant adenovirus obtained after inoculation of 293, 911, PER.C3, PER.C5 and PER.C6 with different adenoviral vectors are presented in Table II.

The results indicate that the recombinant adenoviral vector yields obtained with PER cells are at least as high as those obtained with the existing cell lines. In addition, the yields of the novel adenoviral vector IG.Ad.MLPI.TK are similar or higher dm the yields obtained for the other viral vectors on all cell lines tested.

Figure 10:
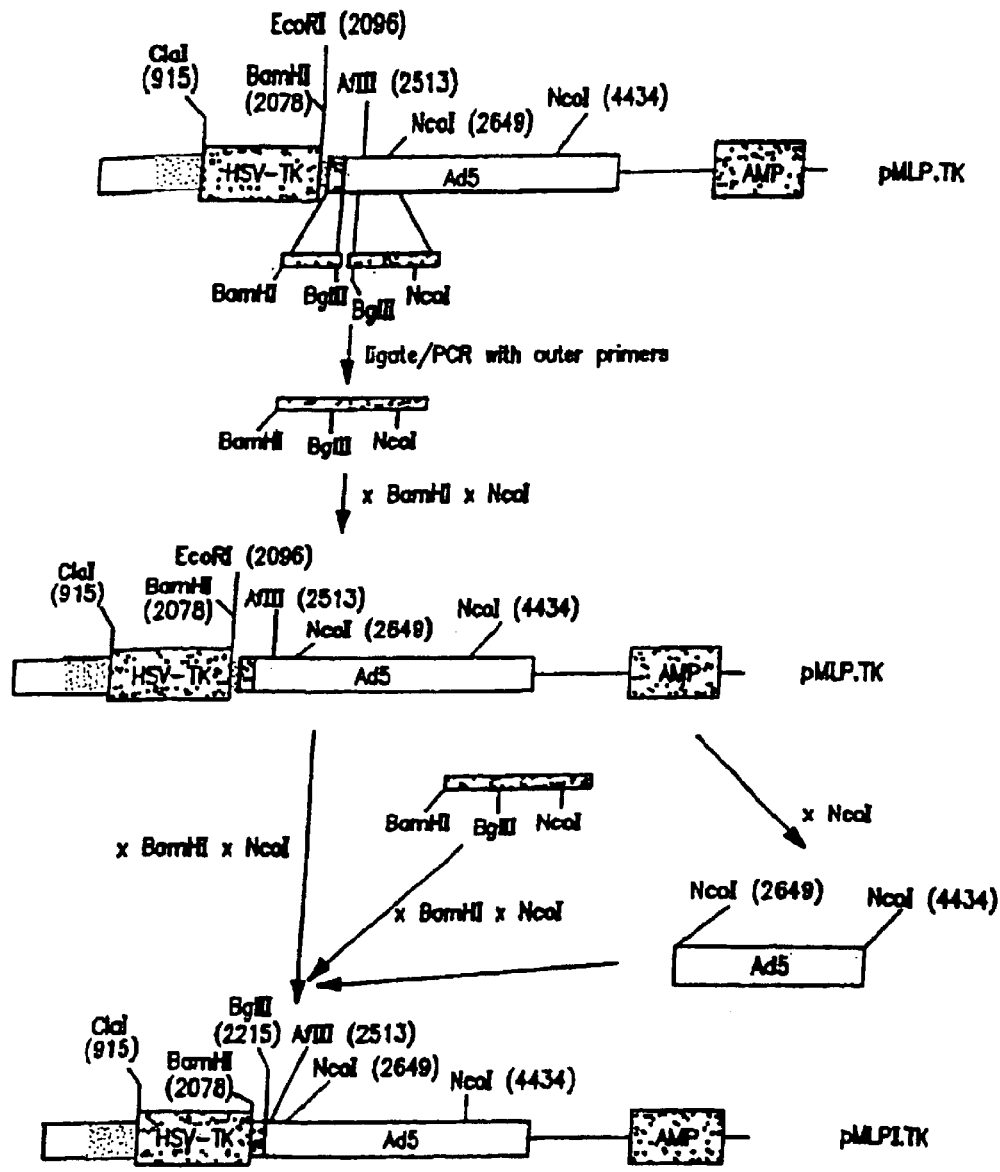
FIG. 10 depicts the construction of adenoviral vector, pMLPI.TK. pMLPI.TK was designed to have no sequence overlap with the packaging construct pIG.E1A.E1B. pMLPI.TK was derived from pMLP.TK by deletion of the region of sequence overlap with pIG.E1A.E1B and deletion of non-coding sequences derived from LacZ. SV40 poly(A) sequences of pMLP.TK were PCR amplified with primers SV40-1, which introduces a BamH I site and SV40-2, which introduces a Bgl II site. pMLP.TK Ad5 sequences 2496 to 2779 were PCR amplified with primers Ad5-1, which introduces a Bgl II site and Ad5-2. Both PCR products were Bgl II digested, ligated, and PCR amplified with primers SV40-1 and Ad5-2. This third PCR product was BamH I and Afl III digested and ligated into the corresponding sites of pMLP.TK, producing pMLPI.TK.

Generation of New Adenoviral Vectors (FIG. 10)

The recombinant adenoviral vectors used (see, EPO patent application EP 95202213) are deleted for E1 sequences from nt. 459 to nt. 3328. As construct pE1A.E1B contains Ad5 sequences nt. 459 to nt. 3510, there is a sequence overlap of 183 nt. between E1B sequences in the packaging construct pIG.E1A.E1B and recombinant adenoviruses, such as, for example, IG.Ad.MLP.TK. The overlapping sequences were deleted from the new adenoviral vectors. In addition, non-coding sequences derived from LacZ, that are present in the original constructs, were deleted as well. This was achieved (see, FIG. 10) by PCR amplification of the SV40 poly (A) sequences from pMLP.TK using primers SV40-1 (introduces a BamHI site)

and SV40-2 (introduces a BglII site). In addition, Ad5 sequences present in this construct were amplified from nt. 2496 (Ad5-1, introduces a BglII site) to nt. 2779 (Ad5-2). Both PCR fragments were digested with BglII and were ligated. The ligation product was PCR amplified using primers SV40-1 and Ad5-2. The PCR product obtained was cut with BamHI and AflII and was ligated into pMLP.TK predigested with the same enzymes. The resulting construct, named pMLPI.TK, contains a deletion in adenoviral E1 sequences from nt. 459 to nt. 3510.

Packaging System

The combination of the new packaging construct pIG.E1A.E1B and the recombinant adenovirus pMLPI.TK, which do not have any sequence overlap, are presented in FIG. 11. In FIG. 11, the original situation is also presented, where the sequence overlap is indicated. The absence of overlapping sequences between pIG.E1A.E1B and pMLPI.TK (FIG. 11a) excludes the possibility of homologous recombination between the packaging construct and the recombinant virus, and is, therefore, a significant improvement for producing recombinant adenovirus as compared to the original situation.

In FIG. 11b, the situation is depicted for pIG.E1A.NEO and IG.Ad.MLPI.TK. pIG.E1A.NEO when transfected into established cells, is expected to be sufficient to support propagation of E1-deleted recombinant adenovirus. This combination does not have any sequence overlap, preventing generation of RCA by homologous recombination. In addition, this convenient packaging system allows the propagation of recombinant adenoviruses that are deleted just for E1A sequences and not for E1B sequences.

Recombinant adenoviruses expressing E1B in the absence of E1A are attractive, as the E1B protein, in particular E1B 19 kD, is able to prevent infected human cells from lysis by Tumor Necrosis Factor (TNF) Gooding et al., (1991) J. Virol. 65:3083–3094).

Generation of Recombinant Adenovirus Derived FROM pMLPI.TK

Figure 12:
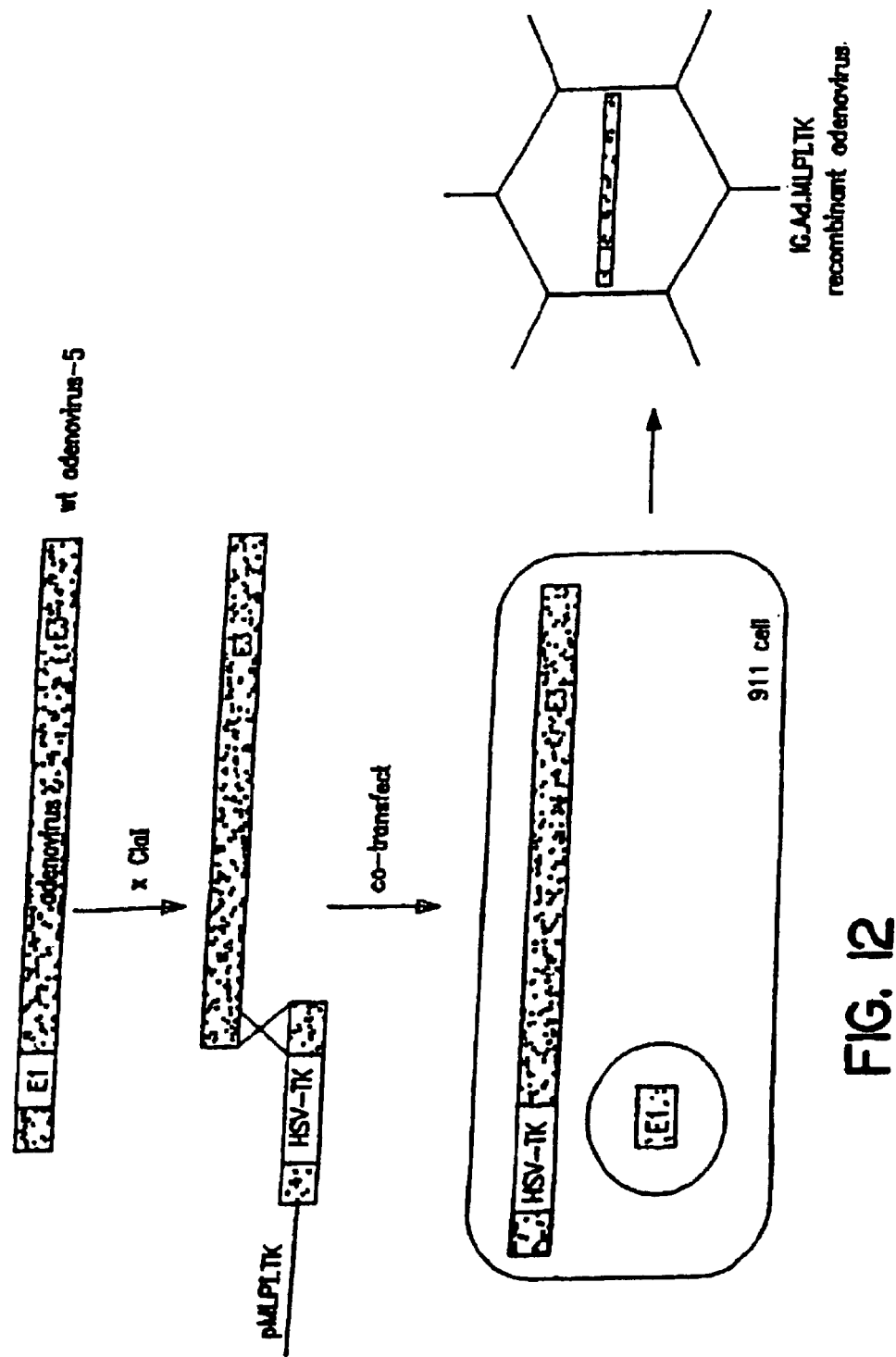
FIG. 12 depicts the generation of recombinant ad, IG.Ad.MLPI.TK. Recombinant ad, IG.Ad.MLPI.TK, was generated by co-transfection of 293 cells, with Sal I linearized pMLPI.TK and the right arm of Cla I digested, wild-type Ad5 DNA. Homologous recombination between linearized pMLPI.TK and wild-type Ad5 DNA produces IG.Ad.MLPI.TK DNA, which contains an E1 deletion of nucleotides 459–3510. 293 cells transcomplement the deleted Ad5 genome, thereby, permitting replication of the IG.Ad.MLPI.TK DNA and its packaging into virus particles.

Recombinant adenovirus was generated by co-transfection of 293 cells with SalI linearized pMLPI.TK DNA and ClaI linearized Ad5 wt DNA. The procedure is schematically represented in FIG. 12.

Example 2

Plasmid-Based System for Rapid RCA-Free Generation of Recombinant Adenoviral Vectors A. Construction of Adenovirus Clones pBr/Ad.Bam-rITR (ECACC deposit P970821212

In order to facilitate blunt end cloning of the ITR sequences, wild-type human Ad5 DNA was treated with Klenow enzyme in the presence of excess dNTPs. After inactivation of the Klenow enzyme, and purification by phenol/chloroform extraction followed by ethanol precipitation, the DNA was digested with BamHI. This DNA preparation was used without further purification in a ligation reaction with pBr322 derived vector DNA prepared as follows: pBr322 DNA was digested with EcoRV and BamHI, dephosphorylated by treatment with TSAP enzyme (Life Technologies) and purified on LNP agarose gel (SeaPlaque GTG). After transformation into competent E. coli DH5α (Life Techn.) and analysis of ampicillin resistant colonies, one clone was selected that showed a digestion pattern as expected for an insert extending from the BamHI site in Ad5 to the right ITR. Sequence analysis of the cloning border at the right ITR revealed that the most 3' G residue of the ITR was missing, the remainder of the ITR was found to be correct. The missing G residue is complemented by the other ITR during replication.

pBr/Ad.Sal-rITR (ECACC deposit P97082119)

pBr/Ad.Bam-rITR was digested with BamHI and SalI. The vector fragment including the adenovirus insert was isolated in LMP agarose (SeaPlaque GTG) and ligated to a 4.8 kb SalI/BamHI fragment obtained from wt Ad5 DNA and purified with the Geneclean II kit (Bio 101, Inc.). One clone was chosen and the integrity of the Ad5 sequences was determined by restriction enzyme analysis. Clone pBr/Ad.Sal-rITR contains adeno type 5 sequences from the SalI site at bp 16746 up to and including the rITR (missing the most 3'G residue).

pBr/Ad.Cla-Bam (ECACC deposit P97082117)

wt Adeno type 5 DNA was digested with ClaI and BamHI, and the 20.6 kb fragment was isolated from gel by electroelution. pBr322 was digested with the same enzymes and purified from agarose gel by Geneclean. Both fragments were ligated and transformed into competent DH5α. The resulting clone, pBr/Ad.Cla-Bam, was analyzed by restriction enzyme digestion and shown to contain an insert with adenovirus sequences from bp 919 to 21566.

pBr/Ad.AflII-Bam (ECACC deposit P97082114)

Clone pBr/Ad.Cla-Bam was linearized with EcoRI (in pBr322) and partially digested with AflII. After heat inactivation of AflII for 20 minutes at 65° C., the fragment ends were filled in with Klenow enzyme. The DNA was then ligated to a blunt double stranded oligo linker containing a PacI site (5'-AATTGTC<u>TTAATTAA</u>CCGCTTAA-3' (SEQ. ID. NO. 1)). This linker was made by annealing the following two oligonucleotides: 5'-AATTGTCTTAATTAACCGC-31 (SEQ. ID. NO. 2) and 5'-AATTGCGGTTAATTAAGAC-3'(SEQ. ID. NO. 3), followed by blunting with Klenow enzyme. After precipitation of the ligated DNA to change buffer, the ligations were digested with an excess PacI enzyme to remove concatameres of the oligo. The 22016 bp partial fragment containing Ad5 sequences from bp 3534 up to 21566 and the vector sequences, was isolated in LMP agarose (SeaPlaque GTG), re-ligated and transformed into competent DH5a. One clone that was found to contain the PacI site and that had retained the large adeno fragment was selected and sequenced at the 5' end to verify correct insertion of the PacI linker in the (lost) AflII site.

pBr/Ad.Bam-rITRpac#2 (ECACC deposit P97082120) and pBr/Ad.Bam-rITR#8 (ECACC deposit P97082121)

To allow insertion of a PacI site near the ITR of Ad5 in clone pBr/Ad.Bam-rITR about 190 nucleotides were removed between the ClaI site in the pBr322 backbone and the start of the ITR sequences. This was done as follows: pBr/Ad.Bam-rITR was digested with ClaI and treated with nuclease Bal31 for varying lengths of time (2', 5', 10' and 15'). The extent of nucleotide removal was followed by separate reactions on pBr322 DNA (also digested at the ClaI site), using identical buffers and conditions. Bal31 enzyme was inactivated by incubation at 75° C. for 10 minutes, the DNA was precipitated and re-suspended in a smaller volume TE buffer. To ensure blunt ends, DNAs were further treated with T4 DNA polymerase in the presence of excess dNTPs. After digestion of the (control) pBr322 DNA with SalI, satisfactory degradation (~150 bp) was observed in the samples treated for 10 minutes or 15 minutes. The 10 minutes or 15 minutes treated pBr/Ad.Bam-rITR samples were then ligated to the above described blunted PacI linkers (see, pBr/Ad.AflII-Bam). Ligations were purified by precipitation, digested with excess PacI and separated from the linkers on an LMP agarose gel. After religation, DNAs were transformed into competent DH5a and colonies analyzed. Ten clones were selected that showed a deletion of approximately the desired length and these were further analyzed by T-track sequencing (T7 sequencing kit, Pharmacia Biotech). Two clones were found with the PacI linker inserted just downstream of the RITR. After digestion with PacI, clone #2 has 28 bp and clone #8 has 27 bp attached to the ITR.

pWE/Ad.AflII-rITR (ECACC deposit P97082116)

Cosmid vector pWE15 (Clontech) was used to clone larger Ad5 inserts. First, a linker containing a unique PacI site was inserted in the EcoRI sites of pWE15 creating pWE.pac. To this end, the double stranded PacI oligo as described for pBr/Ad.AflII-BamHI was used but now with its EcoRI protruding ends. The following fragments were then isolated by electro-elution from agarose gel:pWE.pac digested with PacI, pBr/AflII-Bam digested with PacI and BamHI and pBr/Ad.Bam-rITR#2 digested with BamHI and PacI. These fragments were listed together and packaged using λ phage packaging extracts (Stratagene) according to the manufacturer's protocol. After infection into host bacteria, colonies were grown on plates and analyzed for presence of the complete insert. pWE/Ad.AflII-rITR contains all Ad5 sequences, from bp 3534 (AflII site) up to and including the right ITR (missing the most 3' G residue).

pBr/Ad.IITR-Sal(9.4) (ECACC deposit P97082115)

Adeno 5 wt DNA was treated with Klenow enzyme in the presence of excess dNTPs and subsequently digested with SalI. Two of the resulting fragments, designated left ITR-Sal(9.4) and Sal(16.7)-right ITR, respectively, were isolated in LMP agarose (Seaplaque GTG). pBr322 DNA was digested with EcoRV and SalI and treated with phosphatase (Life Technologies). The vector fragment was isolated using the Geneclean method (BIO 101, Inc.) and ligated to the Ad5 SalI fragments. Only the ligation with the 9.4 kb fragment gave colonies with an insert. After analysis and sequencing of the cloning border a clone was chosen that contained the full ITR sequence and extended to the SalI site at bp 9462.

pBr/Ad.1ITR-Sal(16.7) (ECACC deposit P97082118)

pBr/Ad1ITR-Sal(9.4) is digested with SalI and dephosphorylated (TSAP, Life Technologies). To extend this clone up to the third SalI site in Ad5, pBr/Ad.Cla-Bam was linearized with BamHI and partially digested with SalI. A 7.3 kb SalI fragment containing adenovirus sequences from 9462–16746 was isolated in LMP agarose gel and ligated to the SalI digested pBr/Ad.IITR-Sal(9.4) vector fragment.

EWE/Ad.AflII-EcoRI pWE.pac was digested with ClaI and the 5' protruding ends were filled in using Klenow enzyme. The DNA was then digested with PacI and isolated from agarose gel. pWE/AflII-rITR was digested with EcoRI and after treatment with Klenow enzyme digested with PacI. The large 24 kb fragment containing the adenoviral sequences was isolated from agarose gel and ligated to the ClaI-digested and blunted pWE.pac vector using the Ligation Express™ kit from Clontech. After transformation of Ultracompetent XL10-Gold cells from Stratagene, clones were identified that contained the expected insert. pWE/AflII-EcoRI contains Ad5 sequences from bp 3534–27336.

B. Construction of New Adapter Plasmids

The absence of sequence overlap between the recombinant adenovirus and E1 sequences in the packaging cell line is essential for safe, RCA-free generation and propagation of new recombinant viruses. The adapter plasmid pMLPI.TK (FIG. 10) is an example of an adapter plasmid designed for use according to the invention in combination with the improved packaging cell lines of the invention. This plasmid was used as the starting material to make a new vector in which nucleic acid molecules including specific promoter and gene sequences can be easily exchanged.

First, a PCR fragment was generated from pZipΔMo+ PyF101(N⁻) template DNA (described in PCT/NL96/00195) with the following primers: LTR-1: 5'-CTG TAC GTA CCA GTG CAC TGG CCT AGG CAT GGA AAA ATA CAT AAC TG-3' (SEQ. ID. NO. 4) and LTR-2: 5'-GCG GAT CCT TCG AAC CAT GGT AAG CTT GGT ACC GCT AGC GTT AAC CGG GCG ACT CAG TCA ATC G-3' (SEQ. ID. NO. 5). Pwo DNA polymerase (Boehringer Mannheim) was used according to the manufacturer's protocol with the following temperature cycles: once 5 minutes at 95° C.; 3 minutes at 55° C.; and 1 minute at 72° C., and 30 cycles of 1 minute at 95° C., 1 minute at 60° C., 1 minute at 72° C., followed by once 10 minutes at 72° C. The PCR product was then digested with BamHI and ligated into a pMLP10 (Levrero et al., (1991) Gene 101: 195–202) vector digested with PvuII and BamHI, thereby generating vector pLTR10. This vector contains adenoviral sequences from bp 1 up to bp 454 followed by a promoter which includes part of the Mo-MuLV LTR in which the wild-type enhancer sequences are replaced by the enhancer from a mutant polyoma virus (PyF101). The promoter fragment was designated L420.

Next, the coding region of the murine HSA gene was inserted. pLTR10 was digested with BstBI followed by Klenow treatment and digestion with NcoI. The HSA gene was obtained by PCR amplification on pUC18-HSA (Kay et al., (1990) J. Immunol. 145:1952–1959) using the following primers: HSA1, 5'-GCG CCA CCA TGG GCA GAG CGA TGG TGG C-3' (SEQ. ID. NO. 6) and HSA2,5'-GTT AGA TCT AAG CTT GTC GAC ATC GAT CTA CTA ACA GTA GAG ATG TAG AA-3'(SEQ. ID. NO. 7). The 269 bp amplified fragment was subcloned in a shuttle vector using the NcoI and BglII sites. Sequencing confirmed incorporation of the correct coding sequence of the HSA gene, but with an extra TAG insertion directly following the TAG stop codon. The coding region of the HSA gene, including the TAG duplication was then excised as a NcoI(sticky)-SalI (blunt) fragment and cloned into the 3.5 kb NcoI(sticky)/BstBI(blunt) fragment from pLTR10, resulting in pLTR-HSA10.

Finally, pLTR-HSA10 was digested with EcoRI and BamHI after which the fragment containing the left ITR, packaging signal, L420 promoter and HSA gene was inserted into vector pMLPI.TK digested with the same enzymes, thereby replacing the promoter and the gene sequences. This resulted in the new adapter plasmid pAd/L420-HAS (FIG. 21) that contains convenient recognition sites for various restriction enzymes around the promoter and gene sequences. SnaBI and AvrII can be combined with HpaI, NheI, KpnI, HindIII to exchange promoter sequences, while the latter sites can be combined with the ClaI or BamHI sites 3' from the HSA coding region to replace genes in this construct.

Another adapter plasmid that was designed to allow easy exchange of nucleic acid molecules was made by replacing the promoter, gene and poly A sequences in pAd/L420-HSA with the CMV promoter, a multiple cloning site, an intron and a poly-A signal. For this purpose, pAd/L420-HSA was digested with AvrII and BglII, followed by treatment with Klenow to obtain blunt ends. The 5.1 kb fragment with pBr322 vector and adenoviral sequences was isolated and ligated to a blunt 1570 bp fragment from pcDNA1/amp (Invitrogen) obtained by digestion with HhaI and AvrII followed by treatment with T4 DNA polymerase. This adapter plasmid was named pCLIP (FIG. 22).

C. Generation of Recombinant Adenoviruses

E1-Deleted Recombinant Adenoviruses with wt E3 Sequences

To generate E1 deleted recombinant adenoviruses with the new plasmid-based system, the following constructs were prepared: an adapter construct containing the expression cassette with the gene of interest linearized with a restriction enzyme that cuts at the 3' side of the overlapping adenoviral genome fragment, preferably not containing any pBr322 vector sequences; and a complementing adenoviral genome construct pWE/Ad.AflII-rITR digested with PacI.

Figure 23:
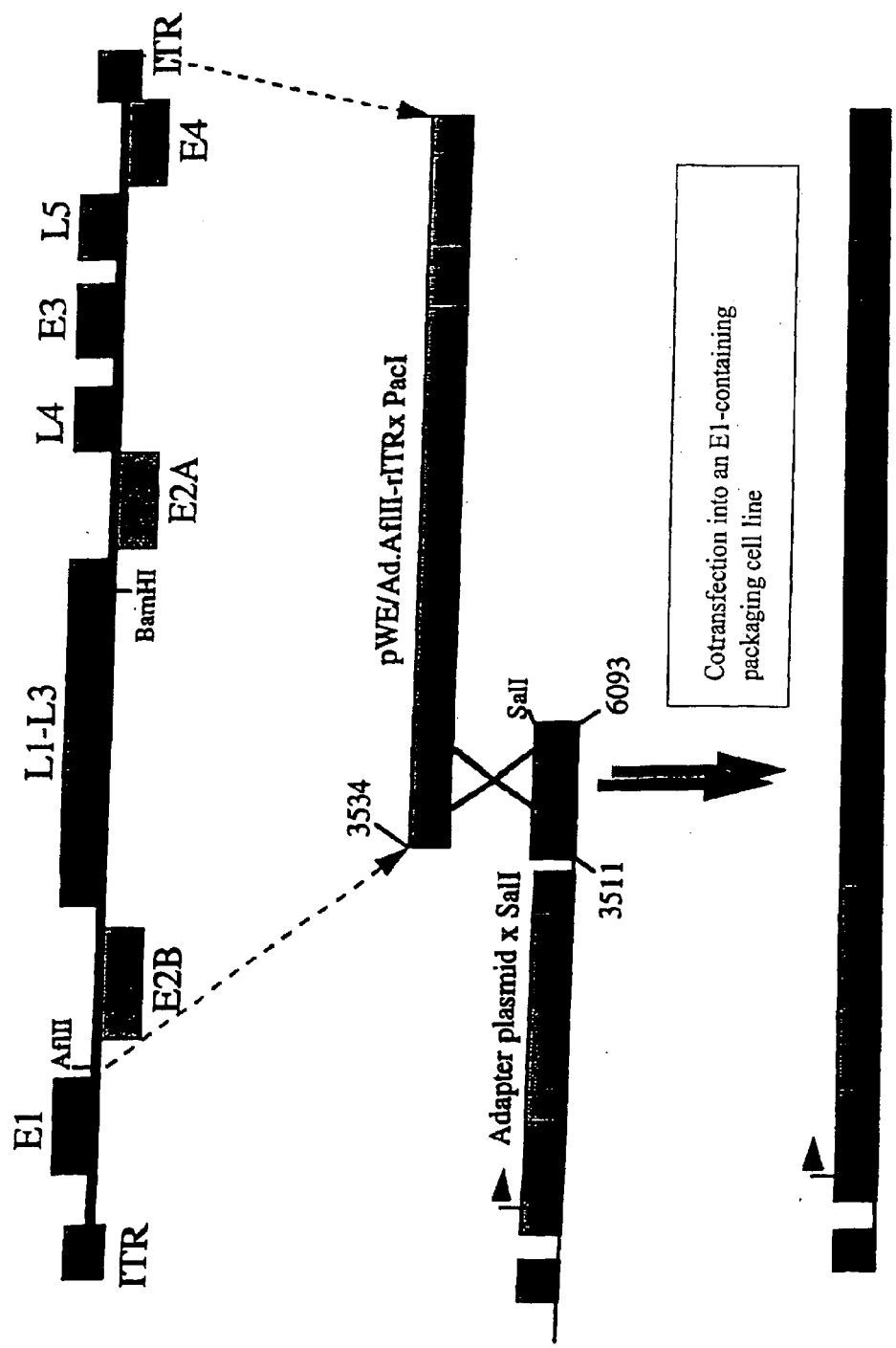
FIG. 23 schematically presents the generation of recombinant adenoviruses using a plasmid-based system. In the top, the genome organization of Ad5 is given with filled boxes representing the different early and late transcription regions, and flanking ITRs. The middle presents the two DNAs used for a single homologous recombination and, after transfection into packaging cells, leading to the recombinant virus (represented at the bottom).

These two DNA molecules are further purified by phenol/chloroform and ETOH precipitation. Co-transfection of these plasmids into an adenovirus packaging cell line, preferably a cell line according to the invention, generates recombinant replication deficient adenoviruses by a one-step homologous recombination between the adapter and the complementing construct (FIG. 23). Alternatively, instead of pWE/Ad.AflII-rITR other fragments can be used, for example, pBr/Ad.Cla-Bam digested with EcoRI and BamHI or pBr/Ad.AflII-BamHI digested with PacI and BamHI can be combined with pBr/Ad.Sal-rITR digested with SalI.

Recombinant adenovirus can be produced following introduction of the plasmids in the cell. It is to be understood that those skilled in the art may use other combinations of adapter and complementing plasmids without departing from the present invention.

A general protocol as outlined hereinafter, and meant as a non-limiting example of the present invention, has been performed to produce several recombinant adenoviruses using various adapter plasmids and the Ad.AflII-rITR fragment. Adenovirus packaging cells (PER.C6) were seeded in ~25 cm² flasks and the next day when they were at ~80!k confluency, were transfected with a mixture of DNA and lipofectamine agent (Life Techn.) as described by the manufacturer. Routinely, 40 µl lipofectamine, 4 µg adapter plasmid and 4 µg of the complementing adenovirus genome fragment AflII-rITR (or 2 µg of all three plasmids for the double homologous recombination) were used. Under these conditions, transient transfection efficiencies of ~50t (48 hrs post transfection) were obtained as determined with control transfections using a pAd/CMV-LacZ adapter. Two days later, cells were passaged to ~80 cm² flasks and further cultured. Approximately five (for the single homologous recombination) to eleven days (for the double homologous recombination) later a cytopathologic effect (CPE) was seen, indicating that functional adenovirus had formed. Cells and medium are harvested upon full CPE, and recombinant virus is released by freeze-thawing. An extra amplification step in a 80 cm² flask was routinely performed to increase the yield since, at the initial stage, the titers were found to be variable despite the occurrence of full CPE. After amplification, viruses were harvested and plaque purified on PER.C6 cells. Individual plaques were tested for viruses with active transgenes.

Four different recombinant adenoviruses, containing the human interleukin-3 gene (see, FIG. 1, PCT International Patent Appln. WO88/04691), the human endothelial nitric oxide gene (Janssens et al., (1992) *J. Biol. Chem.* 267:14519–14522), the Tc1A transposase gene (Vos et al., (1993) *Genes Dev.* 7:1244–1253), or the bacterial LacZ gene (Kalderon et al., (1984) *Cell* 39:499–509, have been produced using this protocol. In all cases, functional adenovirus was formed and all isolated plaques contained viruses with an active transgene.

E1-Deleted Recombinant Adenoviruses with Modifications in the E3 or E4 Regions

Besides replacing the E1 region, it is possible to delete the E3 region or replace part of the E3 region in the adenovirus because E3 functions are not necessary for the replication, packaging, and infection of a recombinant virus. This creates the opportunity to use a larger insert or to insert more than one gene without exceeding the maximum packagable size (approximately 105% of wt genome length). This can be done, for example, by deleting part of the E3 region in the pBr/Ad.Bam-rITR clone by digestion with XbaI and religation. This deletion removes Ad5 wt sequences 28592–30470 including all known E3 coding regions. Another example is the precise replacement of the coding region of gp19K in the E3 region with a polylinker allowing insertion of new sequences. This leaves all other coding regions intact and obviates the need for a heterologous promoter since the transgene is driven by the E3 promoter and pA sequences, leaving more space for coding sequences which results in very high transgene expression, at least as good as in a control E1 replacement vector.

To this end, the 2.7 kb EcoRI fragment from wt Ad5 containing the 5' part of the E3 region was cloned into the EcoRI site of pBluescript (KS_) (Stratagene). Next, the HindIII site in the polylinker was removed by digestion with EcoRV and HincII and subsequent religation. The resulting clone pBS.Eco-Eco/ad5ΔHIII was used to delete the gp19K coding region. Primers 1 (5'-GGG TAT TAG GCC AA AGG CGC A-3'(SEQ. ID. NO. 8)) and 2 (5'-GAT CCC ATG GAA GCT TGG GTG GCG ACC CCA GCG-3' (SEQ. ID. NO. 9)) were used to amplify a sequence from pBS.Eco-Eco/ad5ΔHIII corresponding to sequences 28511 to 28734 in wt Ad5 DNA. Primers 3 (5'-GAT CCC ATG GGG ATC CTT TAC TAA GTT ACA AAG CTA-3' (SEQ. ID. NO. 10)) and 4 (5'-GTC GCT GTA GTT GGA CTG G-3' (SEQ. ID. NO. 11)) were used on the same DNA to amplify Ad5 sequences from 29217 to 29476. The two resulting PCR fragments were ligated together by virtue of the newly introduced NcoI site and subsequently digested with XbaI and MunI. This fragment was then ligated into a pBS.EcoEco/ad5ΔHIII vector that had been partially digested with XbaI and MunI, generating pBS.EcoEco/ad5ΔHIII.Δgp19K.

To allow insertion of foreign genes into the HindIII and BamHI site, an XbaI deletion was made in pBS.Eco-Eco/ad5ΔHIII.Δgp19K to remove the BamHI sites in the Bluescript polylinker. The resulting plasmid pBS.Eco-Eco/ad5ΔHIII.Δgp19KΔXbaI contains unique HindIII and BamHI sites corresponding to sequences 28733 (HindIII) and 29218 (BamHI) in Ad5. After introduction of a foreign gene into these sites, either the deleted XbaI fragment is re-introduced, or the insert is re-cloned into pBS.Eco-Eco/ad5ΔHIII.Δgp19K using HindIII and, for example, MunI. Using this procedure, we have generated plasmids expressing HSV-TK (McKnight (1980) *Nucl. Acid. Res.* 8:5949–5964 and Vincent et al (1996) *Hum. Gene Ther.* 7:197–205), hIL-1α (Esandi et al., (1998) *Gene Therapy* 5:778–788), rat IL-3β (Esandi et al., (1998) *Gene* 211(1): 151–158:), luciferase (De Wit et al., (1987) *Mol. Cell Biol.* 7:725–737) or LacZ. The unique SrlI and NotI sites in the pBS.Eco-Eco/ad5ΔHIII.Δgp19K plasmid (with or without an inserted gene of interest) are used to transfer the region containing the gene of interest into the corresponding region of pBr/Ad.Bam-rITR, yielding construct pBr/Ad.Bam-rITRΔgp19K (with or without an inserted gene of interest). This construct is used as described, supra, to produce recombinant adenoviruses. In the viral context, expression of inserted genes is driven by the adenoviral E3 promoter.

Recombinant viruses that are both E1- and E3-deleted are generated by a double homologous recombination procedure as previously described for E1-replacement vectors using a plasmid-based system which includes: an adapter plasmid for E1 replacement according to the invention, with or without insertion of a first gene of interest, the pWE/Ad.AflII-EcoRI fragment, and the pBr/Ad.Bam-rITRΔgp19K plasmid with or without insertion of a second gene of interest.

In a non-limiting example, we describe the generation and functionality of a recombinant adenovirus containing the murine HSA gene in the E1 region and the firefly luciferase gene in the gp19K region. The luciferase gene was excised from pAd/MLP-Luc (described in EP 0707071) as a HindIII-BamHI construct and cloned into the HindIII-BamHI sites of pBS.Eco-Eco/ad5ΔHIII.Δgp19KΔXbaI. Then the MscI-MunI fragment containing the luciferase gene was cloned into the corresponding sites of pBS.Eco-Eco/ad5Δgp19K generating pBS.Eco-Eco/ad5Δgp19K.luc. This restores the Eco-Eco fragment, but now with the luciferase gene in the place of gp19K.

To simplify further manipulation, the internal EcoRI sites in the luciferase insert were mutated without making changes to the amino acid sequence of the luciferase gene. One EcoRI site flanked the HindIII site in the 5'non-coding region of the luciferase insert and the other one was located 588 bp 3' from the starting ATG. A 695 bp PCR product was generated with the following primers: 5'-CGA TAA GCT TAA TTC CTT TGT GTT T-3' (SEQ. ID. NO. 12) and 5'-CTT AGG TAA CCC AGT AGA TCC AGA GGA GTT CAT-3' (SEQ. ID. NO. 13) and digested with HindIII and BstEII. This fragment was then ligated to HindIII-BstEII digested pBS.Eco-Eco/ad5Δgp19K.luc, replacing the corresponding insert in this vector. The resulting construct is named pBS.EcoEco/ad5Δgp19K.luc$^2$. The luciferase gene and part of the E3 region was then excised from this clone with SrfI and NotI and introduced in the corresponding sites in pBr/Ad.Bam-rITR generating clone pBr/Ad.Bam-rITRΔgp19K/luc$^2$. The adapter plasmid pAd5/SI1800HSA used for the replacement of E1 in the double insert virus contains the murine HSA gene driven by a retrovirus LTR-based promoter. This adapter plasmid was generated from the pAd5/L420-HSA construct described infra by replacement of the promoter sequence. First a PCR product was generated on a retroviral vector based on the MFG-S vector described in WO95/34669 using the same primers as for amplifying the L420 promoter fragment (described infra). This PCR amplifies the sequences corresponding to bp 453–877 in the MFG-S vector. The L420 promoter in pAd5/L420-HSA (FIG. 21) was then exchanged for the PCR fragment using the unique AvrII and HindIII sites. The resulting construct, pAd5/S430-HSA, was then digested with NheI and ScaI and the 4504 bp fragment containing the HSA gene, pA sequences, Ad5 sequences and vector sequences to the ScaI site in the ampicillin gene was isolated.

The construct pAd5/S430-HSA also was digested with XbaI and ScaI and the 1252 bp fragment (containing the remainder of the ampicillin gene, the left ITR and packaging signal from adenovirus and the 5' part of the S430 promoter) was isolated. A third fragment of 1576 bp was isolated from the MFG-S-based retroviral vector following an XbaI digestion and contains MFG-S sequences corresponding to bp 695–2271.

The adapter plasmid pAd5/S1800-HSA was constructed by ligating the three isolated fragments. The double insert virus Ad5/S1800-HSA.E31uc was generated (as described above) by transfection of the following DNA fragments into PER.C6 cells: pAd5/S18000-HSA digested with EcoRI and SalI (2 μg)+pWE/Ad.AflII-EcoRI (2 μg) digested with PacI and EcoRI+pBr/Ad.Bam-rITRΔgp19klac$^2$ digested with SalI. At occurrence of CPE, the virus was harvested and amplified by serial passages on PER.C6 cells. The activity of this HSA-Luc virus was compared to single insert ΔEI viruses containing either the S1800-HSA or the CMV-Luc transcription units in the E1 region. A549 cells were seeded at 2×10$^5$ cells/well and infected 5 hrs later with different amounts of the virus. Two days later transgene expression was measured. Luciferase activity was measured using a luciferase assay system (Promega) and expression of the murine HSA gene was measured with an α-HSA antibody (M1/69, Pharmingen). The results are fisted in Table III.

This experiment shows that using the plasmid-based recombination system, double insert viruses can be made and that both inserts are functional. Furthermore, the luciferase activity of the double insert viruses is comparable to the CMV-driven luciferase activity of the control virus. Therefore, we conclude that the E3 promoter is highly active in A549 cells, even in the absence of E1A proteins.

In addition to manipulations in the E3 region, changes of (parts of) the E4 region can be accomplished easily in pBr/Ad.Bam-rITR. Generation and propagation of such a virus, however, in some cases demands complementation in trans.

Example 3

Demonstration of the Competence of a Synthetic DNA Sequence, that is Capable of Forming a Hairpin Structure, to Serve as a Primer for Reverse Strand Synthesis for Generating Double-Stranded DNA Molecules in Cells that Contain and Express Adenoviral Genes Name convention of the plasmids used:

| | |
|---|---|
| p | plasmid |
| I | ITR (Adenoviral ITR) |
| C | CMV Enhancer/Promoter Combination |
| L | Firefly Luciferase Coding Sequence | hac, haw Potential hairpin that can be formed after digestion with restriction endonuclease Asp718 in both the correct and in the reverse orientation, respectively (FIG. 15).

FIG. 15 depicts a potential hairpin conformation of a single-stranded DNA molecule (5'-GTACACTGACCTAGTGCCGCCCGGGCAAAGCCCG GGCGGCACTAG-3'(SEQ. ID. NO. 14) that contains the HP/asp sequence. Restriction with the endonuclease Asp718 of plasmid pICLhaw, containing the annealed oligonucleotide pair HP/asp1 and HP/asp2 will yield a linear double-stranded DNA fragment. In cells in which the required adenovirus genes are present, replication can initiate at the terminus that contains the ITR sequence. During the chain elongation, one of the strands will be displaced. The terminus of the single-stranded displaced strand molecule can adopt the conformation depicted in FIG. 15. In this conformation, the free 3'-terminus can serve as a primer for the cellular and/or adenoviral DNA polymerase, resulting in conversion of the displaced strand in a double-stranded form.

The naming convention is exemplified as follows. pICLhaw is a plasmid that contains the adenoviral ITR followed by the CMV-driven luciferase gene and the Asp718 hairpin in the reverse (non-functional) orientation.

Plasmids pICLhac, pICLhaw, pICLI and pICL were generated using standard techniques. The schematic representation of these plasmids is shown in FIGS. 16–19.

Plasmid pICL is derived from the following plasmids:

| | |
|---|---|
| nt. 1 | 457 pMLP10 (Levrero et al (1991)) Gene 101:195–202) |
| nt. 458 | 1218 pCMVβ (Clontech, EMBL Bank No. U02451) |
| nt. 1219 | 3016 pMLP.luc (IntroGene, unpublished) |
| nt. 3017 | 5620 pBLCATS (Stein et al., (1989) Mol. Cell Biol. 9:4531–4). |

The plasmid was constructed as follows:

The tet gene of plasmid pMLP10 was inactivated by deletion of the BamHI-SalI fragment, to generate pBLP10ΔSB. Using primer set PCR/MLP1 and PCR/MLP3 a 210 bp fragment containing the Ad5-ITR, flanked by a synthetic SalI restriction site was amplified using pMLP10 DNA as the template. The PCR product was digested with the enzymes EcoRI and SgrAI to generate a 196 bp fragment. Plasmid pMLP10ΔSB was digested with EcoRI and SgrAI to remove the ITR. This fragment was replaced by the EcoRI-SgrAI-treated PCR fragment to generate pMLP/SAL.

Figure 19:
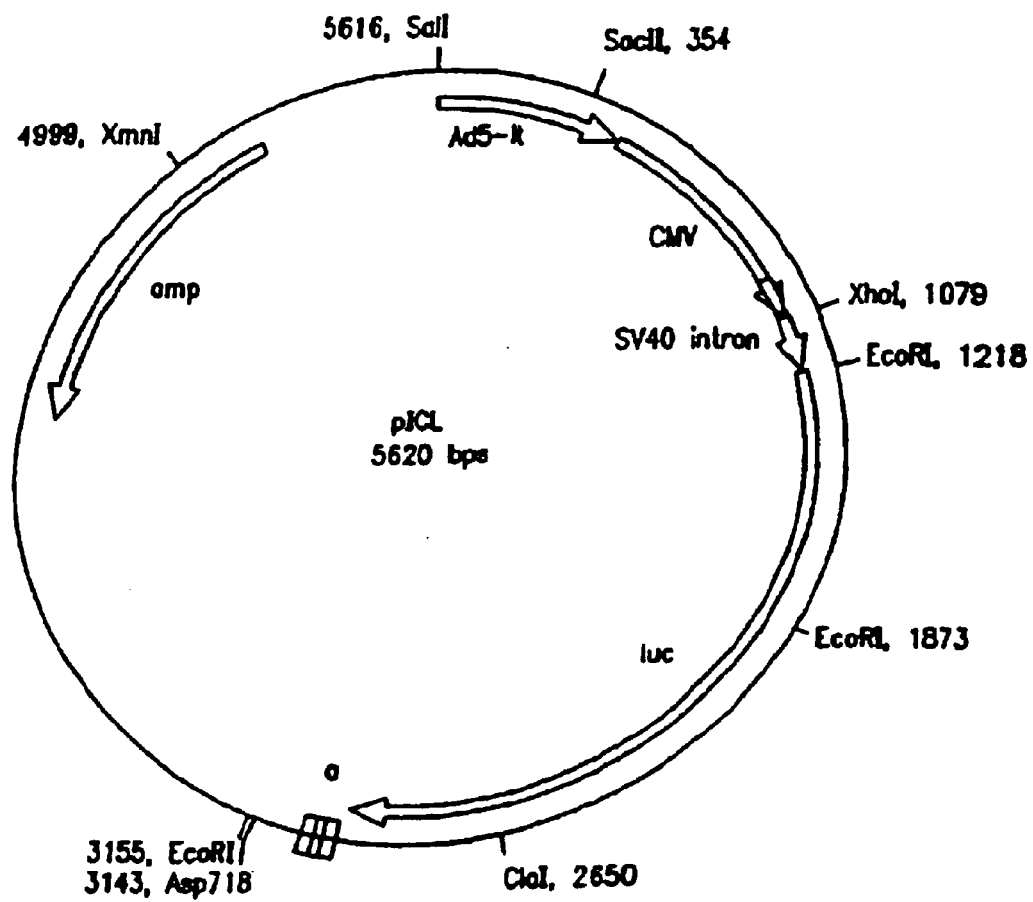
FIG. 19 is a diagram of pICL. pICL is derived from the following: (i) nucleotides 1–457, Ad5 nucleotides 1–457 including the left ITR, (ii) nucleotides 458–969, human CMV enhancer and immediate early promoter, (iii) nucleotides 970–1204, SV40 19S exon and truncated 16/19S intron, (iv) nucleotides 1218–2987, firefly luciferase gene, (v) nucleotides 3018–3131, SV40 tandem polyadenylation signals from the late transcript, (vi) nucleotides 3132–5620, pUC12 sequences including an Asp718 site, and (vii) ampicillin resistance gene in reverse orientation.
Figure 20:
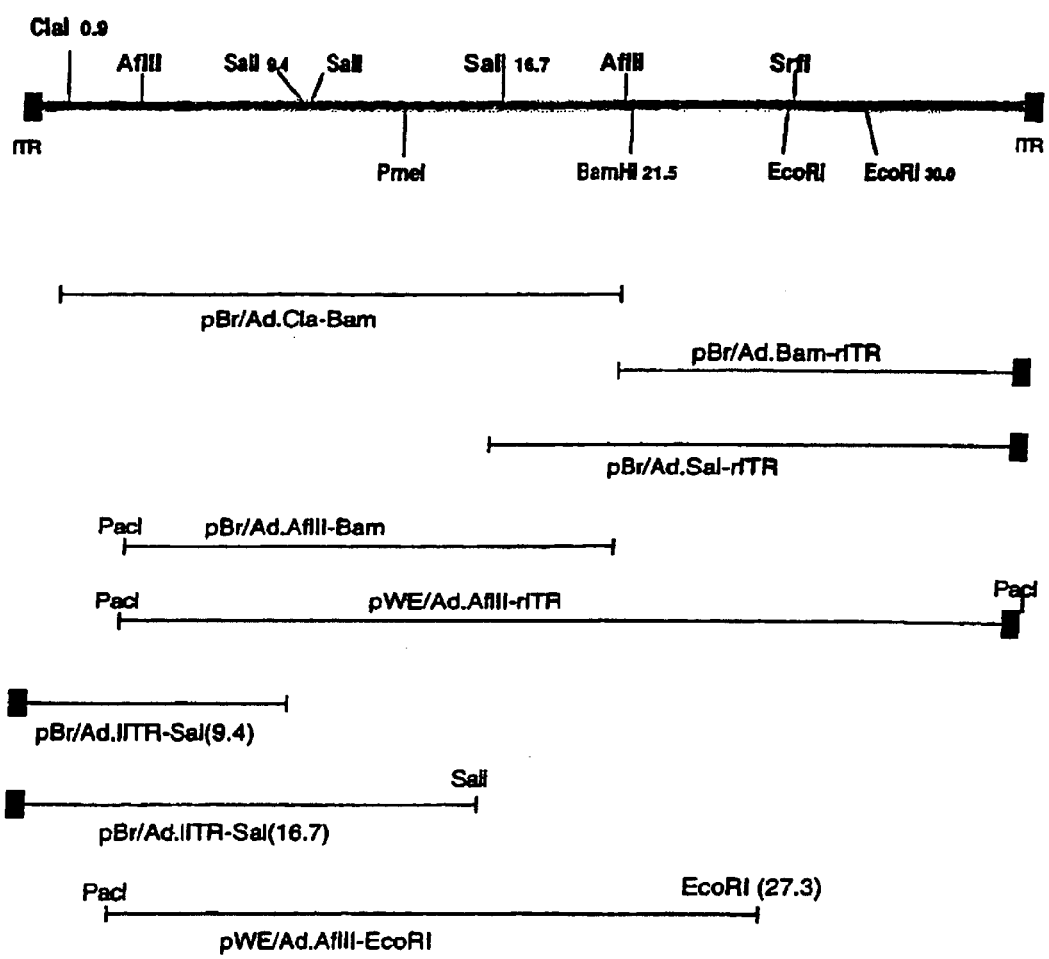
FIG. 20 shows a schematic overview of the adenoviral fragments cloned in pBr322 (plasmid) or pWE15 (cosmid) derived vectors. The top line depicts the complete adenovirus genome flanked by its ITRs (filled rectangles) and with some restriction sites indicated. Numbers following restriction sites indicate approximate digestion sites (in kb) in the Ad5 genome.

Plasmid pCMV-Luc was digested with PvuII to completion and re-circulated to remove the SV40-derived polyadenylation signal and Ad5 sequences with exception of the Ad5 left-terminus. In the resulting plasmid, pCMV-LucΔAd, the Ad5 ITR was replaced by the Sal-site-flanked ITR from plasmid pMLP/SAL by exchanging the XmnI-SacII fragments. The resulting plasmid, pCMV-LucΔAd/SAL, the Ad5 left terminus and the CMV-driven luciferase gene were isolated as a SalI-SmaI fragment and inserted in the SalI and HpaI digested plasmid pBLCATS, to form plasmid pICL. Plasmid pICL is represented in FIG. 19; its sequence is presented in FIG. 20.

Plasmid pICL contains the following features:

| | |
|---|---|
| nt. 1–457 | Ad5 left terminus (Sequence 1–457 of human Ad5) |
| nt. 458–969 | Human enhancer and immediate early promoter (Boshart et al., (1985) Cell 41:521–530) (from plasmid pCMVβ, Clontech, Palo Alto, USA) |
| nt. 970–1204 | SV40 19S exon and truncated 16/19S intron (from plasmid pCMVβ) |
| nt. 1218–2987 | Firefly luciferase gene (from pMLP.luc) |
| nt. 3018–3131 | SV40 tandem poly-adenylation signals from late transcript, derived from plasmid pBLCAT5) |
| nt. 3132–5620 | pUC12 backbone (derived from plasmid pBLCAT5) |
| nt. 4337–5191 | β-lactamase gene (Amp-resistance gene, reverse orientation) |

Plasmids pICLhac and pICLhaw

Plasmids pICLhac and pICLhaw were derived from plasmid pICL by digestion of pICL with the restriction enzyme Asp718. The linearized plasmid was treated with Calf-Intestine Alkaline Phosphatase to remove the 5ʹ phosphate groups. The partially complementary synthetic single-stranded oligonucleotides Hp/asp1 and Hp/asp2 were annealed and phosphorylated on their 5ʹ ends using T4-polynucleotide kinase.

Figure 16:
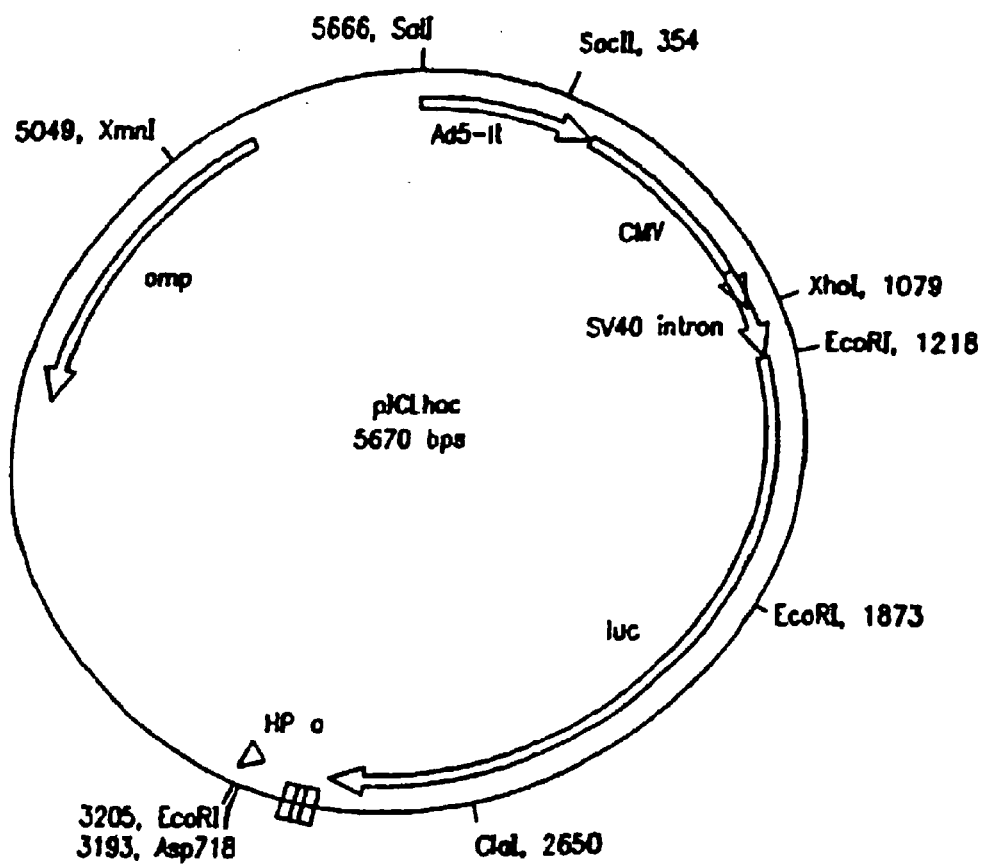
FIG. 16 is a diagram of pICLhac. pICLhac contains all the elements of pICL (FIG. 19) but also contains, in the Asp718 site, the HP/asp sequence in an orientation that will produce the hairpin structure shown in FIG. 15, following linearization by Asp718 digestion and transfection into cells expressing adenoviral E2 proteins.
Figure 17:
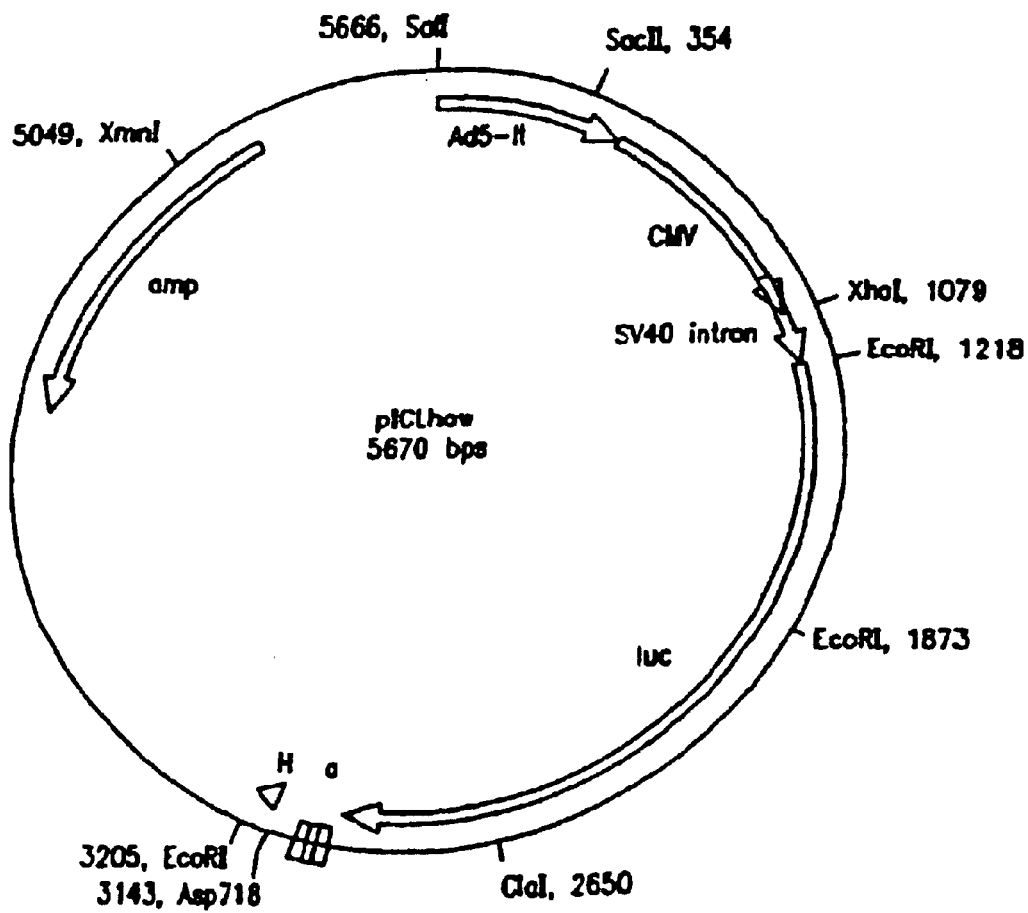
FIG. 17 is a diagram of pICLhaw. pICLhaw is identical to pICLhac (FIG. 16) with the exception that the inserted. HP/asp sequence is in the opposite orientation.

The phosphorylated double-stranded oligomers were mixed with the dephosphorylated pICL fragment and ligated. Clones containing a single copy of the synthetic oligonucleotide inserted into the plasmid were isolated and characterized using restriction enzyme digests. Insertion of the oligonucleotide into the Asp718 site will at one junction recreate an Asp718 recognition site, whereas at the other junction the recognition site will be disrupted. The orientation and the integrity of the inserted oligonucleotide was verified in selected clones by sequence analyses. A clone containing the oligonucleotide in the correct orientation (the Asp718 site close to the 3205 EcoRI site) was denoted pICLhac. A clone with the oligonucleotide in the reverse orientation (the Asp718 site close to the SV40 derived poly-signal) was designated pICLhaw. Plasmids pICLhac and pICLhaw are represented in FIGS. 16 and 17.

Figure 18:
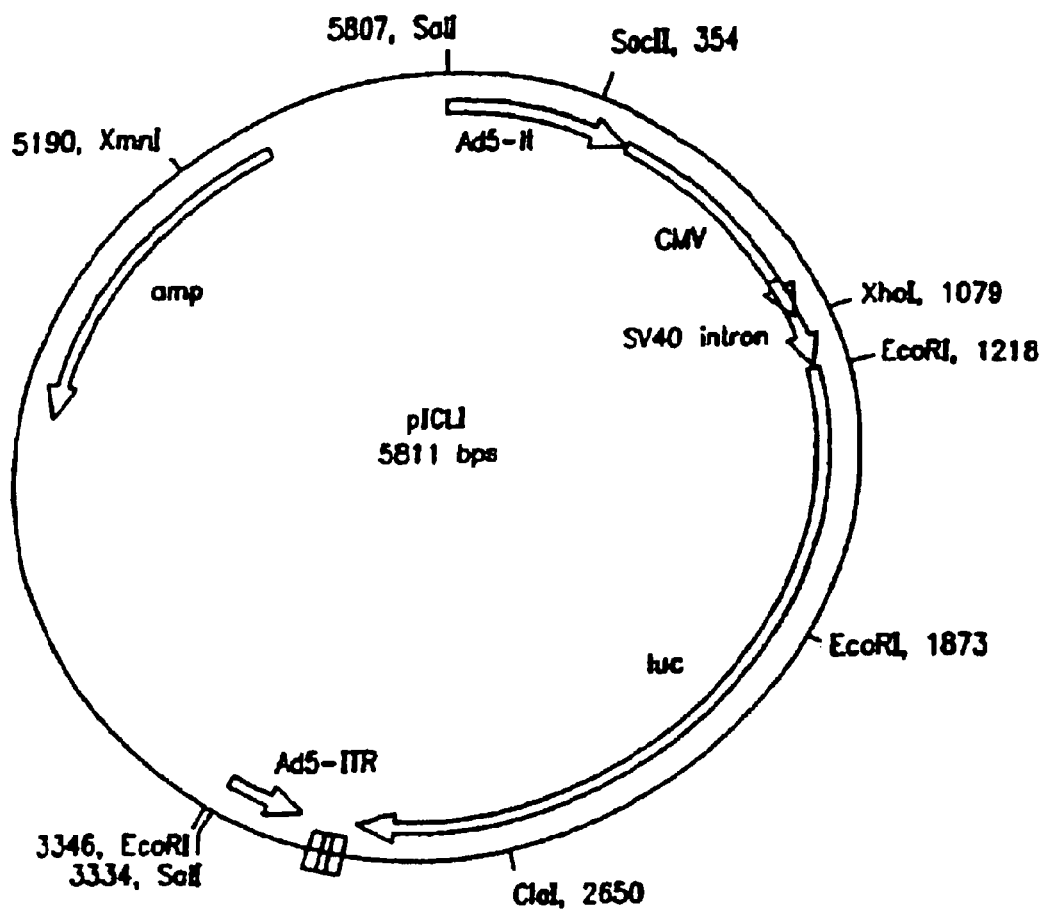
FIG. 18 is a schematic representation of pICLI. pICLI contains all the elements of pICL (FIG. 19) but also contains in the Asp718 site, an Ad5 ITR.

Plasmid pICLI was created from plasmid pICL by insertion of the SalI-SgrAI fragment from pICL, containing the Ad5-ITR into the Asp718 site of pICL. The 194 bp SalI-SgrAI fragment was isolated from pICL, and the cohesive ends were converted to blunt ends using *E. coli* DNA polymerase I (Klenow fragment) and dNTP's. The Asp718 cohesive ends were converted to blunt ends by treatment with mungbean nuclease. By ligation clones were generated that contain the ITR in the Asp718 site of plasmid pICL. A clone that contained the ITR fragment in the correct orientation was designated pICLI (FIG. 18).

Generation of adenovirus Ad-CMV-hcTK. Recombinant adenovirus was constructed according to the method described in EPO Patent application 95202213. Two components are required to generate a recombinant adenovirus. First, an adapter-plasmid containing the left terminus of the adenovirus genome containing the ITR and the packaging signal, an expression cassette with the gene of interest, and a portion of the adenovirus genome which can be used for homologous recombination. In addition, adenovirus DNA is needed for recombination with the aforementioned adapter plasmid. In the case of Ad-CMV-hcTK, the plasmid PCMV.TK was used as a basis. This plasmid contains nt. 1–455 of the Ad5 genome, nt. 456–1204 derived from PCMVβ (Clontech, the PstI-StuI fragment that contains the CMV enhancer promoter and the 16S/19S intron from simian Virus 40), the HSV-TK gene (described in EPO patent application 95202213.5), the SV40-derived polyadenylation signal (nt. 0.2533–2668 of the SV40 sequence), followed by the BglII-ScaI fragment of Ad5 (nt. 3328–6092 of the Ad5 sequence). These fragments are present in a pMLP10-derived (Levrero et al., (1991) *Gene* 101: 195–202) backbone. To generate plasmid pAD-CNWhc-TK, plasmid PCMV.TK was digested with ClaI (the unique ClaI-site is located just upstream of the TK open reading frame) and dephosphorylated with Calf-Intestine Alkaline Phosphate. To generate a hairpin-structure, the synthetic oligonucleotides HP/cla2 and HP/cla2 were annealed and phosphorylated on their 5ʹ—OH groups with T4-polynucleotide kinase and ATP. The double-stranded oligonucleotide was ligated with the linearized vector fragment and used to transform *E. coli* strain "Sure". Insertion of the oligonucleotide into the ClaI site will disrupt the ClaI recognition sites. The oligonucleotide contains a new ClaI site near one of its termini. In selected clones, the orientation and the integrity of the inserted oligonucleotide was verified by sequence analyses. A clone containing the oligonucleotide in the-correct orientation (the ClaI site at the ITR side) was denoted pAd-CMV-hcTK. This plasmid was co-transfected with ClaI-digested wild-type adenovirus-type 5 DNA into 911 cells. A recombinant adenovirus in which the CMV-hcTK expression cassette replaces the E1 sequences were isolated and propagated using standard procedures.

To study whether the hairpin can be used as a primer for reverse strand synthesis on the displaced strand after replication has started at the ITR, the plasmid piCLhac was introduced into 911 cells, i.e., HER transformed with the adenovirus-E1 region. The plasmid pICLhaw served as a control: it contains the oligonucleotide pair HP/asp 1 and 2 in the reverse orientation but is otherwise completely identical to plasmid pICLhac. Also included in these studies were plasmids pICLI and pICL. In the plasmid pICLI, the hairpin is replaced by an adenoviral ITR. Plasmid pICL contains neither a hairpin nor an ITR sequence. These plasmids served as controls to determine the efficiency of replication by virtue of the terminal hairpin structure. To provide the viral products other than the E1 proteins (these are produced by the 911 cells) required for DNA replication the cultures were infected with the virus IG.Ad.MLPI.TK after transfection. Several parameters were being studied to demonstrate proper replication of the transfected DNA molecules. First, DNA extracted from the cell cultures transfected with the aforementioned plasmids and infected with IG.Ad.MLPI.TK virus was analyzed by Southern blotting for the presence of the expected replication intermediates, as well as for the presence of the duplicated genomes. Furthermore, from the transfected and IG.Ad.hMPI.TK infected cell populations, virus was isolated that can transfer a luciferase marker gene into luciferase negative cells and express it.

Plasmid DNA of plasmids pICLhac, pCLhaw, pICLI and PICL were digested with restriction endonuclease SalI and treated with mungbean nuclease to remove the 4 nucleotide single-stranded extension of the resulting DNA fragment. In this manner a natural adenovirus 5' ITR terminus on the DNA fragment was created. Subsequently, both the pICLhac and pICLhaw plasmids were digested with restriction endonuclease Asp718 to generate the terminus capable of forming a hairpin structure. The digested plasmids were introduced into 911-cells, using the standard calcium phosphate co-precipitation technique, four dishes for each plasmid. During the transfection, for each plasmid two of the cultures were infected with the IG.Ad.MLPI.TK virus using 5 infectious IG.Ad.MLPI.TK particles per cell. At twenty-hours post-transfection and forty hours post-transfection, one Ad.tk-virus-infected and one uninfected culture were used to isolate low molecular-weight DNA using the procedure devised by Hirt (as described in Einerhand et al., (1995) Gene Therapy 2:336–343). Aliquots of isolated DNA were used for Southern analysis. After digestion of the samples with restriction endonuclease EcoRI using the luciferase gene as a probe, a hybridizing fragment of approx. 2.6 kb was detected in only the samples from the adenovirus-infected cells transfected with plasmid pICLhac. The size of this fragment was consistent with the anticipated duplication of the luciferase marker gene. This supports the conclusion that the inserted hairpin is capable of serving as a primer for reverse stand synthesis. The hybridizing fragment was absent if the IG.Ad.MLPI.TK virus was omitted, or if the hairpin oligonucleotide was inserted in the reverse orientation.

The restriction endonuclease DpnI recognizes the tetra-nucleotide sequence 5'-GATC-3', but cleaves only methylated DNA, (that is, only plasmid DNA propagated in, and derived, from E. coli, not DNA that has been replicated in mammalian cells). The restriction endonuclease MboI recognizes the same sequences, but cleaves only unmethylated DNA (namely, DNA propagated in mammalian cells). DNA samples isolated from the transfected cells are incubated with MboI and DpnI and analyzed with Southern blots. These results demonstrated that only in the cells transfected with the pICLhac and the pICLI plasmids, large DpnI-resistant fragments were present, that were absent in the MboI treated samples. These data demonstrate that only after transfection of plasmids pICLI and pICLhac replication and duplication of the fragments occur.

These data demonstrate that in adenovirus-infected cells, linear DNA fragments that have on one terminus an adenovirus-derived ITR and, at the other terminus, a nucleotide sequence that can anneal to sequences on the same strand, when present in single-stranded form thereby generate a hairpin structure, and will be converted to structures that have ITR sequences on both ends. The resulting DNA molecules will replicate by the same mechanism as the wild-type adenovirus genomes.

Example 4

Demonstration that the DNA Molecules that Contain a Luciferase Marker Gene, a Single Copy of the ITR, the Encapsidation Signal and a Synthetic DNA Sequence, that is Capable of Forming a Hairpin Structure, are Sufficient to Generate DNA Molecules that can be Encapsidated into Virions To demonstrate that the DNA molecules, generated in Example 3, containing two copies of the CMV-Luc marker gene can be encapsulated into virions, virus was harvested from the remaining two cultures via three cycles of freeze-thaw crushing and was used to infect murine fibroblasts. Forty-eight hours after infection the infected cells are assayed for luciferase activity. To exclude the possibility that the luciferase activity has been induced by transfer of free DNA, rather than via virus particles, virus stocks were treated with DNaseI to remove DNA contaminants. Furthermore, as an additional control, aliquots of the virus stocks were incubated for 60 minutes at 56° C. The heat treatment does not affect the contaminating DNA, but does inactivate the viruses. Significant luciferase activity was only found in the cells after infection with the virus stocks derived from IG.Ad.MLPI.TK-infected cells transfected with the pICLhc and PICLI plasmids. Neither in the non-infected cells, nor in the infected cells transfected with the pICLhw and pICL was significant luciferase activity demonstrated. Heat inactivation, but not DNaseI treatment, completely eliminated luciferase expression, demonstrating that adenovirus particles, and not free (contaminating) DNA fragments were responsible for transfer of the luciferase reporter gene.

These results demonstrate that these small viral genomes can be encapsulated into adenovirus particles and suggest that the ITR and the encapsulation signal are sufficient for encapsulation of linear DNA fragments into adenovirus particles. These adenovirus particles can be used for efficient gene transfer. When introduced into cells that contain and express at least some of the adenoviral genes (namely E1, E2, E4, and L, and VA), recombinant DNA molecules that include at least one ITR, at least part of the encapsidation signal as well as a synthetic DNA sequence, that is capable of forming a hairpin structure, have the intrinsic capacity to autonomously generate recombinant genomes which can be encapsulated into virions. Such genomes and vector system can be used for gene transfer.

Example 5

Demonstration that DNA Molecules which Contain Nucleotides 3510–35953 (Namely 9.7–100 Map Units) of the Ad5 Genome (thus Lack the E1 Protein-Coding Regions, the Right-Hand ITR and the Encapsidation Sequences) and a Terminal DNA Sequence that is Complementary to a Portion of the Same Strand of the DNA Molecule when Present in Single-Stranded Form Other than the ITR, and as a Result is Capable of Forming a Hairpin Structure, can Replicate in 911 Cells In order to develop a replicating DNA molecule that can provide the adenovirus products required to allow the above-mentioned ICLhac vector genome and alike minimal adenovectors to be encapsulated into adenovirus particles by helper cells, the Ad-CW-hcfK adenoviral vector was developed. Between the CMV enhancer/promoter region and the thymidine kinase gene, the annealed oligonucleotide pair (Table 1) HP/cla 1 and 2 was inserted. The vector Ad-CMV-hcTK was propagated and produced in 911 cell using standard procedures. This vector was grown and propagated exclusively as a source of DNA used for transfection. DNA of the adenovirus AdCMV-hcTK was isolated from virus particles that had been purified using CsCl density-gradient centrifugation by standard techniques. The virus DNA was digested with restriction endonuclease ClaI. The digested DNA was size-fractionated on an 0.7% agarose gel and the large fragment was isolated and used for further experiments. Cultures of 911 cells were transfected with the large ClaI-fragment of the Ad-CMV-hcTK DNA using standard calcium phosphate co-precipitation techniques. Much like in the previous experiments with plasmid pICLhac, the Ad-CMV-hc replicates starting at the right-hand ITR. Once the I-strand is displaced, a hairpin can be formed at the left-hand terminus of the fragment. This facilitates DNA polymerase elongation of the chain towards the right-hand side. The process proceeds until the displaced strand is completely converted to its double-stranded form. Finally, the right-hand ITR is recreated, and in this location, normal adenovirus replication-initiation and elongation occur. The polymerase reads through the hairpin, thereby duplicating the molecule. The input DNA molecule of 33250 bp, that had, on one side, an adenoviral ITR sequence and at the other side a DNA sequence that had the capacity to form a hairpin structure is duplicated so that both ends contain an ITR sequence. The resulting DNA molecule consists of a palindromic structure of approximately 66500 bp.

This structure is detected in low-molecular weight DNA extracted from transfected cells using Southern analysis. The palindromic nature of the DNA fragment can be demonstrated by digestion of the low-molecular weight DNA with suitable restriction endonucleases and Southern blotting with the HSV-TK gene as the probe. This molecule can replicate itself in the transfected cells by virtue of the adenoviral gene products that are present in the cells. In part, the adenoviral genes are expressed from templates that are integrated in the genome of the target cells (namely, the E1 gene products), the other genes reside in the replicating DNA fragment itself. This linear DNA fragment cannot be encapsulated into virions. Not only does it lack all the DNA sequences required for encapsulation, but its size also is much too large to be encapsulated.

Example 6

Demonstration that DNA Molecules Which Contain Nucleotides 3503–35953 (viz. 9.7–100 Map Units) of the Ad5 Genome (thus Lack the E1 Protein-Coding Regions, the Right-Hand ITR, and the Encapsidation Sequences) and a Terminal DNA Sequence that is Complementary to a Portion of the Same Strand of the DNA Molecule other than the ITR, and as a Result is Capable of Forming a Hairpin Structure, Can Replicate in 911 Cells and Can Provide the Helper Functions Required to Encapsidate the pICLI and pICLhac Derived DNA Fragments The purpose of the next series of experiments was to demonstrate that the DNA molecule described in Example 5 can be used to encapsulate the minimal adenovectors described in Examples 3 and 4.

The large fragment isolated after endonuclease ClaI-digestion of Ad-CW-hcTK DNA was introduced into 911 cells (as described in Example 5) together with endonuclease SalI, mungbean nuclease, endonuclease Asp718-treated plasmid pICLhac, or as a control similarly treated plasmid pICLhaw. After 48 hours, virus was isolated by freeze-thaw crushing of the transfected cell population. The virus preparation was treated with DNaseI to remove contaminating free DNA. The virus was used subsequently to infect Rat2 fibroblasts. Forty-eight hours post infection the cells were assayed for luciferase activity. Only in the cells infected with virus isolated from the cells transfected with the pICLhac plasmid, and not with the pICLhaw plasmid, was significant luciferase activity demonstrated. Heat inactivation of the virus prior to infection completely abolished the luciferase activity, indicating that the luciferase gene was transfected by a viral particle. Infection of 911 cell with the virus stock did not result in any CPE, demonstrating that pICLhac was produced without any infectious helper virus being propagated on 911 cells. These results demonstrate that the proposed method can be used to produce stocks of minimal-adenoviral vectors, that are completely devoid of infectious helper viruses that are able to replicate autonomously on adenovirus-transformed human cells or on non-adenovirus transformed human cells.

Example 7

Construction of Plasmids for the Generation and Production of Minimal Adenoviral Vectors A minimal adenoviral vector contains (as operably linked components) the adenovirus-derived cis elements necessary for replication and packaging, with or without foreign nucleic acid molecules to be transferred. Recently, the lower limit for efficient packaging of adenoviral vectors has been determined to be 75% of the genome length (Parks and Graham, 1997. To allow flexible incorporation of various lengths of stuffer fragments, a multiple cloning site (MCS) was introduced into a minimal adenoviral vector. To obtain a minimal adenoviral vector according to the invention, the following constructs were made: pAd/L420-HSA (FIG. 21) was digested with BglII and SalI and the vector-containing fragment was isolated. This fragment contains the left ITR and packaging signal from Ad5 and the murine HSA gene driven by a modified retroviral LTR. The right ITR of adenovirus was amplified by PCR on pBr/Ad.BamHI-rITR template DNA using the following primers: PolyL-ITR: 5'-AAC-TGC-AGA-TCT-ATCGAT-ACT-AGT-CAA-TTG-CTC-GAG-TCT-AGA-CTA-CGT-CAC-CCG-CCC-CGT-TCC-3'(SEQ. ID. NO. 15) and ITR-BSN; 5'-CGG-GAT-CCG-TCG-ACG-CGG-CCG-CAT-CAT-CAA-TAA-TAT-ACC-3'(SEQ. ID. NO. 16). The amplified fragment was digested with PstI and BamHI and cloned into pUC119 digested with the same enzymes. After sequence confirmation of correct amplification of the ITR and the MCS, a BglII-SalI fragment was isolated and cloned into the BglII/SalI-digested pAd/L420-HSA fragment described above. The resulting clone was named pAd/L420-HSA.ITR.

Figure 24:
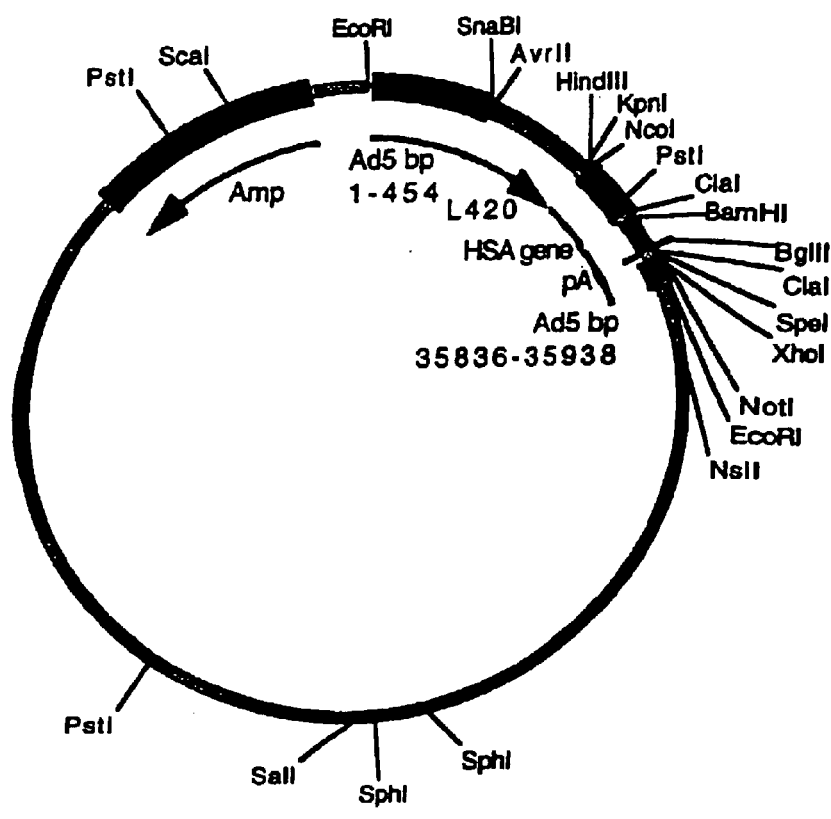
FIG. 24 is a drawing of minimal adenoviral vector pMY/L420H.

To be able to manipulate constructs of lengths exceeding 30 kb, the minimal adenoviral vector pAd/L420-HSA.ITR was subcloned in a cosmid vector background. To this end, the cosmid vector pWE15 was modified to remove restriction sites in the backbone pWE15 was digested with PstI and fragments of 4 kb and 2.36 kb were isolated from agarose gel and ligated together. The resulting clone, stripped of the SV40 ori/early promoter and neomycin resistance coding sequence, was named pWE20. Then, pWE20 was digested with ClaI and HindIII and the sticky ends were filled in with Klenow enzyme. A 6354 bp blunt fragment was ligated to a phosphorylated NsiI linker with the following sequence: 5'-CGATGCATCG-3' (SEQ. ID. NO. 17). The ligated DNA was phenol/chloroform extracted, precipitated with EtOH to change buffers, and digested with excess NsiI. Digested DNA was separated from the linkers by electrophoresis, isolated and religated. The resulting clone was named pWE25. Correct insertion of the NsiI linker was confirmed by restriction enzyme digestion and sequencing. To construct the minimal adenoviral vector, pAd/L420-HSA.ITR was digested with ScaI and NotI and the 2 kb fragment containing part of the ampicillin gene and the adeno ITRs was cloned into pWE25 digested with ScaI and NotI. The resulting clone was named pMV/L420H (FIG. 24). This clone allows easy manipulation to exchange the promoter and/or gene, and also- allows insertion of DNA fragments of lengths not easily cloned into normal plasmid backbones.

Plasmid pMV/CMV-LacZ was made by exchanging the L420-HSA fragment (SnaBI-BamHI) for a fragment from pcDNA3-nlsLacZ (NruI-BamHI) containing the CMV promoter and LacZ coding sequences. pcDNA3-nlsLacZ was constructed by insertion of a KpnI-BamHI fragment obtained after PCR amplification of the nlsLacZ coding sequences into pcDNA3 (Invitrogen) digested with KpnI and BamHI. The PCR reaction was performed on a pMLP-.nlsLacZ template DNA using the primers 1: 5'-GGG-GTG-GCC-AGG-GTA-CCT-CTA-GGC-TTT-TGC-AA-3u(SEQ. ID. NO. 18) and 2: 5'-GGG-GGG-ATC-CAT-AAA-CAA-GTT-CAG-AAT-CC-3'(SEQ. ID. NO. 19). Correct amplification and cloning were confirmed by assaying β-galactosidase expression in a transient transfection experiment on 911 cells.

The vector pAd/MLPnlsLacZ was made as follows: pMLP10 (Levrero et al., (1991) *Gene* 101:195–202) was digested with HindIII and BamHI and ligated, in a three-part ligation, to a 3.3 kb AvrII-BamHI fragment from L7RHβ-gal (Kalderon et al., (1984) *Cell* 499–509), and a synthetic linker with HindIII and XbaI overhang. The linker was made by annealing two oligonucleotides of sequence 5'-AGC TTG AAT TCC CGG GTA CCT-3' (SEQ. ID. NO. 20) and 5'-CTA GAG GTA CCC GGG AAT TCA-3' (SEQ. ID. NO. 21). The resulting clone was named pMLP.nlsLacZ/-Ad. Next, pMLP.nlsLacZ/-Ad was digested with BamHI and NruI and the vector containing fragment was ligated to a 2766 bp BglII-ScaI fragment from pAd5SalB (Bernards et al., (1982) *Virology* 120:422–432). This resulted in the adapter plasmid pMLP.nlsLacZ (described in European Patent Office application EP 0 707 071).

Figure 25:
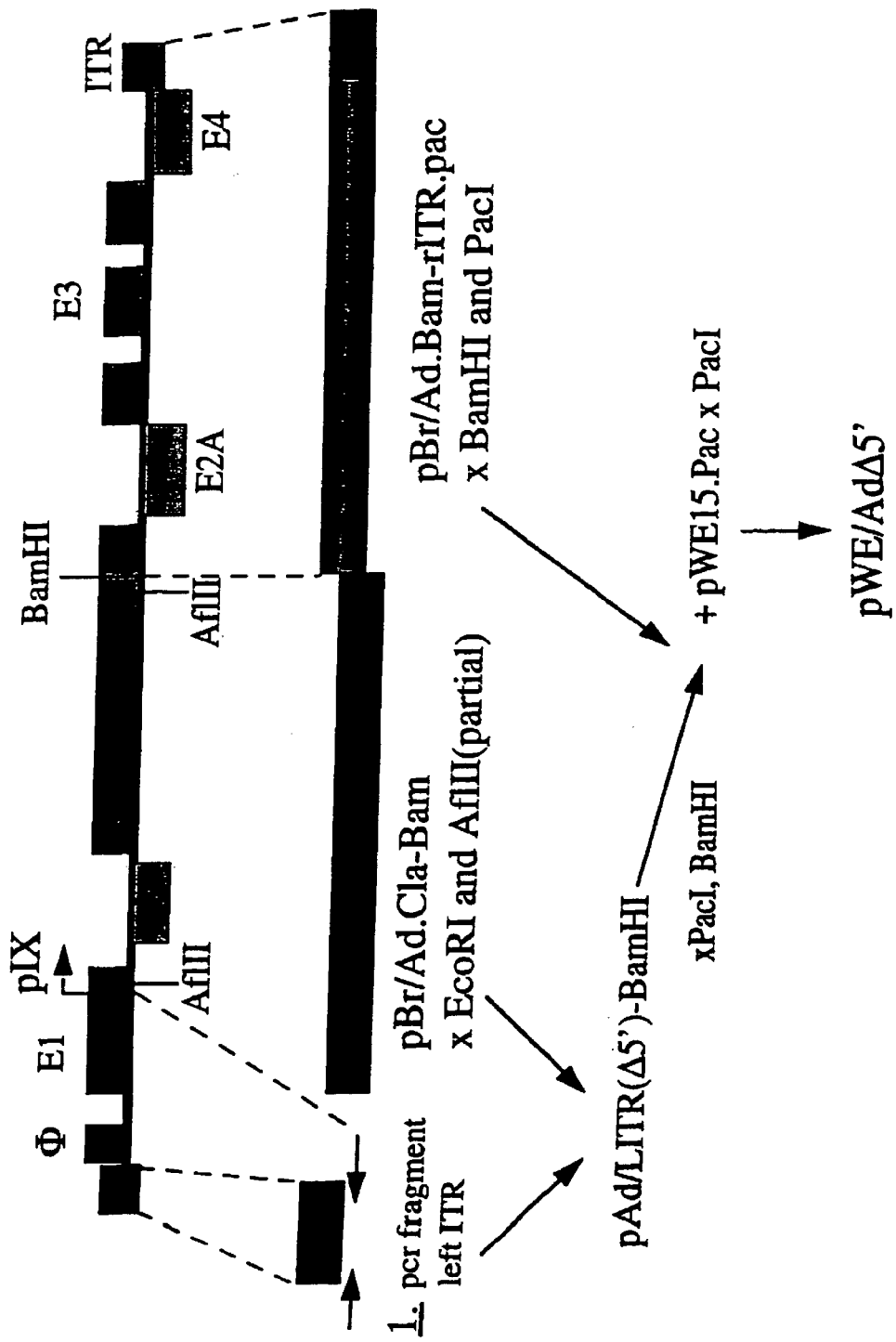
FIG. 25 schematically presents the cloning steps for generating (construction) the helper construct PWE/AdΔ5'.

Propagation of a minimal adenoviral vector can only be achieved by expression of adenoviral gene products. Expression of adenoviral gene products, at levels high enough to sustain production of large quantities of virus, requires replication of the coding nucleic acid molecule. Usually, therefore, replicating helper viruses are used to complement the minimal adenoviral vectors. The present invention, however, provides packaging systems for minimal adenoviral vectors without the use of helper viruses. One of the methods of the invention makes use of a replicating DNA molecule that contains the 5'-ITR and all adenoviral sequences between bp 3510 and 35938, i.e., the complete adenoviral genome except for the E1 region and the packaging signal. Construct pWE/Ad.Δ5' (FIG. 25) is an example of a replicating molecule according to the invention that contains two adenoviral-ITRs. pWE/Ad.Δ5'. It has been made in a cosmid vector background from three fragments. First, the 5' ITR from Ad5 was amplified using the following primers:

ITR-EPH: 5'-CGG-AAT-TCT-TAA-TTA-AGT-TAA-CAT-CAT-CAA-TAA-TAT-ACC-3'(SEQ. ID. NO. 22) and ITR-pIX: 5'-ACG-GCG-CGC-CTT-AAG-CCA-CGC-CCA-CAC-ATT-TCA-GTA-CGT-ACT-AGT-CTA-CGT-CAC-CCG-CCC-CGT-TCC-3' (SEQ. ID. NO. 23). The resulting PCR fragment was digested with EcoRI and AscI and cloned into vector pNEB193 (New England Biolabs) digested with the same enzymes. The resulting construct was named pNEB/ITR-pIX. Sequencing confirmed correct amplification of the Ad5 sequences in the left ITR (Ad5 sequences 1 to 103) linked to the pIX promoter (Ad5 sequences 3511 to 3538) except for a single mismatch with the expected sequence according to GenBank (Accession No.: M73260/M29978), i.e., an extra C-residue was found just upstream of the AflII site. This ITR-pIX fragment was isolated with EcoRI and AflII and ligated to a EcoRI-AflII vector fragment containing Ad5 sequences 3539–21567. The latter fragment was obtained by digestion of pBr/Ad.Cla-Bam (supra) with EcoRI and partially with AflII. The resulting clone was named pAd/LITR(Δ5')-BamHI. The final construct pWE/Ad.Δ5' was made by ligating cosmid vector pWE15.Pac (supra) digested with PacI to pAd/LITR(A5')-BamHI digested with PacI-BamHI and pBr/Ad.Bam-rITR.pac#2 (supra) digested with PacI/BamHI (FIG. 25).

An alternative method to produce packaging systems for minimal adenoviral vectors without the use of helper viruses according to the invention is to use a replicating DNA molecule that contains the complete adenoviral genome except for the E1 region and the packaging signal and in which one of the ITRs is replaced by a fragment containing a DNA sequence complementary to a portion of the same strand other than the ITR and that therefore is able to form a hairpin structure (FIG. 10). In a non-limiting example, the DNA sequence complementary to a portion of the same strand other than the ITR is derived from the adeno-associated virus (AAV) terminal repeat. Such a replicating DNA molecule is made following the same cloning strategy as described for pWE/Ad.Δ5', but now starting with the AAV terminal repeat linked to part of the adenoviral pIX promoter. To this end, the adenoviral ITR sequences between the HpaI and SpeI sites in construct pNEB/ITR-pIX were exchanged for the AAV ITR by introducing the PvuII/XbaI fragment from psub201(+) containing the AAV ITR (Samulski et al., (1989) *T. Virol.* 63:3822–3828). This results in construct pWE/AAV.Δ5' that replicates in an E1 complementing cell line.

Another alternative packaging system for minimal adenoviral vectors is described infra and makes use of the replication system of SV40. A functional helper molecule according to this method contains at least the adenoviral sequences necessary to sustain packaging of a minimal construct but not the E1 sequences and packaging signal, and preferably also lacking ITRs. This adenovirus-derived entity has to be present on a vector that contains, besides the sequences needed for propagation in bacteria, an origin of replication from SV40 virus. Transfection of such a molecule together with the minimal adenoviral vector, described supra, into a packaging cell line (e.g., PER.C6) expressing, besides the E1 proteins, SV40 derived Large T antigen proteins, results in Large T-dependent replication of the adenovirus-derived helper construct. This replication leads to high levels of adenoviral proteins necessary for replication of the minimal adenoviral vector and packaging into virus particles. In this way, there is no sequence overlap that leads to homologous recombination between the minimal adenoviral vector construct and the helper molecule. In addition, there is no sequence overlap that leads to homologous recombination between the helper molecule and minimal adenoviral vector on the one side and the E1 sequence in the packaging cell on the other side.

Figure 26:
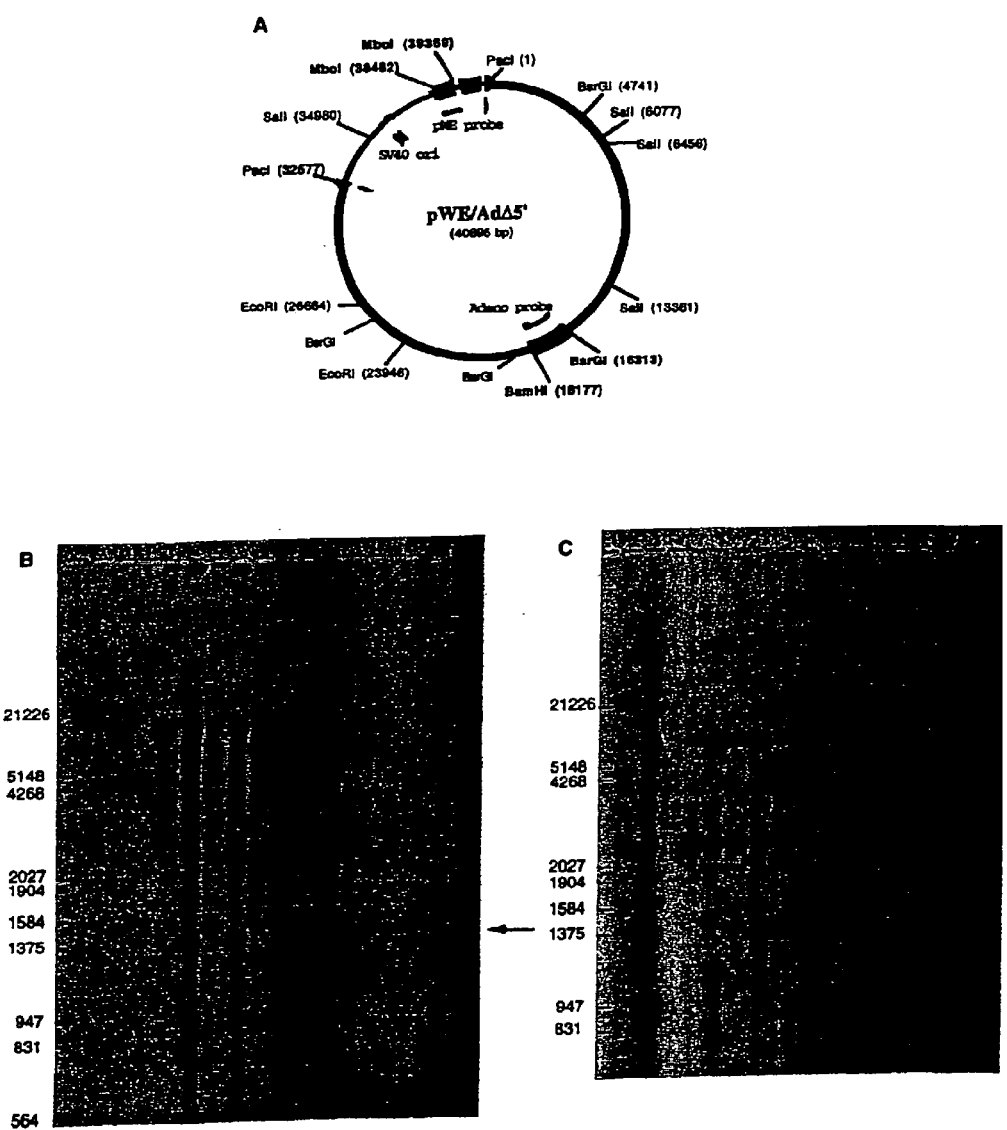
FIG. 26 provides evidence for SV40-LargeT/ori-mediated replication of large adenoviral constructs in Cos-1 cells. A) Schematic presentation of construct pWE/Ad.Δ5, and the location of the SV40 ori sequence and the fragments used to prepare probes. B) Autoradiogram of the Southern blot hybridized to the adenovirus probe. C) Autoradiogram of the Southern blot hybridized to the pWE probe. Lanes 1, marker lane: λ DNA digested with EcoRI and HindIII. Lane 4 is empty. Lanes 2, 5, 7, 9, 11, 13, 15 and 17 contain undigested DNA and Lanes 3, 6, 8, 10, 12, 14, 16 and 18 contain MboI digested DNA. All lanes contain DNA from Cos-1 cells as described in the text transfected with pWE.pac (lanes 2 and 3), pWE/Ad.Δ5' construct #1 (lanes 5 and 6), #5 (lanes 7 and 8) and #9 (lanes 9 and 10), pWE/Ad.AflII-rITR (lanes 11 and 12), pMV/CMV-LacZ (lanes 13 and 14), pWE.pac digested with PacI (lanes 15 and 16) or pWE/Ad.AflII-rITR digested with PacI (lanes 17 and 18). Arrows point at the expected positive signal of 1416 bp(B) and 887 bp (C).

Replication of a 40 kb adenoviral construct was investigated in cells expressing SV40 Large T proteins. Hereto, $2 \times 10^6$ Cos-1 cells were transfected in a T25 flask with the following constructs complexed with lipofectamine reagent (Life techn.): the 8 kb cosmid vector pWE.pac, the 40.5 kb construct pWE/Ad.AflII-rITR and three clones (#1, #5 and #9) of the 40.6 kb construct pWE/Ad.Δ5' (described infra). Control transfections were carried out with the constructs pWE.pac and pWE/Ad.AflII-rITR digested with PacI enzyme and a CMV-LacZ expression vector without the SV40 ori sequence. Transfection efficiency was 50% as determined by a separate transfection using the CMV-LacZ vector and X-gal staining after 48 hrs. All cells were harvested 48 hrs. following transfection and DNA was extracted according to the Hirt procedure (as described in Einerhand et al., (1995) *Gene Therapy* 2:336–343). Final pellets were resuspended in 50 μl TE+RNase (20 μg/ml) and 10 μl samples were digested with MboI (35 units overnight at 37° C.). Undigested samples (5 μl) and MboI digested samples were run on a 0.8% agarose gel, transferred to a nylon filter (Amersham) and hybridized to radioactive probes according to standard procedures. One probe was derived from an 887 bp DpnI fragment from the cosmid vector pWE.pac and one was derived from a 1864 bp BsxGI-BamHI fragment from adenoviral sequences. These probes hybridize to a 887 bp band and a 1416 bp respectively in MboI digested material. Input DNA from bacterial origin is methylated and therefore not digested with MboI. In this way it is possible to specifically detect DNA that is replicated in eukaryotic cells. FIG. 26A shows a schematic presentation of the construct pWE/Ad.Δ5' and the locations of the SV40 origin of replication, the pWE-derived probe and the adenovirus derived probe. The lower part presents the autoradiograms of the Southern blots hybridized to the adenovirus probe (B) and the pWE probe (C). (See, legends for explanation of sample loading). These experiments show that all lanes that contain material from Cos-1 cells that are transfected with plasmids harboring an SV40 ori contain MboI sensitive DNA and show a specific band of the expected length. The bands specific for replication in the lanes with Cos-1 cells transfected with PacI digested material (lanes B 17/18 and C 15–18) probably result from incomplete PacI digestion. From these experiments it can be concluded that it is possible to replicate large DNA fragments with the SV40 LargeT/ori system in eukaryotic cells.

Example 8

A functional adenovirus helper molecule lacking ITR sequences were constructed starting with the clone pWE/Ad.D5' described supra. pWE/Ad.D5' was digested with Bstl107I and the 17.5 kb vector-containing fragment was religated to give pWE/Ad.D5'-Bstl107I. This clone was then used to amplify the 3' part of the adenovirus genome sequences without the right ITR. A 2645 bp PCR fragment was generated using the primers Ad3'/Forw: 5'-CGG AAT TCA TCA GGA TAG GGC GGT GG-3' (SEQ. ID. NO. 24)and Ad3'/Rev: 5'-CGG GAT CCT ATC GAT ATT TAA ATG TTT TAG GGC GGA GTA ACT TG-3'(SEQ. ID. NO. 25). The amplified fragment was digested with EcoRI and BamHI and subcloned in pBr322 digested with the same enzymes. After confirmation of correct amplification by sequencing, the 2558 bp SbfI-ClaI fragment of this clone was recloned in pWE/Ad.D5'-Bstl107I digested with the same enzymes. The resulting construct lacks the right ITR and is named pWE/Δrl-Bstl107I. Next, in this clone the left ITR was replaced by a linker with a PacI and AflII overhang made up by annealing the following primers: PA-pIX1 5'-TAA GCC ACT AGT ACG TAC TGA AAT GTG TGG GCG TGG C-3'(SEQ. ID. NO. 26) and PA-pIX2 5'-TTA AGC CAC GCC CAC ACA TTT CAG TAC GTA CTA GTG GCT TAAT-3' (SEQ. ID. NO. 27). This removed the left ITR and restored correct sequence of the pIX promoter. The clone is named pWE/ΔITRBstl107I. Correct insertion of the double stranded linker was confirmed by sequencing. The deleted Bstl107I fragment was then cloned back into pWE/ΔITR-Bstl107I and the correct orientation was checked by restriction digestion. The resulting clone is named pWE/Ad-H. Following transfection of this DNA molecule into packaging cells that express adenoviral E1 proteins and the SV40 Large T antigen, replication of that molecule takes place resulting in high levels of adenoviral proteins encoded by the adenoviral entity on that molecule.

Example 9

Additional Modifications of Adapter Plasmids

To enable removal of vector sequences from the left ITR in pAd5/Clip (described in Example 2B), this plasmid was partially digested with EcoRI and the linear fragment was isolated. An oligo of the sequence 5'-TTAAGTCGAC-3' (SEQ. ID. NO. 28) was annealed to itself resulting in a linker with a SalI site and EcoRI overhang. The linker was ligated to the partially digested pAd5/Clip vector and clones were selected that had the linker inserted in the EcoRI site 23 bp upstream of the left adenoviral ITR in pAd5/Clip resulting in pAd5/Clipsal. Likewise, the EcoRI site in pAd5/Clip has been changed to a PacI site by insertion of a linker of the sequence 5'-AATTGTCTTAATTAACCGCAATT-3'(SEQ. ID. NO. 29) (as described in Example 2). The pAd5/Clip was partially digested with EcoRI, dephosphorylated and ligated to the PacI linker with EcoRI overhang. The ligation mixture was digested with PacI to remove concatamers, isolated from agarose gel and religated. The resulting vector was named pAd5/Clippac. These changes enable more flexibility to liberate the left ITR from the plasmid vector sequences.

The vector pAd5/L420-HSA was also modified to create a SalI or PacI site upstream of the left ITR. Hereto pAd5/L420-HSA was digested with EcoRI and ligated to the above described PacI linker. The ligation mixture was digested with PacI and religated after isolation of the linear DNA from agarose gel to remove concatamerised linkers. This resulted in adapter plasmid pAd5/L420-HSApac. This construct was used to generate pAd5/L420-HSAsal as follows: pAd5/L420-HSApac was digested with ScaI and BsrGI and the vector fragment was ligated to the 0.3 kb fragment isolated after digestion of pAd5/Clipsal with the same enzymes.

Generation of Adapter Plasmids AdMire and AdApt

To create an adapter plasmid that only contains a polylinker sequence and no promoter or polyA sequences, pAd5/L420-HSApac was digested with AvrII and BglII. The vector fragment was ligated to a linker oligonucleotide digested with the same restriction enzymes. The linker was made by annealing oligos of the following sequences:

PLL-1: 5'-GCC ATC CCT AGG AAG CTT GGT ACC GGT GAA TTC GCT AGC GTT AAC GGA TCC TCT AGA CGA GAT CTG G-3' (SEQ. ID. NO. 30) and PLL-2: 5'-CCA GAT CTC GTC TAG AGG ATC CGT TAA CGC

TAG CGA ATT CAC CGG TAC CAA GCT TCC TAG GGA TGG C-3' (SEQ. ID. NO. 31).

The annealed linkers were digested with AvrII and BglII and separated from small ends by column purification (Qiaquick nucleotide removal kit) according to manufacturers recommendations. The linker was then ligated to the AvrII/BglII digested pAd5/L420-HSApac fragment. A clone, named AdMire, was selected that had the linker incorporated and was sequenced to check the integrity of the insert.

Adapter plasmid AdMire enables easy insertion of complete expression cassettes.

An adapter plasmid containing the human CMV promoter that mediates high expression levels in human cells was constructed as follows: pAd5/L420-HSApac was digested with AvrII and 5' protruding ends were filled in using Klenow enzyme. A second digestion with HindIII resulted in removal of the L420 promoter sequences. The vector fragment was isolated and ligated to a PCR fragment containing the CMV promoter sequence. This PCR fragment was obtained after amplification of CMV sequences from pCMVLacI (Stratagene) with the following primers:

CMVplus: 5'-GATCGGTACCA CTGCAG TGG TCAATA TTGGCCATTAGCC-3' (SEQ. ID. NO. 32) and
CMVminA: 5'-GATC AAGCTT CCAATGCA CCGTTCCC GGC-3' (SEQ. ID. NO. 33).

The PCR fragment was first digested with PstI (underlined in CMVplus) after which the 3'-protruding ends were removed by treatment with T4 DNA polymerase. Then the DNA was digested with HindIII (underlined in CMVminA) and ligated into the above described pAd5/L420-HSApac vector fragment digested with AvrII and HindIII. The resulting plasmid was named pAd5/CMV-HSApac. This plasmid was then digested with HindIII and BamHI and the vector fragment was isolated and ligated to the polylinker sequence obtained after digestion of Admire with HindIII and BglII. The resulting plasmid was named AdApt. Adapter plasmid AdApt contains nucleotides −735 to +95 of the human CMV promoter (Boshart et al., 1985; M. Boshart, F. Weber, G. Jahn, K. Dorsch-Hasler, B. Fleckenstein and W. Schaffner. A very strong enhancer is located upstream of an immediate early gene of human CMV. *Cell* 41,521–530, (1985). A second version of this adapter plasmid containing a SalI site in place of the PacI site upstream of the left ITR was made by inserting the 0.7 kb ScaI-BsrGI fragment from pClipsal into AdApt digested with ScaI and partially digested with BsrGI. This clone was named AdApt-.sal.

Example 10

Modifications on Adenoviral Plasmids

Generation of pWE/Ad.AflII-rITRΔE2A:

Deletion of the E2A coding sequences from pWE/Ad.AflII-rITR (ECACC deposit P97082116) has been accomplished as follows. The adenoviral sequences flanking the E2A coding region at the left and the right site were amplified from the plasmid pBr/Ad.Sal.rITR (ECACC deposit P97082119) in a PCR reaction with the Expand PCR system (Boehringer) according to the manufacturers protocol. The following primers were used:

Right flanking sequences (corresponding Ad5 nucleotides 24033 to 25180):
ΔDE2A.SnaBI: 5'-GGC GTA CGT AGC CCT GTC GAA AG-3' (SEQ. ID. NO. 34)
ΔDE2A.DBP-start: 5'-CCA ATG CAT TCG AAG TAC TTC CTT CTC CTA TAG GC-3' (SEQ. ID. NO. 35)

The amplified DNA fragment was digested with SnaBI and NsiI (NsiI site is generated in the primer ΔDE2A.DBP-start, underlined).

Left flanking sequences (corresponding Ad5 nucleotides 21557 to 22442):
ΔDE2A.DBP-stop: 5'-CCA ATG CAT ACG GCG CAG ACG G-3' (SEQ. ID. NO. 36)
ΔDE2A.BamHI: 5'-GAG GTG GAT CCC ATG GAC GAG-3' (SEQ. ID. NO. 37)

The amplified DNA was digested with BamHI and NsiI (NsiI site is generated in the primer ΔDE2A.DBP-stop, underlined). Subsequently, the digested DNA fragments were ligated into SnaBI/BamHI digested pBr/Ad.Sal-rITR. Sequencing confirmed the exact replacement of the DBP coding region with a unique NsiI site in plasmid pBr/Ad.Sal-rITRΔDE2A. The unique NsiI site can be used to introduce an expression cassette for a gene to be transduced by the recombinant vector.

The deletion of the E2A coding sequences was performed such that the splice acceptor sites of the 100K encoding L4-gene at position 24048 in the top strand was left intact. In addition, the poly adenylation signals of the original E2A-RNA and L3-RNAs at the left hand site of the E2A coding sequences were left intact. This ensures proper expression of the L3genes and the gene encoding the 100K L4-protein during the adenovirus life cycle.

Next, the plasmid pWE/Ad.AflII-rITRΔDE2A was generated. The plasmid pBr/Ad.Sal-rITRΔDE2A was digested with BamHI and SpeI. The 3.9-Kb fragment in which the E2A coding region was replaced by the unique NsiI site was isolated. The pWE/Ad.AflII-rITR was digested with BamHI and SpeI. The 35 Kb DNA fragment, from which the BamHI/SpeI fragment containing the E2A coding sequence was removed, was isolated. The fragments were ligated and packaged using λ1 phage-packaging extracts according to the manufacturer protocol (Stratagene), yielding the plasmid pWE/Ad.AflII-rITRΔDE2A.

This cosmid clone can be used to generate adenoviral vectors that are deleted for E2A by cotransfection of PacI digested DNA together with digested adapter plasmids onto packaging cells that express functional E2A gene product. Examples of E2A complementing cell lines are described infra.

Generation of pWE/Ad.AflII-rITRsp

The 3' ITR in the vector pWE/Ad.AflII-rITR does not include the terminal G-nucleotide. Furthermore, the PacI site is located almost 30 bp from the right ITR. Both these characteristics may decrease virus generation efficiency due to inefficient initiation of replication at the 3' ITR. Note that during virus generation, the left ITR in the adapter plasmid is intact and enables replication of the virus DNA after homologous recombination.

To improve the efficiency of initiation of replication at the 3' ITR, the pWE/Ad.AflII-rITR was modified as follows: construct pBr/Ad.Bam-rITRpac#2 was first digested with PacI and then partially digested with AvrII and the 17.8 kb vector containing fragment was isolated and dephophorylated using SAP enzyme (Boehringer Mannheim). This fragment lacks the adenosequences from nucleotide 35464 to the 3'ITR. Using DNA from pWE/Ad.AflII-rITR as template and the primers ITR-EPH: 5'-CGG AAT TCT TAA TTA AGT TAA CAT CAT CAA TAA TAT ACC-3' (SEQ. ID. NO. 22) and Ad101: 5'-TGA TTC ACA TCG GTC AGT GC-3' (SEQ. ID. NO. 38). A 630 bp PCR fragment was generated corresponding to the 3' Ad5 sequences. This PCR fragment was subsequently cloned in the vector pCR2.1 (Invitrogen) and clones containing the PCR fragment were isolated and sequenced to check correct amplification of the DNA. The PCR clone was then digested with PacI and AvrII and the 0.5 kb adeno insert was ligated to the PacI/partial AvrII digested pBr/Ad.Bam-rITRpac#2 fragment generating pBr/Ad.Bam-rITRsp. Next this construct was used to generate a cosmid clone (as described in example 2) that has an insert corresponding to the adenosequences 3534 to 35938. This clone was named pWE/AflII-rITRsp.

Generation of Adenovirus Template Clones Lacking DNA Encoding for Fiber

Adenovirus infection is mediated by two capsid proteins fiber and penton. Binding of the virus to the cells is achieved by interaction of the protruding fiber protein with a receptor on the cell surface. Internalisation then takes place after interaction of the penton protein with integrins on the cell surface. At least some adenovirus from subgroup C and B have been shown to use a different receptor for cell binding and therefor have different infection efficiencies on different cell types. Thus it is possible to change the infection spectrum of adenoviruses by changing the fiber in the capsid. The fiber coding sequence of adenovirus serotype 5 is located between nucleotides 31042 and 32787. To remove the adenovirus serotype 5 DNA encoding fiber we started with construct pBr/Ad.Bam-rITR. First a NdeI site was removed from this construct. For this purpose, pBr322 plasmid DNA was digested with NdeI after which protruding ends were filled using Klenow enzyme. This pBr322 plasmid was then re-ligated, digested with NdeI and transformed into E. coli DH5α. The obtained pBr/ΔNdeI plasmid was digested with ScaI and SalI and the resulting 3198 bp vector fragment was ligated to the 15349 bp ScaI-SalI fragment derived from pBr/Ad.BamrITR, resulting in plasmid pBr/Ad.Bam-rITRΔNdeI which hence contained a unique NdeI site. Next a PCR was performed with oligonucleotides.

NY-up:
5'-CGA CAT ATG TAG ATG CAT TAG TTT GTG TTA TGT TTC AAC GTG-3' (SEQ. ID. NO. 39) and NY-down: 5'-GGA GAC CAC TGC CAT GTT-3' (SEQ. ID. NO. 40).

During amplification, both a NdeI (bold face) and a NsiI restriction site (underlined) were introduced to facilitate cloning of the amplified fiber DNAs. Amplification consisted of 25 cycles of each 45 sec. at 94° C., 1 min. at 60° C., and 45 sec. at 72° C. The PCR reaction contained 25 pmol of oligonucleotides NY-up or NY-down, 2 mM dNTP, PCR buffer with 1.5 mM $MgCl_2$, and 1 unit of Elongase heat stable polymerase (Gibco, The Netherlands). One-tenth of the PCR product was run on an agarose gel which demonstrated that the expected DNA fragment of ±2200 bp was amplified. This PCR fragment was subsequently purified using Geneclean kit system (Bio101 Inc.). Then, both the construct pBr/Ad.Bam-rITRΔNdeI as well as the PCR product were digested with restriction enzymes NdeI and SbfI. The PCR fragment was subsequently cloned using T4 ligase enzyme into the NdeI and SbfI digested pBr/Ad.Bam-rITRΔNdeI, generating pBr/Ad.BamRΔDFib.

This plasmid allows insertion of any PCR amplified fiber sequence through the unique NdeI and NsiI sites that are inserted in place of the removed fiber sequence. Viruses can be generated by a double homologous recombination in packaging cells described infra using an adapter plasmid, construct pBr/Ad.AflII-EcoRI digested with PacI and EcoRI and a pBr/Ad.BamRΔDFib construct in which heterologous fiber sequences have been inserted. To increase the efficiency of virus generation, the construct pBr/Ad.BamRΔDFib was modified to generate a PacI site flanking the right ITR. Hereto, pBr/Ad.BamRΔDFib was digested with AvrII and the 5 kb adenofragment was isolated and introduced into the vector pBr/Ad.Bam-rITR.pac#8 (described in Example 2) replacing the corresponding AvrII fragment. The resulting construct was named pBr/Ad.BamRΔDFib.pac.

Once a heterologous fiber sequence is introduced in pBr/Ad.BamRΔDFib.pac, the fiber modified right hand adenovirus clone may be introduced into a large cosmid clone as described for pWE/Ad.AflII-rITR in Example 2. Such a large cosmid clone allows generation of adenovirus by only one homologous recombination making the process extremely efficient.

Generation of Adenovirus Clones Lacking DNA Encoding Hexon

A major limitation for gene therapy approaches using Ad5-based recombinant adenoviruses is the presence of neutralizing antibodies in human serum. As much as 80–90% of individuals contain neutralizing immunity to Ad5. The majority of the neutralizing antibodies is directed to the hexon protein. Hexon proteins from different serotypes show highly variable regions present in loops that are predicted to be exposed at the outside of the virus (Athappilly et al., 1994; *J. Mol. Biol.*, 242, 430–455). Most type specific epitopes have been mapped to these highly variable regions (Toogood et al., 1989; *J. Gen Virol.*, 70, 3203–3214). Thus replacement of (or part of) the hexon sequences with corresponding sequences from a different serotype is an effective strategy to circumvent (pre-existing) neutralizing antibodies to Ad5. Hexon coding sequences of adenovirus serotype 5 are located between nucleotides 18841 and 21697.

To facilitate easy exchange of hexon coding sequences from alternative adenovirus serotypes into the adenovirus serotype 5 backbone, first a shuttle vector was generated. This subclone, coded pBr/Ad.Eco-PmeI, was generated by first digesting plasmid pBr322 with EcoRI and EcoRV and inserting the 14 kb PmeI-EcoRI fragment from pWE/Ad.AflII-Eco. In this shuttle vector a deletion was made of a 1430 bp SanDI fragment by digestion with SanDI and religation to give pBr/Ad.Eco-PmeI ΔSanDI. The removed fragment contains unique SpeI and MunI sites. From pBr/Ad.Eco-PmeIADSanDI the adenovirus serotype 5 DNA encoding hexon was deleted. Hereto, the hexon flanking sequences were PCR amplified and linked together thereby generating unique restriction sites replacing the hexon coding region. For these PCR reactions four different oligonucleotides were required: ΔDhexl–ΔDhex4.

ΔDhex1: 5'-CCT GGT GCT GCC AAC AGC-3' (SEQ. ID. NO. 41)
ΔDhex2: 5'-CCG GAT CCA CTA GTG GAA AGC GGG CGC GCG-3' (SEQ. ID. NO. 42)
ΔDhex3: 5'-CCC GAT CCA ATT GAG AAG CAA GCA ACA TCA ACA AC-3' (SEQ. ID. NO. 43)
ΔDhex4: 5'-GAG AAG GGC ATG GAG GCT G-3' (SEQ. ID. NO. 44)

The amplified DNA product of ±1100 bp obtained with oligonucleotides ΔDhexl and ΔDhex2 was digested with BamHI and FseI. The amplified DNA product of ±1600 bp obtained with oligonucleotides ΔDhex3 and ΔDhex4 was digested with BamHI and SbfI. These digested PCR fragments were subsequently purified from agarose gel and in a tri-part ligation reaction using T4 ligase enzyme linked to pBr/Ad.Eco-PmeI ΔDSanDI digested with FseI and SbfI. The resulting construct was coded pBr/Ad.Eco-PmeΔDHexon. This construct was sequenced in part to confirm the correct nucleotide sequence and the presence of unique restriction sites MunI and SpeI.

pBr/Ad.Eco-PmeΔDHexon serves as a shuttle vector to introduce heterologous hexon sequences amplified from virus DNA from different serotypes using primers that introduce the unique restriction sites MunI and SpeI at the 5' and 3' ends of the hexon sequences respectively. The hexon modified sequences are subsequently introduced in the construct pWE/Ad.AflII-rITR by exchange of the AscI fragment generating pWE/Ad.AflII-rITRHexXX where XX stands for the serotype used to amplify hexon sequences.

Generation of Adenoviral Clones Lacking DNA Encoding Penton

The Ad5 penton gene is located between sequences 14156 and 15869. Penton base is the adenoviral capsid protein that mediates internalisation of the virus into the target cell. At least some serotypes (type C and B) have been shown to achieve this by interaction of an RGD sequence in penton with integrins on the cell surface. However, type F adenoviruses do not have an RGD sequence and for most viruses of the A and D group the penton sequence is not known. Therefor, penton may be involved in target cell specificity. Furthermore, as a capsid protein, the penton protein is involved in the immunogenicity of the adenovirus. Individuals, including patients that are candidates for gene therapy approaches, may have pre-existing antibodies directed to penton proteins in their serum. The replacement of Ad5 penton sequences with penton sequences from certain other serotypes therefor, will affect infection specificity as well as immunogenicity of the virus. To be able to introduce heterologous penton sequences in Ad5 we made use of the plasmid-based system described infra. First a shuttle vector for penton sequences was made by insertion of the 7.2 kb NheI-EcoRV fragment from construct pWE/Ad.AflII-EcoRI (described in Example 2) into pBr322 digested with the same enzymes. The resulting vector was named pBr/XN. From this plasmid Ad5 penton sequences were deleted and replaced by unique restriction sites that are then used to introduce new penton sequences from other serotypes. Hereto, the left flanking sequences of penton in pBr/XN were PCR amplified using the following primers:

DP5-F: 5'-CTG TTG CTG CTG CTA ATA GC-3' (SEQ. ID. NO. 45)and

DP5-R: 5'-CGC <u>GGA TCC</u> TGT ACA ACT AAG GGG AAT ACA AG-3' (SEQ. ID. NO. 46)

DP5-R has an BamHI site (underlined) for ligation to the right flanking sequence and also introduces a unique BsrGI site (bold face) at the 5'-end of the former Ad5 penton region.

The right flanking sequence was amplified using:

DP3-F: 5'-CGC GGA TCC CTT AAG GCA AGC ATG TCC ATC CTT-3' (SEQ. ID. NO. 47)and

DP3-3R: 5'-AAA ACA CGT TTT ACG CGT CGA CCT TTC-3' (SEQ. ID. NO. 48)

DP3-F has an BamHI site (underlined) for ligation to the left flanking sequence and also introduces a unique AflII site (bold face) at the 3'-end of the former Ad5 penton region.

The two resulting PCR fragments were digested with BamHI and ligated together. Then this ligation mixture was digested with AvrII and BglII. pBr/XN was also digested with AvrII and BglII and the vector fragment was ligated to the digested ligated PCR fragments. The resulting clone was named pBr/Ad.ΔDpenton. Penton coding sequences from serotypes other than Ad5 were PCR amplified such that the 5' and 3' ends contained the BsrGI and AflII sites respectively. Introduction of these heterologous penton sequences in pBr/Ad.ΔDpenton generates constructs named pBr/Ad.pentonXX where XX represents the number of the serotype corresponding to the serotype used to amplify the inserted penton sequences. Subsequently the new penton sequences were introduced in the pWE/Ad.AflII-rITR construct by exchanging the common FseI fragment. Importantly, in stead of pWE/Ad.AflII-rITR it is also possible to insert the FseI fragment from pBr/Ad.pentonXX into a pWE/Ad.AflllI-rITR vector having a modified hexon and/or fiber sequence. In this way, the plasmid-based system to generate adenoviruses enables flexible design of any adenovirus with any desired characteristic concerning efficiency and specificity of infection of the target cell as well as immunogenicity.

Example 11

Generation of Replicating Viruses

The plasmid-based system to generate recombinant adenoviruses described infra is also very well suited to generate replicating viruses. Replicating viruses may be used for gene therapy approaches aimed at eradicating tumor cells. For example, suicide gene therapy methods using replicating adenoviruses that express the HSV-tk gene may have improved efficacy due to increased spread of the vector. Safety is ensured by the possibility to block replication at any time by administration of ganciclovir.

Replicating viruses expressing HSV-tk or a marker gene have been generated with the double homologous recombination system described in Example 2. Hereto, the following constructs are transfected onto packaging cells:

pBr/Ad.lITR-SalI(9.4), digested with EcoRI and SalI to liberate the adeno insert from the vector sequences.

pWE/Ad.AflII-EcoRI digested with PacI and EcoRI pBr/Ad.Bam-rITRΔDgp19K/luc$^2$ or pBr/Ad.Bam-rITRΔDgp19K/TK digested with SalI, wherein the third construct is a derivative of the pBr/Ad.Bam-rITR construct that is made by replacement of the gp19K coding region with either a marker gene (luciferase) or the HSV-tk gene as described in example 2 for E1-deleted viruses with modifications in the E3 region. In stead of pBr/Ad.Bam-rITR, the modification of the E3 region may also be introduced in pBr/Ad.Bam-rITRpac#2 or #8, or in pBr/Ad.Bam-rITRsp. This enables liberation of the right ITR from the vector sequences by digestion with PacI and increases the efficiency by which viruses are generated.

Example 12

Generation of Recombinant Viruses Using the Described Plasmid-Based System is Extremely Efficient and Reliable Several methods have been described previously for generating recombinant adenoviruses. One of these methods makes use of a circular large adenoviral plasmid that is Co-transfected on packaging cells with a linearised adapter plasmid (Bett et al., 1994). The efficiency of this method is low due to the fact that the ITRs are linked head to head in the large adenoviral plasmid. Other methods make use of a recombination step in specialised bacteria that lead to a recombinant viral DNA clone (Chartier et al., 1996; Crouzet et al., 1997; He et al., 1998). After restriction analysis of the clones and selection of correct recombinants a different strain of bacteria has to be transformed to make a large batch of the DNA. Then linearised fragments are transfected in packaging cells and recombinant viruses appear within a week following transfection.

The plasmid system described infra differs from the methods described above. The system combines easy manipulation of small adapter plasmids in standard bacteria with efficient homologous recombination in packaging cells due to linearised large adenoviral plasmids.

The high efficiency of homologous recombination in E1-complementing packaging cells is exemplified by the experiment described below.

A 96-well microtiter tissue culture plate (plate 1) (Greiner, The Netherlands, catalogue #6555180) was first coated with poly-L-lysine (PLL, 0.1 mg/ml) (Sigma) dissolved in sterile water by incubating each well for 20–120 minutes at room temperature. Alternatively, pre-coated 96-well plates can be used (Becton and Dickinson). After the incubation with PLL, each well was washed two times with 100 µl sterile water and dried at room temperature for at least two hours. The day before transfection PER.C6 cells were harvested using trypsin-EDTA and counted. The cells were then diluted to a suspension of 45,000 cells per 100 µl followed by seeding 100 µl per well of the PLL coated 96-well plates. The next day 2.6 ⊟l of Sal I linearized pAd/CMV-LacZ and 2.6 µl of PacI linearized pWE-Ad.AflII-rITR plasmid DNA (both 1 µg/1 ml) and 95 µl serum free DMEM were mixed with 25.6 µl lipofectamine diluted in 74.4 µl serum free DMEM by adding the lipofectamine to the DNA mix. The DNA/lipofectamine mixture was left at room temperature for 30 minutes after which 1.3 ml serum free media was added. The latter mixture was then added (30 µl per well) to PER.C6 seeded wells that were washed with 200 µl DMEM prior to transfection. After 3 hours in a humidified $CO_2$ incubator (370C, 10% $CO_2$) 200 µl DMEM with 10% FCS 10 MM $MgCl_2$ was added to each well and the plates were returned to the humidified $CO_2$ incubator (37° C., 10! $CO_2$). The next day the medium of each well was replaced with 200 µl DMEM, 10% FCS, 10 mM $MgCl_2$. The plates were then left in the humidified $CO_2$ incubator for an additional three days after which the wells were subjected to freezing at −20° C. for at least 1 hour followed by thawing and resuspension by repeated pipetting. Transfection efficiency was determined using lacZ staining in additional plates and found to be approximately 40% for each transfected well of PER.C6 cells. An aliquot of 100 µl of freeze/thawed transfected cells was transferred to each well of a plate with new PER.C6 cells seeded as described above without PLL coated plates (plate 2). The second 96-well plate with PER.C6 cells incubated with freeze/thaw cell lysate of the first transfected plate was checked for CPE. At least 5% of the wells showed clear CPE after 2 days. Four days after infection with the lysate from plate 1 the plate was subjected to one freeze-thaw cycle and 10 1 µl from each lysed well was added to wells of a plate seeded with A549 cells ($1\times10^4$ cells per well seeded in 100 µl in DMEM, 10% FCS the day before). Two days after infection the wells were stained for lacZ activity. Of the infected wells 96% were infected and stained blue. All wells stained and a large number of wells showed 100% blue staining and thus transduction of all cells with adenoviral vector carrying lacZ. Extrapolated from MOI experiments in tissue culture flasks the adenoviral titer of well-produced virus is around $10^6$–$10^7$ infectious units per ml.

From the high percentage of wells that contain LacZ virus we concluded that the plasmid-based system for generating adenoviruses described infra is very efficient.

In addition to highly efficient, the system is also very reliable. Using the routine procedure of virus generation as described in example 2 (section C) we obtain a T80 flask with adenovirus infected cells showing full CPE. Different stocks of viruses obtained after cotransfection with adapter plasmids carrying different transgenes (Luciferase, LacZ, ratIL-3, humanIL1 αa, HSV1-TK, ceNOS, hgp100) and different promoters (MLP, CMV, E3 or retroviral LTR) in a total of 16 transfections, were subjected to plaque purification and separate plaques were tested for expression of the transgene. Out of a total of 145 plaques only two were found to be negative. When positive plaques from the first plaque purification were subjected to a second round of plaque purification all tested plaques were found to be positive (144 out of 144 tested). This clearly shows that the plasmid-based system of the invention is very reliable.

Example 13

Generation of Minimal Adenoviral Vectors with Large Inserts

In Examples 7 and 8, methods are described for producing minimal adenoviral vectors in E1-expressing packaging cells. The minimal vectors described here only contain an expression cassette for a gene of interest and the adenoviral ITRs and packaging sequences. Efficient packaging of adenoviruses requires a genome length of >27 kb (Parks and Graham, 1997; J. Virol. 71, 3293–3298). Therefore, to be able to produce high titers of minimal adenoviruses it is necessary to include stuffer DNA in the vectors to reach the optimal packaging size. In case one designs a gene correction vector it is possible or even necessary to include a large fragment of genomic DNA homologous to the genome site to be targeted. In other cases the gene of interest may not be large enough to fulfill the packaging size and a stuffer has to be included. Here we describe the construction of larger minimal vectors with stuffer DNA and a method to produce such vectors.

The vectors pMV/L420H (FIG. 24) and pMV/CMV-LacZ were first modified to create a second NotI site flanking the left ITR. Hereto, pMV/L420H was partially digested with EcoRI and the linear fragment was isolated. This fragment was ligated to a double stranded linker obtained by annealing an oligonucleotide of the sequence 5'-AATTGCGGCCGC-3' (SEQ. ID. NO. 49). A clone was selected which had the NotI linker inserted in the correct EcoRI site. This clone was named pMV/L420H.nn. Next pMV/CMV-LacZ was digested with ScaI and BsrGI and the 7 kbp fragment lacking part of the Amp gene and adenoviral ITR was isolated. This fragment was then ligated to the 0.7 kbp ScaI-BsrGI fragment from pMV/L420H.nn. This resulted in pMV/CMV-LacZ.nn. In both minimal vectors pMV/L420H.nn and pMV/CMV-LacZ.nn, the ITRs are flanked by a NotI site. Since the vector backbone is a cosmid vector based on pWE15 these clones can be used to insert large fragments of stuffer DNA. Stuffer inserts can be any piece of DNA that contains no active transcription regions. Alternatively, the described minimal vectors can be used to insert a large fakement of genomic DNA. In case a marker gene is not required, the insertion can be such that the expression cassette for the HSA gene or the LacZ gene is replaced by the genomic fragment by making use of the SnaBI of AvrII site at the 5' end of the expression cassette and the unique sites at the 3' end.

One example of a suitable stuffer DNA is a part of the $44^{th}$ intron of the human Dysthrophin genomic DNA (Genbank accession code: M86524). The generation of large cosmid clones containing the above described minimal adenoviral vectors and 31.7 kb of the dystrophin intron sequence are described below. Hereto the dystrophin sequence is digested with XhoI and BstBI and the 31.7 kb fragments is isolated. Part of the fragment is left with sticky ends and part is filled in with Klenow. Then pMV/L420H.nn is digested with XhoI and ClaI and ligated to the dystrophin fragment with sticky ends. pMV/CMV-LacZ.nn is digested with XhoI, blunted with Klenow enzyme and ligated to the blunted dystrophin fragment. Both ligations are packaged as described before. The large clones generated in this way tend to be unstable in bacteria probably due to the large insert and the presence of two ITRs of adenovirus. An improved method to generate these large minimal vectors is described hereinafter. This method makes use of the powerful system of homologous recombination in packaging cells for generating recombinant viruses.

Generation of minimal adenoviral vectors by homologous recombination in packaging cells.

pMV/CMV-LacZ.nn was digested with XhoI and NsiI and the ends were blunted with T4 DNA polymerase. The linear fragment is isolated and ligated to the approximately 17.5 kbp XhoI/KpnI fragment from the dystrophin intron also blunted with T4 DNA polymerase. Clones were selected that contained the dystrophin fragment in the 5' to 3' direction. This clone, named pMV/CMV-LacZ.Dys5' contains the left ITR and packaging signal of adenovirus in addition to the LacZ expression cassette and the 5' part of the dystrophin insert. A second clone was then made by digestion of pMV/CMV-LacZ.nn with BglII. The linear fragment was then partially digested with NotI and the 6.4 kb vector fragment was blunted with Klenow and isolated. This fragment was then ligated to the 18.8 kb PvuI-BstBI dystrophin fragment blunted with T4 DNA polymerase. Clones were selected that contained the dystrophin fragment in the 5' to 3' direction. This clone, named pMV/Dys3'-ITR contains a dystrophin insert that has 4.5 kb overlap with the dystrophin fragment in pMV/CMV-LacZ.Dys5'.

Minimal adenoviral vectors containing the full length 31.7 kb XhoI-BstBI fragment are generated by cotransfection of adenovirus packaging cells (e.g., PER.C6) with pMV/CMV-LacZ.Dys5' and pMV/Dys3' with an adenoviral helper plasmid as described in this invention, for example, pWE/Ad.DS' or pWE/AdH and a SV40. LargeT expression construct (see, Examples 7 and 8). Hereto, the pMV/CMV-LacZ.Dys5' construct is digested with NotI and BstBI and the pMV/Dys3' is digested with NotI and PvuI to liberate the ITRs from the vector sequences and to minimize the amount of vector DNA attached to the dystrophin insert thereby enabling homologous recombination and replication.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now having been fully described, it will be apparent to one of ordinary skill in the art that many changes and modifications can be made thereto without departing from the spirit or scope of the appended claims.

TABLE I

Primers used for PCR amplification of DNA fragments used for generating constructs described in this patent application

| | | |
|---|---|---|
| Ea-1 | CGTGTAGTGTATTTATACCCG (SEQ. ID. NO. 50) | PCR amplification Ad5 nt. 459 ® |
| Ea-2 | TCGTCACTGGGTGGAAAGCCA (SEQ. ID. NO. 51) | PCR amplification Ad5 nt. 960 ← |
| Ea-3 | TACCCGCCGTCCTAAAATGGC (SEQ. ID. NO. 52) | nt. 1284–1304 of Ad5 genome |
| Ea-5 | TGGACTTGAGCTGTAAACGC (SEQ. ID. NO. 53) | nt. 1514–1533 of Ad5 genome |
| Ep-2 | GCCTCCATGGAGGTCAGATGT (SEQ. ID. NO. 54) | nt. 1721–1702 of Ad5; introduction of NcoI site |
| Eb-1 | GCTTGAGCCCGAGACATGTC (SEQ. ID. NO. 55) | nt. 3269–3289 of Ad5 genome |
| Eb-2 | CCCCTCGAGCTCAATCTGTATCTT (SEQ. ID. NO. 56) | nt. 3508–3496 of Ad5 genome; introduction of XhoI site |
| SV40-1 | GGGGGATCCGAACTTGTTTATTGCAGC (SEQ. ID. NO. 57) | introduction BamHI site (nt. 2182–2199 of pMLP.TK) adaptation of recombinant adenoviruses |
| SV40-2 | GGGAGATCTAGACATGATAAGATAC (SEQ. ID. NO. 58) | introduction BglII site (nt. 2312–2297 of pMLP.TK) |
| Ad5-1 | GGGAGATCTGTACTGAAATGTGTGGGC (SEQ. ID. NO. 59) | introduction BglII site (nt. 2496–2514 of pMLP.TK) |
| Ad5-2 | GGAGGCTGCAGTCTCCAACGGCGT (SEQ. ID. NO. 60) | nt. 2779–2756 of pMLP.TK |
| ITR1 | GGGGGATCCTCAAATCGTCACTTCCGT (SEQ. ID. NO. 61) | nt. 35737–35757 of Ad5 (introduction of BamHI site) |
| ITR2 | GGGGTCTAGACATCATCAATAATATAC (SEQ. ID. NO. 62) | nt. 35935–35919 of Ad5 (introduction of XbaI site) |

PCR primer sets to be used to create the SalI and Asp718 sites juxtaposed to the ITR sequences.

| | |
|---|---|
| PCR/MLP1 | GGCGAATTCGTCGACATCATCAATAATATACC (SEQ. ID. NO. 63) (Ad5 nt. 10–18) |
| PCR/MLP2 | GGCGAATTCGGTACCATCATCAATAATATACC (SEQ. ID. NO. 64) (Ad5 nt. 10–18) |
| PCR/MLP3 | CTGTGTACACCGGCGCA (SEQ. ID. NO. 65) (Ad5 nt. 200–184) |

Synthetic oligonucleotide pair used to generate a synthetic hairpin, recreates an Asp718 site at one of the termini if inserted in Asp718 site:

| | |
|---|---|
| HP/asp1 | 5'-GTACACTGACCTAGTGCCGCCCGGGAAAGCCCGGGCGGCACTAGGTCAG (SEQ. ID. NO. 66) |
| HP/asp2 | 5'-GTACCTGACCTAGTGCCGCCCGGGCTTTGCCCGGGCGGCACTAGGTCAGT (SEQ. ID. NO. 67) |

Synthetic oligonucleotide pair used to generate a synthetic hairpin, contains the ClaI recognition site to be used for hairpin formation.

| | |
|---|---|
| HP/cla1 | 5'-GTACATTGACCTAGTGCCGCCCGGGCAAAGCCCGGGCGGCACTAGGTCAATCGAT (SEQ. ID. NO. 68) |
| HP/cla2 | 5'-GTACATCGATTGACCTAGTGCCGCCCGGGTTTGCCCGGGCGGCACTAGGTCAAT (SEQ. ID. NO. 69) |

TABLE II

Production of recombinant adenoviral vector or different packages, cell lines

| | | Yields × $10^{-8}$ pfu/T175 flask.[1] | | | | Producer |
|---|---|---|---|---|---|---|
| Cell | Passage Number | IGAd.CMV.lacZ | IG.Ad.CMV.TK | IG.Ad.MLPI.TK | d1313 | Mean |
| 293 | | 6.0 | 5.9 | 24 | 34 | 17.5 |
| 911 | | 8 | 14 | 34 | 180 | 59.5 |
| PER.C3 | 17 | 8 | 11 | 44 | 40 | 25.8 |
| PER.C5 | 15 | 6 | 17 | 36 | 200 | 64.7 |
| PER.C6 | 36 | 10 | 22 | 58 | 320 | 102 |

NOTE: The yields are the mean of two different experiments. IG.Ad.CMV.lacZ and IG.Ad.CMV.TK are described in EPO patent application EP 95202213. The construction of IG.Ad.MLPI.TK is described in this patent application. Yields of virus per T80 flask were determined by plaque assay on 911 cells, as described (Fallaux et al (1996) Hum. Gene. Ther. 7: 215–222). #1493).

TABLE III

Double insert viruses with different transgenes replacing the
E1 and E3/gp19K regions express both transgenes in human A549 cells

| Virus[1] | Amount | % of cells with HSA expression | Luciferase activity (light units) |
|---|---|---|---|
| IGAd/CMV-Luc | $5 \times 10^7$ i.u. | ND | 25,726,074 |
|  | $2.5 \times 10^7$ i.u. | ND | 7,996,542 |
| IGAd/S1800-HSA | 100 µl ccl | 88% | ND |
|  | 50 µl ccl | 82% | ND |
| IGAd/S1800-HAS.E3luc | $1.2 \times 10^7$ i.u. | 97% | 32,451,300 |
|  | $6 \times 10^7$ i.u. | 97% | 24,716,586 |
|  | $1.2 \times 10^8$ i.u. | 100% | 13,294,321 |

NOTE: All virus preps were clarified crude cell lysates (ccl). A clarified crude cell lysate was made by harvesting cells with medium at full CPE followed by three freeze/thaw cycles. pAd/S1800-HSA was not titrated.

SEQUENCE LISTING

<160> NUMBER OF SEQ ID NOS: 69

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: oligo
      linker
<221> NAME/KEY: misc_feature
<222> LOCATION: (1)..(23)
<223> OTHER INFORMATION: /Note="linker with PacI site"

<400> SEQUENCE: 1
aattgtctta attaaccgct taa                                              23

<210> SEQ ID NO 2
<211> LENGTH: 19
<212> TYPE: DNA
<213> ORGANISM: Artificial Sequence
<220> FEATURE:
<221> NAME/KEY: misc_feature
<222> LOCATION: (1)..(19)
<223> OTHER INFORMATION: /Note="linker with Pac site"
<223> OTHER INFORMATION: Description of Artificial Sequence: oligo
      linker

<400> SEQUENCE: 2
aattgtctta attaaccgc                                                   19

<210> SEQ ID NO 3
<211> LENGTH: 19
<212> TYPE: DNA
<213> ORGANISM: Artificial Sequence
<220> FEATURE:
<221> NAME/KEY: misc_feature
<222> LOCATION: (1)..(19)
<223> OTHER INFORMATION: /Note="linker with Pac site"
<223> OTHER INFORMATION: Description of Artificial Sequence: oligo
      linker

<400> SEQUENCE: 3
aattgcggtt aattaagac                                                   19

<210> SEQ ID NO 4
<211> LENGTH: 47

```
<212> TYPE: DNA
<213> ORGANISM: Artificial Sequence
<220> FEATURE:
<221> NAME/KEY: primer_bind
<222> LOCATION: (1)..(47)
<223> OTHER INFORMATION: /Note="primer LTR-1"
<223> OTHER INFORMATION: Description of Artificial Sequence:primer

<400> SEQUENCE: 4
ctgtacgtac cagtgcactg gcctaggcat ggaaaaatac ataactg                47

<210> SEQ ID NO 5
<211> LENGTH: 64
<212> TYPE: DNA
<213> ORGANISM: Artificial Sequence
<220> FEATURE:
<221> NAME/KEY: primer_bind
<222> LOCATION: (1)..(64)
<223> OTHER INFORMATION: /Note="primer LTR-2"
<223> OTHER INFORMATION: Description of Artificial Sequence: primer

<400> SEQUENCE: 5
gcggatcctt cgaaccatgg taagcttggt accgctagcg ttaaccgggc gactcagtca    60
atcg                                                                64

<210> SEQ ID NO 6
<211> LENGTH: 28
<212> TYPE: DNA
<213> ORGANISM: Artificial Sequence
<220> FEATURE:
<221> NAME/KEY: primer_bind
<222> LOCATION: (1)..(28)
<223> OTHER INFORMATION: /Note="primer HSA1"
<223> OTHER INFORMATION: Description of Artificial Sequence: primer

<400> SEQUENCE: 6
gcgccaccat gggcagagcg atggtggc                                      28

<210> SEQ ID NO 7
<211> LENGTH: 50
<212> TYPE: DNA
<213> ORGANISM: Artificial Sequence
<220> FEATURE:
<221> NAME/KEY: primer_bind
<222> LOCATION: (1)..(50)
<223> OTHER INFORMATION: /Note="primer HSA2"
<223> OTHER INFORMATION: Description of Artificial Sequence: primer

<400> SEQUENCE: 7
gttagatcta agcttgtcga catcgatcta ctaacagtag agatgtagaa               50

<210> SEQ ID NO 8
<211> LENGTH: 21
<212> TYPE: DNA
<213> ORGANISM: Artificial Sequence
<220> FEATURE:
<221> NAME/KEY: primer_bind
<222> LOCATION: (1)..(21)
<223> OTHER INFORMATION: /Note="primer 1"
<223> OTHER INFORMATION: Description of Artificial Sequence: primer

<400> SEQUENCE: 8
gggtattagg ccaaaggcgc a                                             21

<210> SEQ ID NO 9
<211> LENGTH: 33
<212> TYPE: DNA
<213> ORGANISM: Artificial Sequence
```

<220> FEATURE:
<221> NAME/KEY: primer_bind
<222> LOCATION: (1)..(33)
<223> OTHER INFORMATION: /Note="primer 2"
<223> OTHER INFORMATION: Description of Artificial Sequence: primer

<400> SEQUENCE: 9
gatcccatgg aagcttgggt ggcgacccca gcg                         33

<210> SEQ ID NO 10
<211> LENGTH: 36
<212> TYPE: DNA
<213> ORGANISM: Artificial Sequence
<220> FEATURE:
<221> NAME/KEY: primer_bind
<222> LOCATION: (1)..(36)
<223> OTHER INFORMATION: /Note="primer 3"
<223> OTHER INFORMATION: Description of Artificial Sequence: primer

<400> SEQUENCE: 10
gatcccatgg ggatccttta ctaagttaca aagcta                      36

<210> SEQ ID NO 11
<211> LENGTH: 19
<212> TYPE: DNA
<213> ORGANISM: Artificial Sequence
<220> FEATURE:
<221> NAME/KEY: primer_bind
<222> LOCATION: (1)..(19)
<223> OTHER INFORMATION: /Note="primer 4"
<223> OTHER INFORMATION: Description of Artificial Sequence: primer

<400> SEQUENCE: 11
gtcgctgtag ttggactgg                                         19

<210> SEQ ID NO 12
<211> LENGTH: 25
<212> TYPE: DNA
<213> ORGANISM: Artificial Sequence
<220> FEATURE:
<221> NAME/KEY: primer_bind
<222> LOCATION: (1)..(25)
<223> OTHER INFORMATION: /Note="primer"
<223> OTHER INFORMATION: Description of Artificial Sequence: primer

<400> SEQUENCE: 12
cgataagctt aattcctttg tgttt                                  25

<210> SEQ ID NO 13
<211> LENGTH: 33
<212> TYPE: DNA
<213> ORGANISM: Artificial Sequence
<220> FEATURE:
<221> NAME/KEY: primer_bind
<222> LOCATION: (1)..(33)
<223> OTHER INFORMATION: /Note="primer"
<223> OTHER INFORMATION: Description of Artificial Sequence: primer

<400> SEQUENCE: 13
cttaggtaac ccagtagatc cagaggagtt cat                         33

<210> SEQ ID NO 14
<211> LENGTH: 45
<212> TYPE: DNA
<213> ORGANISM: Artificial Sequence
<220> FEATURE:
<221> NAME/KEY: misc_feature
<222> LOCATION: (1)..(45)
<223> OTHER INFORMATION: /Note="hac, haw Potential hairpin that can be

```
                formed after digestion with restriction
                endonuclease Asp7I8 in both the correct and in the
                reverse orientation, respectively"
<223> OTHER INFORMATION: Description of Artificial Sequence: synthetic
      DNA sequence

<400> SEQUENCE: 14
gtacactgac ctagtgccgc ccgggcaaag cccgggcggc actag          45

<210> SEQ ID NO 15
<211> LENGTH: 63
<212> TYPE: DNA
<213> ORGANISM: Artificial Sequence
<220> FEATURE:
<221> NAME/KEY: primer_bind
<222> LOCATION: (1)..(63)
<223> OTHER INFORMATION: /Note="primer polyL-ITR"
<223> OTHER INFORMATION: Description of Artificial Sequence: primer

<400> SEQUENCE: 15
aactgcagat ctatcgatac tagtcaattg ctcgagtcta gactacgtca cccgccccgt    60
tcc                                                                  63

<210> SEQ ID NO 16
<211> LENGTH: 39
<212> TYPE: DNA
<213> ORGANISM: Artificial Sequence
<220> FEATURE:
<221> NAME/KEY: primer_bind
<222> LOCATION: (1)..(39)
<223> OTHER INFORMATION: /Note="primer ITR-BSN"
<223> OTHER INFORMATION: Description of Artificial Sequence: primer

<400> SEQUENCE: 16
cgggatccgt cgacgcggcc gcatcatcaa taatatacc                 39

<210> SEQ ID NO 17
<211> LENGTH: 10
<212> TYPE: DNA
<213> ORGANISM: Artificial Sequence
<220> FEATURE:
<221> NAME/KEY: misc_feature
<222> LOCATION: (1)..(10)
<223> OTHER INFORMATION: /Note="phosphorylated NSI linker"
<223> OTHER INFORMATION: Description of Artificial Sequence: linker NSI

<400> SEQUENCE: 17
cgatgcatcg                                                 10

<210> SEQ ID NO 18
<211> LENGTH: 32
<212> TYPE: DNA
<213> ORGANISM: Artificial Sequence
<220> FEATURE:
<221> NAME/KEY: primer_bind
<222> LOCATION: (1)..(32)
<223> OTHER INFORMATION: /Note="primer 1"
<223> OTHER INFORMATION: Description of Artificial Sequence: primer

<400> SEQUENCE: 18
ggggtggcca gggtacctct aggcttttgc aa                        32

<210> SEQ ID NO 19
<211> LENGTH: 29
<212> TYPE: DNA
<213> ORGANISM: Artificial Sequence
<220> FEATURE:
<221> NAME/KEY: primer_bind
```

```
<222> LOCATION: (1)..(29)
<223> OTHER INFORMATION: /Note="primer 2"
<223> OTHER INFORMATION: Description of Artificial Sequence: primer

<400> SEQUENCE: 19 gggggatcc ataaacaagt tcagaatcc                                    29

<210> SEQ ID NO 20
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: /Note="linker"
<223> OTHER INFORMATION: Description of Artificial Sequence: linker

<400> SEQUENCE: 20
agcttgaatt cccgggtacc t                                           21

<210> SEQ ID NO 21
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: /Note="linker"
<223> OTHER INFORMATION: Description of Artificial Sequence: linker

<400> SEQUENCE: 21
ctagaggtac ccgggaattc a                                           21

<210> SEQ ID NO 22
<211> LENGTH: 39
<212> TYPE: DNA
<213> ORGANISM: Artificial Sequence
<220> FEATURE:
<221> NAME/KEY: primer_bind
<222> LOCATION: (1)..(39)
<223> OTHER INFORMATION: /Note="primer ITR-EPH"
<223> OTHER INFORMATION: Description of Artificial Sequence: primer

<400> SEQUENCE: 22
cggaattctt aattaagtta acatcatcaa taatatacc                        39

<210> SEQ ID NO 23
<211> LENGTH: 66
<212> TYPE: DNA
<213> ORGANISM: Artificial Sequence
<220> FEATURE:
<221> NAME/KEY: primer_bind
<222> LOCATION: (1)..(66)
<223> OTHER INFORMATION: /Note="primer ITR-pIX"
<223> OTHER INFORMATION: Description of Artificial Sequence: primer

<400> SEQUENCE: 23
acggcgcgcc ttaagccacg cccacacatt tcagtacgta ctagtctacg tcacccgccc  60
cgttcc                                                            66

<210> SEQ ID NO 24
<211> LENGTH: 26
<212> TYPE: DNA
<213> ORGANISM: Artificial Sequence
<220> FEATURE:
<221> NAME/KEY: primer_bind
<222> LOCATION: (1)..(26)
<223> OTHER INFORMATION: /Note="primer Ad3'/Forw"
```

<223> OTHER INFORMATION: Description of Artificial Sequence: primer

<400> SEQUENCE: 24
cggaattcat caggataggg cggtgg                                         26

<210> SEQ ID NO 25
<211> LENGTH: 44
<212> TYPE: DNA
<213> ORGANISM: Artificial Sequence
<220> FEATURE:
<221> NAME/KEY: primer_bind
<222> LOCATION: (1)..(44)
<223> OTHER INFORMATION: /Note="primer Ad3'/Rev"
<223> OTHER INFORMATION: Description of Artificial Sequence: primer

<400> SEQUENCE: 25
cgggatccta tcgatattta aatgttttag ggcggagtaa cttg                     44

<210> SEQ ID NO 26
<211> LENGTH: 37
<212> TYPE: DNA
<213> ORGANISM: Artificial Sequence
<220> FEATURE:
<221> NAME/KEY: primer_bind
<222> LOCATION: (1)..(37)
<223> OTHER INFORMATION: /Note="primer PA-pIX1"
<223> OTHER INFORMATION: Description of Artificial Sequence: primer

<400> SEQUENCE: 26
taagccacta gtacgtactg aaatgtgtgg gcgtggc                             37

<210> SEQ ID NO 27
<211> LENGTH: 43
<212> TYPE: DNA
<213> ORGANISM: Artificial Sequence
<220> FEATURE:
<221> NAME/KEY: primer_bind
<222> LOCATION: (1)..(43)
<223> OTHER INFORMATION: /Note="primer PA-pIX2"
<223> OTHER INFORMATION: Description of Artificial Sequence: primer

<400> SEQUENCE: 27
ttaagccacg cccacacatt tcagtacgta ctagtggctt aat                      43

<210> SEQ ID NO 28
<211> LENGTH: 10
<212> TYPE: DNA
<213> ORGANISM: Artificial Sequence
<220> FEATURE:
<221> NAME/KEY: misc_feature
<222> LOCATION: (1)..(10)
<223> OTHER INFORMATION: /Note="Sal linker"
<223> OTHER INFORMATION: Description of Artificial Sequence: linker

<400> SEQUENCE: 28
ttaagtcgac                                                           10

<210> SEQ ID NO 29
<211> LENGTH: 23
<212> TYPE: DNA
<213> ORGANISM: Artificial Sequence
<220> FEATURE:
<221> NAME/KEY: misc_feature
<222> LOCATION: (1)..(23)
<223> OTHER INFORMATION: /Note="Pac linker"
<223> OTHER INFORMATION: Description of Artificial Sequence: linker

<400> SEQUENCE: 29

```
aattgtctta attaaccgca att                                              23
```

<210> SEQ ID NO 30
<211> LENGTH: 67
<212> TYPE: DNA
<213> ORGANISM: Artificial Sequence
<220> FEATURE:
<221> NAME/KEY: misc_feature
<222> LOCATION: (1)..(67)
<223> OTHER INFORMATION: /Note="oligo linker sequence PLL-1"
<223> OTHER INFORMATION: Description of Artificial Sequence: linker

<400> SEQUENCE: 30

```
gccatccta ggaagcttgg taccggtgaa ttcgctagcg ttaacggatc ctctagacga      60
gatctgg                                                                67
```

<210> SEQ ID NO 31
<211> LENGTH: 67
<212> TYPE: DNA
<213> ORGANISM: Artificial Sequence
<220> FEATURE:
<221> NAME/KEY: misc_feature
<222> LOCATION: (1)..(67)
<223> OTHER INFORMATION: /Note="oligo linker sequence PLL-2"
<223> OTHER INFORMATION: Description of Artificial Sequence: linker

<400> SEQUENCE: 31

```
ccagatctcg tctagaggat ccgttaacgc tagcgaattc accggtacca agcttcctag      60
ggatggc                                                                67
```

<210> SEQ ID NO 32
<211> LENGTH: 39
<212> TYPE: DNA
<213> ORGANISM: Artificial Sequence
<220> FEATURE:
<221> NAME/KEY: primer_bind
<222> LOCATION: (1)..(39)
<223> OTHER INFORMATION: /Note="primer CMVplus"
<223> OTHER INFORMATION: Description of Artificial Sequence: primer

<400> SEQUENCE: 32

```
gatcggtacc actgcagtgg tcaatattgg ccattagcc                             39
```

<210> SEQ ID NO 33
<211> LENGTH: 29
<212> TYPE: DNA
<213> ORGANISM: Artificial Sequence
<220> FEATURE:
<221> NAME/KEY: primer_bind
<222> LOCATION: (1)..(29)
<223> OTHER INFORMATION: /Note="primer CMVminA"
<223> OTHER INFORMATION: Description of Artificial Sequence: primer

<400> SEQUENCE: 33

```
gatcaagctt ccaatgcacc gttcccggc                                        29
```

<210> SEQ ID NO 34
<211> LENGTH: 23
<212> TYPE: DNA
<213> ORGANISM: Artificial Sequence
<220> FEATURE:
<221> NAME/KEY: primer_bind
<222> LOCATION: (1)..(23)
<223> OTHER INFORMATION: /Note="primer DELTAE2A.SnaBI"
<223> OTHER INFORMATION: Description of Artificial Sequence: primer

<400> SEQUENCE: 34

```
ggcgtacgta gccctgtcga aag                                                  23
```

<210> SEQ ID NO 35
<211> LENGTH: 35
<212> TYPE: DNA
<213> ORGANISM: Artificial Sequence
<220> FEATURE:
<221> NAME/KEY: primer_bind
<222> LOCATION: (1)..(35)
<223> OTHER INFORMATION: /Note="primer DELTAE2A.DBP-start"
<223> OTHER INFORMATION: Description of Artificial Sequence: primer

<400> SEQUENCE: 35

```
ccaatgcatt cgaagtactt ccttctccta taggc                                     35
```

<210> SEQ ID NO 36
<211> LENGTH: 22
<212> TYPE: DNA
<213> ORGANISM: Artificial Sequence
<220> FEATURE:
<221> NAME/KEY: primer_bind
<222> LOCATION: (1)..(22)
<223> OTHER INFORMATION: /Note="primer DELTAE2A.DBP-stop"
<223> OTHER INFORMATION: Description of Artificial Sequence: primer

<400> SEQUENCE: 36

```
ccaatgcata cggcgcagac gg                                                   22
```

<210> SEQ ID NO 37
<211> LENGTH: 21
<212> TYPE: DNA
<213> ORGANISM: Artificial Sequence
<220> FEATURE:
<221> NAME/KEY: primer_bind
<222> LOCATION: (1)..(21)
<223> OTHER INFORMATION: /Note="primer DELTAE2A.BamHI"
<223> OTHER INFORMATION: Description of Artificial Sequence: primer

<400> SEQUENCE: 37

```
gaggtggatc ccatggacga g                                                    21
```

<210> SEQ ID NO 38
<211> LENGTH: 20
<212> TYPE: DNA
<213> ORGANISM: Artificial Sequence
<220> FEATURE:
<221> NAME/KEY: primer_bind
<222> LOCATION: (1)..(20)
<223> OTHER INFORMATION: /Note="primer Ad101"
<223> OTHER INFORMATION: Description of Artificial Sequence: primer

<400> SEQUENCE: 38

```
tgattcacat cggtcagtgc                                                      20
```

<210> SEQ ID NO 39
<211> LENGTH: 42
<212> TYPE: DNA
<213> ORGANISM: Artificial Sequence
<220> FEATURE:
<221> NAME/KEY: misc_feature
<222> LOCATION: (1)..(42)
<223> OTHER INFORMATION: /Note="oligonucleotide NY-up"
<223> OTHER INFORMATION: Description of Artificial Sequence:
      oligonucleotide

<400> SEQUENCE: 39

```
cgacatatgt agatgcatta gtttgtgtta tgtttcaacg tg                             42
```

```
<210> SEQ ID NO 40
<211> LENGTH: 18
<212> TYPE: DNA
<213> ORGANISM: Artificial Sequence
<220> FEATURE:
<221> NAME/KEY: misc_feature
<222> LOCATION: (1)..(18)
<223> OTHER INFORMATION: /Note="oligonucleotide NY-down"
<223> OTHER INFORMATION: Description of Artificial Sequence:
      oligonucleotide

<400> SEQUENCE: 40
ggagaccact gccatgtt                                                 18

<210> SEQ ID NO 41
<211> LENGTH: 18
<212> TYPE: DNA
<213> ORGANISM: Artificial Sequence
<220> FEATURE:
<221> NAME/KEY: misc_feature
<222> LOCATION: (1)..(18)
<223> OTHER INFORMATION: /Note="oligonucleotide DELTAhex1"
<223> OTHER INFORMATION: Description of Artificial Sequence:
      oligonucleotide

<400> SEQUENCE: 41
cctggtgctg ccaacagc                                                 18

<210> SEQ ID NO 42
<211> LENGTH: 30
<212> TYPE: DNA
<213> ORGANISM: Artificial Sequence
<220> FEATURE:
<221> NAME/KEY: misc_feature
<222> LOCATION: (1)..(30)
<223> OTHER INFORMATION: /Note="oligonucleotide DELTAhex2"
<223> OTHER INFORMATION: Description of Artificial Sequence:
      oligonucleotide

<400> SEQUENCE: 42
ccggatccac tagtggaaag cgggcgcgcg                                    30

<210> SEQ ID NO 43
<211> LENGTH: 35
<212> TYPE: DNA
<213> ORGANISM: Artificial Sequence
<220> FEATURE:
<221> NAME/KEY: misc_feature
<222> LOCATION: (1)..(35)
<223> OTHER INFORMATION: /Note="oligonucleotide DELTAhex3"
<223> OTHER INFORMATION: Description of Artificial Sequence:
      oligonucleotide

<400> SEQUENCE: 43
ccggatccaa ttgagaagca agcaacatca acaac                              35

<210> SEQ ID NO 44
<211> LENGTH: 19
<212> TYPE: DNA
<213> ORGANISM: Artificial Sequence
<220> FEATURE:
<221> NAME/KEY: misc_feature
<222> LOCATION: (1)..(19)
<223> OTHER INFORMATION: /Note="oligonucleotide DELTAhex4"
<223> OTHER INFORMATION: Description of Artificial Sequence:
      oligonucleotide

<400> SEQUENCE: 44
gagaagggca tggaggctg                                                19
```

```
<210> SEQ ID NO 45
<211> LENGTH: 20
<212> TYPE: DNA
<213> ORGANISM: Artificial Sequence
<220> FEATURE:
<221> NAME/KEY: primer_bind
<222> LOCATION: (1)..(20)
<223> OTHER INFORMATION: /Note="primer DP5-F"
<223> OTHER INFORMATION: Description of Artificial Sequence: primer

<400> SEQUENCE: 45
ctgttgctgc tgctaatagc                                               20

<210> SEQ ID NO 46
<211> LENGTH: 32
<212> TYPE: DNA
<213> ORGANISM: Artificial Sequence
<220> FEATURE:
<221> NAME/KEY: primer_bind
<222> LOCATION: (1)..(32)
<223> OTHER INFORMATION: /Note="primer DP5-R"
<223> OTHER INFORMATION: Description of Artificial Sequence: primer

<400> SEQUENCE: 46
cgcggatcct gtacaactaa ggggaataca ag                                 32

<210> SEQ ID NO 47
<211> LENGTH: 33
<212> TYPE: DNA
<213> ORGANISM: Artificial Sequence
<220> FEATURE:
<221> NAME/KEY: primer_bind
<222> LOCATION: (1)..(33)
<223> OTHER INFORMATION: /Note="primer DP3-F"
<223> OTHER INFORMATION: Description of Artificial Sequence: primer

<400> SEQUENCE: 47
cgcggatccc ttaaggcaag catgtccatc ctt                                33

<210> SEQ ID NO 48
<211> LENGTH: 27
<212> TYPE: DNA
<213> ORGANISM: Artificial Sequence
<220> FEATURE:
<221> NAME/KEY: primer_bind
<222> LOCATION: (1)..(27)
<223> OTHER INFORMATION: /Note="primer DP3-3R"
<223> OTHER INFORMATION: Description of Artificial Sequence: primer

<400> SEQUENCE: 48
aaaacacgtt ttacgcgtcg acctttc                                       27

<210> SEQ ID NO 49
<211> LENGTH: 12
<212> TYPE: DNA
<213> ORGANISM: Artificial Sequence
<220> FEATURE:
<221> NAME/KEY: misc_feature
<222> LOCATION: (1)..(12)
<223> OTHER INFORMATION: /Note="NOT-I linker"
<223> OTHER INFORMATION: Description of Artificial Sequence: linker

<400> SEQUENCE: 49
aattgcggcc gc                                                       12

<210> SEQ ID NO 50
<211> LENGTH: 21
<212> TYPE: DNA
```

```
<213> ORGANISM: Artificial Sequence
<220> FEATURE:
<221> NAME/KEY: primer_bind
<222> LOCATION: (1)..(21)
<223> OTHER INFORMATION: /Note="primer Ea-1"
<223> OTHER INFORMATION: Description of Artificial Sequence: primer

<400> SEQUENCE: 50
cgtgtagtgt atttataccc g                                              21

<210> SEQ ID NO 51
<211> LENGTH: 21
<212> TYPE: DNA
<213> ORGANISM: Artificial Sequence
<220> FEATURE:
<221> NAME/KEY: primer_bind
<222> LOCATION: (1)..(21)
<223> OTHER INFORMATION: /Note="primer Ea-2"
<223> OTHER INFORMATION: Description of Artificial Sequence: primer

<400> SEQUENCE: 51
tcgtcactgg gtggaaagcc a                                              21

<210> SEQ ID NO 52
<211> LENGTH: 21
<212> TYPE: DNA
<213> ORGANISM: Artificial Sequence
<220> FEATURE:
<221> NAME/KEY: primer_bind
<222> LOCATION: (1)..(21)
<223> OTHER INFORMATION: /Note="primer Ea-3"
<223> OTHER INFORMATION: Description of Artificial Sequence: primer

<400> SEQUENCE: 52
tacccgccgt cctaaaatgg c                                              21

<210> SEQ ID NO 53
<211> LENGTH: 20
<212> TYPE: DNA
<213> ORGANISM: Artificial Sequence
<220> FEATURE:
<221> NAME/KEY: primer_bind
<222> LOCATION: (1)..(20)
<223> OTHER INFORMATION: /Note="primer Ea-5"
<223> OTHER INFORMATION: Description of Artificial Sequence: primer

<400> SEQUENCE: 53
tggacttgag ctgtaaacgc                                                20

<210> SEQ ID NO 54
<211> LENGTH: 21
<212> TYPE: DNA
<213> ORGANISM: Artificial Sequence
<220> FEATURE:
<221> NAME/KEY: primer_bind
<222> LOCATION: (1)..(21)
<223> OTHER INFORMATION: /Note="primer Ep-2"
<223> OTHER INFORMATION: Description of Artificial Sequence: primer

<400> SEQUENCE: 54
gcctccatgg aggtcagatg t                                              21

<210> SEQ ID NO 55
<211> LENGTH: 20
<212> TYPE: DNA
<213> ORGANISM: Artificial Sequence
<220> FEATURE:
<221> NAME/KEY: primer_bind
<222> LOCATION: (1)..(20)
```

-continued

<223> OTHER INFORMATION: /Note="primer Eb-1"
<223> OTHER INFORMATION: Description of Artificial Sequence: primer

<400> SEQUENCE: 55
gcttgagccc gagacatgtc                                             20

<210> SEQ ID NO 56
<211> LENGTH: 24
<212> TYPE: DNA
<213> ORGANISM: Artificial Sequence
<220> FEATURE:
<221> NAME/KEY: primer_bind
<222> LOCATION: (1)..(24)
<223> OTHER INFORMATION: /Note="primer Eb-2"
<223> OTHER INFORMATION: Description of Artificial Sequence: primer

<400> SEQUENCE: 56
cccctcgagc tcaatctgta tctt                                        24

<210> SEQ ID NO 57
<211> LENGTH: 27
<212> TYPE: DNA
<213> ORGANISM: Artificial Sequence
<220> FEATURE:
<221> NAME/KEY: primer_bind
<222> LOCATION: (1)..(27)
<223> OTHER INFORMATION: /Note="primer SV40-1"
<223> OTHER INFORMATION: Description of Artificial Sequence: primer

<400> SEQUENCE: 57
gggggatccg aacttgttta ttgcagc                                     27

<210> SEQ ID NO 58
<211> LENGTH: 25
<212> TYPE: DNA
<213> ORGANISM: Artificial Sequence
<220> FEATURE:
<221> NAME/KEY: primer_bind
<222> LOCATION: (1)..(25)
<223> OTHER INFORMATION: /Note="primer SV40-2"
<223> OTHER INFORMATION: Description of Artificial Sequence: primer

<400> SEQUENCE: 58
gggagatcta gacatgataa gatac                                       25

<210> SEQ ID NO 59
<211> LENGTH: 27
<212> TYPE: DNA
<213> ORGANISM: Artificial Sequence
<220> FEATURE:
<221> NAME/KEY: primer_bind
<222> LOCATION: (1)..(27)
<223> OTHER INFORMATION: /Note="primer Ad5-1"
<223> OTHER INFORMATION: Description of Artificial Sequence: primer

<400> SEQUENCE: 59
gggagatctg tactgaaatg tgtgggc                                     27

<210> SEQ ID NO 60
<211> LENGTH: 24
<212> TYPE: DNA
<213> ORGANISM: Artificial Sequence
<220> FEATURE:
<221> NAME/KEY: primer_bind
<222> LOCATION: (1)..(24)
<223> OTHER INFORMATION: /Note="primer Ad5-2"
<223> OTHER INFORMATION: Description of Artificial Sequence: primer

<400> SEQUENCE: 60

```
ggaggctgca gtctccaacg gcgt                                              24
```

<210> SEQ ID NO 61
<211> LENGTH: 27
<212> TYPE: DNA
<213> ORGANISM: Artificial Sequence
<220> FEATURE:
<221> NAME/KEY: primer_bind
<222> LOCATION: (1)..(27)
<223> OTHER INFORMATION: /Note="primer ITR1"
<223> OTHER INFORMATION: Description of Artificial Sequence: primer

<400> SEQUENCE: 61

```
gggggatcct caaatcgtca cttccgt                                           27
```

<210> SEQ ID NO 62
<211> LENGTH: 27
<212> TYPE: DNA
<213> ORGANISM: Artificial Sequence
<220> FEATURE:
<221> NAME/KEY: primer_bind
<222> LOCATION: (1)..(27)
<223> OTHER INFORMATION: /Note="primer ITR2"
<223> OTHER INFORMATION: Description of Artificial Sequence: primer

<400> SEQUENCE: 62

```
ggggtctaga catcatcaat aatatac                                           27
```

<210> SEQ ID NO 63
<211> LENGTH: 32
<212> TYPE: DNA
<213> ORGANISM: Artificial Sequence
<220> FEATURE:
<221> NAME/KEY: primer_bind
<222> LOCATION: (1)..(32)
<223> OTHER INFORMATION: /Note="primer PCR/MLP1"
<223> OTHER INFORMATION: Description of Artificial Sequence: primer

<400> SEQUENCE: 63

```
ggcgaattcg tcgacatcat caataatata cc                                     32
```

<210> SEQ ID NO 64
<211> LENGTH: 32
<212> TYPE: DNA
<213> ORGANISM: Artificial Sequence
<220> FEATURE:
<221> NAME/KEY: primer_bind
<222> LOCATION: (1)..(32)
<223> OTHER INFORMATION: /Note="primer PCR/MLP2"
<223> OTHER INFORMATION: Description of Artificial Sequence: primer

<400> SEQUENCE: 64

```
ggcgaattcg gtaccatcat caataatata cc                                     32
```

<210> SEQ ID NO 65
<211> LENGTH: 17
<212> TYPE: DNA
<213> ORGANISM: Artificial Sequence
<220> FEATURE:
<221> NAME/KEY: primer_bind
<222> LOCATION: (1)..(17)
<223> OTHER INFORMATION: /Note="primer PCR/MLP3"
<223> OTHER INFORMATION: Description of Artificial Sequence: primer

<400> SEQUENCE: 65

```
ctgtgtacac cggcgca                                                      17
```

```
-continued

<210> SEQ ID NO 66
<211> LENGTH: 49
<212> TYPE: DNA
<213> ORGANISM: Artificial Sequence
<220> FEATURE:
<221> NAME/KEY: primer_bind
<222> LOCATION: (1)..(49)
<223> OTHER INFORMATION: /Note="primer HP/asp1"
<223> OTHER INFORMATION: Description of Artificial Sequence: primer

<400> SEQUENCE: 66
gtacactgac ctagtgccgc ccgggaaagc ccgggcggca ctaggtcag              49

<210> SEQ ID NO 67
<211> LENGTH: 50
<212> TYPE: DNA
<213> ORGANISM: Artificial Sequence
<220> FEATURE:
<221> NAME/KEY: primer_bind
<222> LOCATION: (1)..(50)
<223> OTHER INFORMATION: /Note="primer HP/asp2"
<223> OTHER INFORMATION: Description of Artificial Sequence: primer

<400> SEQUENCE: 67
gtacctgacc tagtgccgcc cgggctttgc ccgggcggca ctaggtcagt             50

<210> SEQ ID NO 68
<211> LENGTH: 55
<212> TYPE: DNA
<213> ORGANISM: Artificial Sequence
<220> FEATURE:
<221> NAME/KEY: primer_bind
<222> LOCATION: (1)..(55)
<223> OTHER INFORMATION: /Note="primer HP/cla1"
<223> OTHER INFORMATION: Description of Artificial Sequence: primer

<400> SEQUENCE: 68
gtacattgac ctagtgccgc ccgggcaaag cccgggcggc actaggtcaa tcgat       55

<210> SEQ ID NO 69
<211> LENGTH: 54
<212> TYPE: DNA
<213> ORGANISM: Artificial Sequence
<220> FEATURE:
<221> NAME/KEY: primer_bind
<222> LOCATION: (1)..(54)
<223> OTHER INFORMATION: /Note="primer HP/cla2"
<223> OTHER INFORMATION: Description of Artificial Sequence: primer

<400> SEQUENCE: 69
gtacatcgat tgacctagtg ccgcccgggt tgcccgggc ggcactaggt caat          54
```

What is claimed is:

1. A method for generating an adenoviral vector comprising welding together two nucleic acid molecules wherein said two nucleic acid molecules comprise partially overlapping sequences capable of combining with one another allowing the generation of a physically linked nucleic acid comprising at least two functional adenovirus inverted terminal repeats, a functional encapsulation signal and a nucleic acid encoding at least one adenoviral E1-region protein, at least one adenoviral E2-region encoded protein and/or at least one adenoviral E4-region encoded protein and a nucleic acid sequence of interest or functional parts thereof and wherein at least one of said E1-region encoded proteins is under transcriptional control of a conditionally active promoter.

2. A method for generating an adenoviral vector comprising welding together, through homologous recombination, two nucleic acid molecules comprising partially overlapping sequences wherein said overlapping sequences of each nucleic acid molecule of said two nucleic acid molecules comprise essentially only one continuous sequence such that homologous recombination may occur, leading to the generation of a physically linked nucleic acid comprising at least two functional adenovirus inverted terminal repeats, a functional encapsulation signal and a nucleic acid sequence of interest or functional parts thereof; at least one nucleic acid molecule of said two nucleic acid molecules comprising a chimeric adenoviral capsid encoding nucleic acid comprising nucleic acid sequences from two different adenovirus serotypes, wherein said welding together is performed in a cell as deposited at the ECACC under number 96022940.

3. A method for generating an adenoviral vector comprising welding together through homologous recombination, two nucleic acid molecules comprising partially overlapping sequences wherein said overlapping sequences of each nucleic acid molecule of said two nucleic acid molecules comprise essentially only one continuous sequence whereby homologous recombination may occur, leading to the generation of a physically linked nucleic acid comprising at least two functional adenovirus inverted terminal repeats, a functional encapsulation signal, a nucleic acid encoding at least one adenoviral E1-region protein, at least one adenoviral E2-region encoded protein and/or at least one adenoviral E4-region encoded protein and a nucleic acid sequence of interest or functional parts thereof and wherein at least one of said E1-region encoded proteins is under transcriptional control of a conditionally active promoter.

4. A method for generating an adenoviral vector comprising welding together through homologous recombination two nucleic acid molecules, wherein said two nucleic acid molecules comprise partially overlapping sequences capable of combining with one another allowing the generation of a physically linked nucleic acid comprising at least two functional adenovirus inverted terminal repeats, a functional encapsulation signal and a nucleic acid sequence of interest or functional parts thereof; at least one of said molecules comprising a chimeric adenoviral capsid encoding nucleic acid comprising nucleic acid sequences from two different adenovirus serotypes, wherein said welding together is performed in a cell as deposited at the ECACC under number 96022940.

5. The method according to claim 4, wherein at least one of said two nucleic acid molecules is derived from an adenoviral vector library, said adenoviral vector library comprising a multitude of nucleic acid molecules including different nucleic acids of interest.

6. A method for generating an adenoviral vector comprising welding together at least two nucleic acid molecules wherein said at least two nucleic acid molecules comprise partially overlapping sequences capable of combining with one another allowing the generation of a physically linked nucleic acid comprising at least two functional adenovirus inverted terminal repeats, a functional encapsulation signal and a nucleic acid sequence of interest; at least one of said at least two nucleic acid molecules comprising a chimeric adenoviral capsid encoding nucleic acid comprising nucleic acid sequences from at least two different adenovirus serotypes, wherein said welding together is performed through homologous recombination of overlapping sequences in the nucleic acid and wherein said welding together is performed in a cell as deposited at the ECACC under number 96022940.

7. The method according to claim 6, wherein said capsid protein is a hexon protein.

8. The method according to claim 6, wherein said capsid protein is a penton base protein.

9. The method according to claim 6, wherein said capsid protein is a fiber protein.

10. The method according to claim 6, wherein said capsid protein includes at least a part of a fiber protein of a subgroup B-type adenovirus.

11. The method according to claim 10, wherein said subgroup B-type adenovirus is adenovirus 16.

* * * * *

UNITED STATES PATENT AND TRADEMARK OFFICE
CERTIFICATE OF CORRECTION

PATENT NO.       : 6,878,549 B1                                    Page 1 of 1
APPLICATION NO. : 09/332803
DATED            : April 12, 2005
INVENTOR(S)      : Ronald Vogels and Abraham Bout It is certified that error appears in the above-identified patent and that said Letters Patent is hereby corrected as shown below:

| | | |
|---|---|---|
| COLUMN 31 | LINE 5 | change "E1A and E1 B coding" to --E1A and E1B coding-- |
| COLUMN 33 | LINE 59 | change "proteins(not shown)" to --proteins (not shown)-- |
| COLUMN 37 | LINE 44 | change "EWE/Ad.AflII-EcoRI" to --pWE/Ad.AflII EcoRI-- |
| COLUMN 38 | LINE 4 | change "GGAAAAATA" to --GGA AAA ATA-- |
| COLUMN 38 | LINE 29 | change "HSA2,5'-GTT" to --HSA2, 5'-GTT-- |
| COLUMN 39 | LINE 35 | change "~80!k" to --~80%-- |
| COLUMN 39 | LINE 42 | change "~50t" to --~50%-- |
| COLUMN 40 | LINE 24 | change "(KS_)" to --(KS⁻)-- |
| COLUMN 44 | LINE 40 | change "(nt. 0.2533-2668" to --(nt. 2533-2668-- |
| COLUMN 51 | LINE 32 | change "BsxGI-BamHI" to --BsrGI-BamHI-- |
| COLUMN 54 | LINE 62 | change "TTAAGT" to --TTA AGT-- |
| COLUMN 56 | LINE 52 | change "5'-CCC" to --5'-CCG-- |
| COLUMN 57 | LINE 49 | change "GCAAGC" to --GCA AGC-- |
| COLUMN 57 | LINE 50 | change "(SEQ. ID. NO. 47)and" to --(SEQ. ID. NO. 47) and-- |
| COLUMN 59 | LINE 58 | change "humanIL1 αa," to --humanIL1αa,-- |
| COLUMN 62 | LINE 2 | change "pWE/Ad.DS'" to --pWE/Ad.D5'- |
| CLAIM 2 COLUMN 90 LINES 62-63 | | change "a chimeric adenoviral capsid encoding nucleic acid comprising nucleic acid sequences" to --an adenoviral capsid protein encoding nucleic acid derived-- |
| CLAIM 4 COLUMN 91 LINE 24 | | change "a chimeric adenoviral capsid encoding" to --an adenoviral capsid protein encoding-- |
| CLAIM 4 COLUMN 91 LINE 25 | | change "sequences" to --derived-- |
| CLAIM 6 COLUMN 92 LINES 11-13 | | change "a chimeric adenoviral capsid encoding nucleic acid comprising nucleic acid sequences" to --adenoviral capsid proteins encoding nucleic acid derived-- |

Signed and Sealed this

Twenty-sixth Day of October, 2010

David J. Kappos
*Director of the United States Patent and Trademark Office*